(12) United States Patent
Hermanson et al.

(10) Patent No.: US 12,201,550 B2
(45) Date of Patent: *Jan. 21, 2025

(54) SYSTEM AND METHOD FOR DELIVERING A THERAPY AND SENSING A BIOLOGICAL ACTIVITY IN THE MOUTH

(71) Applicant: Split Rock Scientific, Inc., San Mateo, CA (US)

(72) Inventors: Christopher Hermanson, Santa Cruz, CA (US); Amit Rajguru, Lafayette, CA (US)

(73) Assignee: Split Rock Scientific, Inc., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/984,138

(22) Filed: Nov. 9, 2022

(65) Prior Publication Data

US 2023/0081614 A1  Mar. 16, 2023

Related U.S. Application Data

(63) Continuation of application No. 16/563,727, filed on Sep. 6, 2019, now Pat. No. 11,529,255, which is a
(Continued)

(51) Int. Cl.
*A61F 5/56* (2006.01)
*A61F 5/00* (2006.01)
(Continued)

(52) U.S. Cl.
CPC ................ *A61F 5/566* (2013.01); *A61F 5/00* (2013.01); *A61F 5/56* (2013.01); *A61M 15/00* (2013.01);
(Continued)

(58) Field of Classification Search
CPC ... A61F 5/566; A61F 5/56; A61F 5/00; A61B 5/4818; A61N 1/0548; A61N 1/36014;
(Continued)

(56) References Cited

U.S. PATENT DOCUMENTS 4,966,580 A   10/1990   Turner et al.
4,995,404 A   2/1991    Nemir
(Continued)

FOREIGN PATENT DOCUMENTS

EP   1506746 B1 * 12/2009 ......... A61C 17/0211
WO   9514449 A1   6/1995
(Continued)

OTHER PUBLICATIONS

United State Patent and Trademark Office, International Search Report and Written Opinion, PCT Application No. PCT/US2012/037392, mailed Aug. 27, 2012, 12 pages.
(Continued)

*Primary Examiner* — Tarla R Patel
(74) *Attorney, Agent, or Firm* — Mahamedi IP Law LLP

(57) ABSTRACT

Methods, devices, and systems are disclosed for controlled delivery of a therapy, such as a stimulant, to a mouth of a subject via an oral device positioned in a secured configuration in the mouth. At least one of a tongue position stimulator (TST) and tongue position sensor (TSE) is provided, according to certain aspects. According to another aspect, a stimulus is delivered to the mouth and/or tongue via a mouthpiece secured to the subject's teeth. In another regard, a stimulus is delivered that generates a natural response to eliminate or reduce sleep disorders, such as for example at least one of snoring and obstructive sleep apnea.

20 Claims, 22 Drawing Sheets

Related U.S. Application Data continuation of application No. 13/668,155, filed on Nov. 2, 2012, now Pat. No. 10,420,672, which is a continuation-in-part of application No. 13/649,967, filed on Oct. 11, 2012, now Pat. No. 9,549,841, which is a continuation-in-part of application No. PCT/US2012/037392, filed on May 10, 2012.

(60) Provisional application No. 61/603,671, filed on Feb. 27, 2012, provisional application No. 61/551,927, filed on Oct. 27, 2011, provisional application No. 61/484,520, filed on May 10, 2011.

(51) Int. Cl.
*A61M 15/00* (2006.01)
*A61M 16/00* (2006.01)
*A61M 16/04* (2006.01)
*A61M 31/00* (2006.01)

(52) U.S. Cl.
CPC ...... *A61M 16/024* (2017.08); *A61M 16/0488* (2013.01); *A61M 16/049* (2014.02); *A61M 31/00* (2013.01); *A61M 2205/3306* (2013.01); *A61M 2205/3317* (2013.01); *A61M 2205/3331* (2013.01); *A61M 2205/3375* (2013.01)

(58) Field of Classification Search
CPC . A61N 1/3601; A61N 1/36031; A61M 15/00; A61M 16/024; A61M 16/0488; A61M 16/049; A61M 31/00; A61M 2205/3306; A61M 2205/3317; A61M 2205/3331; A61M 2205/3375; A61M 2230/60
USPC ......................................................... 128/848
See application file for complete search history.

(56) References Cited

U.S. PATENT DOCUMENTS

| | | |
|---|---|---|
| 5,013,321 A | 5/1991 | MacVane |
| 5,052,409 A | 10/1991 | Tepper |
| 5,078,153 A | 1/1992 | Nordlander et al. |
| 5,078,734 A | 1/1992 | Noble |
| 5,176,705 A | 1/1993 | Noble |
| 5,490,520 A | 2/1996 | Schaefer et al. |
| 5,624,439 A | 4/1997 | Edwards et al. |
| 5,792,067 A * | 8/1998 | Karell ............... A61N 1/36031 607/42 |
| 5,924,863 A | 7/1999 | Jacobs et al. |
| 5,957,133 A | 9/1999 | Hart |
| 6,068,475 A | 5/2000 | Stoyka, Jr. |
| 6,076,526 A | 6/2000 | Abdelmessih |
| 6,089,864 A | 7/2000 | Buckner et al. |
| 6,164,278 A | 12/2000 | Nissani |
| 6,212,435 B1 * | 4/2001 | Lattner ............... A61N 1/0548 607/42 |
| 6,279,326 B1 | 8/2001 | Boucher et al. |
| 6,494,209 B2 | 12/2002 | Kulick |
| 6,544,199 B1 | 4/2003 | Morris |
| 6,619,290 B1 | 9/2003 | Zacco |
| 6,877,513 B2 | 4/2005 | Scarberry et al. |
| 6,997,186 B2 | 2/2006 | Robertson et al. |
| 7,039,468 B2 | 5/2006 | Freed et al. |
| 7,051,731 B1 | 5/2006 | Rogerson |
| 7,137,393 B2 | 11/2006 | Pivovarov |
| 7,935,065 B2 | 5/2011 | Marten et al. |
| 8,517,729 B2 | 8/2013 | Martin et al. |
| 8,532,763 B2 | 9/2013 | De Vos |
| 9,549,841 B2 * | 1/2017 | Hermanson ......... A61M 16/024 |
| 10,420,672 B2 * | 9/2019 | Hermanson ............. A61F 5/56 |
| 10,874,542 B2 * | 12/2020 | Hermanson ......... A61M 16/049 |
| 11,529,255 B2 * | 12/2022 | Hermanson ........... A61M 31/00 |
| 2002/0144685 A1 | 10/2002 | Ivanovich et al. |
| 2004/0211430 A1 | 10/2004 | Pivovarov |
| 2006/0096600 A1 | 5/2006 | Witt et al. |
| 2006/0112962 A1 | 6/2006 | Tebbutt et al. |
| 2006/0174874 A1 | 8/2006 | Jagger et al. |
| 2006/0282010 A1 | 12/2006 | Martin et al. |
| 2007/0173893 A1 | 7/2007 | Pitts |
| 2007/0204867 A1 * | 9/2007 | Kennedy, Jr. ......... A61J 15/0011 128/859 |
| 2007/0221224 A1 | 9/2007 | Pittman et al. |
| 2007/0231396 A1 | 10/2007 | Ray |
| 2008/0161750 A1 * | 7/2008 | Pontis .................. A61J 15/0011 604/27 |
| 2008/0272153 A1 * | 11/2008 | Hochstadter ........... A61C 13/01 222/373 |
| 2009/0048647 A1 | 2/2009 | Tingey |
| 2009/0078275 A1 | 3/2009 | Hedge et al. |
| 2009/0117513 A1 | 5/2009 | Nemeh et al. |
| 2009/0210032 A1 | 8/2009 | Beiski et al. |
| 2010/0016908 A1 | 1/2010 | Martin et al. |
| 2010/0031959 A1 | 2/2010 | Avidor et al. |
| 2010/0125310 A1 | 5/2010 | Wilson et al. |
| 2010/0268107 A1 | 10/2010 | De Heer |
| 2010/0312311 A1 | 12/2010 | Wolff et al. |
| 2010/0313898 A1 | 12/2010 | Richard et al. |
| 2011/0213228 A1 | 9/2011 | Martin |
| 2011/0270166 A1 | 11/2011 | Martin et al. |

FOREIGN PATENT DOCUMENTS

| | | |
|---|---|---|
| WO | 9900058 A1 | 1/1999 |
| WO | 02066111 A1 | 8/2002 |
| WO | 2008100779 A1 | 8/2008 |

OTHER PUBLICATIONS

Korean Intellectual Property Office, International Search Report and Written Opinion, PCT Application No. PCT/US2012/059796, mailed Mar. 26, 2013, 9 pages.

* cited by examiner

SYSTEM AND METHOD FOR DELIVERING A THERAPY AND SENSING A BIOLOGICAL ACTIVITY IN THE MOUTH

CROSS-REFERENCE TO RELATED APPLICATIONS

This application is a Continuation of U.S. patent application Ser. No. 16/563,727, filed Sep. 6, 2019, which is a Continuation of U.S. patent application Ser. No. 13/668,155, filed Nov. 2, 2012, issued as U.S. Pat. No. 10,420,672, which is a Continuation-In-Part of U.S. patent application Ser. No. 13/649,967, filed on Oct. 11, 2012, issued as U.S. Pat. No. 9,549,841, which A) claims benefit of priority to each of (i) U.S. provisional patent application Ser. No. 61/603,671, filed on Feb. 27, 2012, (ii) U.S. provisional patent application Ser. No. 61/551,927 filed on Oct. 27, 2011, and (iii) U.S. provisional patent application Ser. No. 61/484,520 filed on May 10, 2011; and which B) is a continuation-in-part of PCT international application number PCT/US2012/037392 filed on May 10, 2012. All of the aforementioned applications referenced in this paragraph or incorporated by reference in their respective entirety.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

The present disclosure relates to methods, devices, and/or systems for delivering therapies and sensing biologic activities via oral appliances in the mouth, in particular for stimulating and sensing tongue activity during sleep, and including in particular for treating sleep disorder breathing, including but not limited conditions of obstructive sleep apnea, snoring, or mild sleep apnea.

2. Background and Description of Related Art

Snoring, which is very common among humans, is a noise produced while breathing during sleep as a result of certain conditions within the body. In most cases, snoring results from vibration of the soft palate and uvula. Snoring often involves a displacement of the tongue from its rest position as well as breathing through the mouth resulting from the abnormal positioning and functioning of the tongue. Snoring can be reduced if the tongue is drawn forward to a more normal position (e.g., in contact with the anatomical folds or wrinkles (rugae) or the mucosa of the anterior palatal region of the mouth. When in an abnormal position, the tongue leaves a space for the passage of air between the hard palate and the top of the tongue and over the soft palate. The passage of air over the soft palate can cause vibrations which are the source behind the snoring sound.

While some degree of snoring is tolerable and has no significant adverse consequence, a common problem is that, on its own, snoring can disturb the sleep of others near the snoring individual. As a result, snoring can result in a diminished ability to remain attentive on both the individual snoring as well as others whose sleep might be adversely affected by the snoring party. As a result, even moderate snoring can result in a reduction in work efficiency and lead to a higher risk of industrial and driving accidents.

A more serious sleep disorder can result from symptomatic, repeated upper airway obstruction during sleep, commonly referred to as Obstructive Sleep Apnea (OSA). "Apnea" is a Greek word meaning without breath. Individual suffering from sleep apnea literally stop breathing in their sleep. It is not uncommon for the incidence of apnea events to occur hundreds of times during the night.

In a given night, the number of involuntary breathing pauses or "apneic events" could be as high as 20 to 60 or more per hour. These breathing pauses are almost always accompanied by snoring between apnea episodes. Sleep apnea can also be characterized by choking sensations. Ingestion of alcohol and sleeping pills increases the frequency and duration of breathing pauses in people with sleep apnea.

30-40% of OSA patients cannot tolerate first-line treatment (such as continuous positive airway pressure, CPAP. Accordingly individuals may consider other options including oral appliances and surgery. Mandibular repositioning appliances and surgery can offer benefit for selected patients, but such conventional remedies can carry risks such as temporomandibular joint disturbance, changes in dental occlusion, or tooth pain for the former and a wide spectrum of potential complications that includes dysphagia or serious perioperative events including myocardial infarction and death in the latter.

The importance of the tongue in OSA and snoring has been recognized for 30 years, as evidenced by the numerous attempts designed to prevent the tongue from falling backwards or to move it forward actively or passively. Oral appliances and multiple tongue-directed surgeries show some promise, but these remedies carry significant risks and side effects, in addition to potential significant bleeding and impairments of taste, swallowing, or speech. Because of the limitations of available passive treatments, active tongue neuromuscular stimulation techniques were attempted to implant wire electrodes, surface stimulating electrodes and hypoglossal nerve stimulation.

A number of factors contribute to OSA, including dilator muscle activation, pharyngeal anatomy, lung volume, arousal threshold, and ventilatory control, with the former two playing critical roles for most individuals. Upper airway patency relies on pharyngeal dilator muscle tone and changes in lung volume that counteract collapsing forces, principally intraluminal negative pressure generated during inspiration and anatomical narrowing of the airway. Individuals with OSA maintain pharyngeal patency with greater dilator muscle tone (principally demonstrated in the genioglossus muscle, the primary muscle within the tongue) during wakefulness; however, sleep onset results in marked decreases in muscle tone due to the loss of the wakefulness stimulus, in addition to decreases in negative pressure reflex activity and lung volume. The effect of decreased muscle tone is magnified in the presence of tongue enlargement, an anatomical abnormality often seen in OSA, perhaps related to an increase in fat deposition within the tongue base in individuals with greater body mass index.

Additional risk factors for sleep apnea include a family history of sleep apnea, excess weight, a large neck, a recessed chin, male gender, abnormalities in the structure of the upper airway, smoking, and alcohol use. Yet sleep apnea can affect both males and females of all ages, including children and any weight. Sleep apnea disturbs normal sleep patterns and people with sleep apnea often feel very sleepy during the day and their concentration and daytime performance suffer. The consequences of sleep apnea range from annoying to life-threatening. They include symptoms suggesting depression, irritability, sexual dysfunction, learning and memory difficulties, and falling asleep while at work, on the phone, or driving.

Conventional treatment with oral appliances and tongue-directed surgical procedures are based on tongue repositioning and/or size reduction. Novel tongue-directed therapies utilizing direct neuromuscular stimulation and oropharyngeal exercises have demonstrated encouraging initial results, but these approaches continue to be limited by cost, invasiveness, compliance, and/or limited effectiveness.

Untreated sleep apnea patients are 3 times (or more) likely to have automobile accidents. It has been estimated that up to 50 percent of sleep apnea patients have high blood pressure. It has recently been shown that sleep apnea contributes to high blood pressure and other cardiovascular disease. Risk for heart attack and stroke may also increase in those with sleep apnea. Sleep apnea is a common disorder that affects millions of men, women and children and is often undiagnosed. It is estimated that at least ten million Americans have unrecognized sleep apnea Polysomnography is a test that records a variety of body functions during sleep, such as the electrical activity of the brain, eye movement, muscle activity, heart rate, respiratory effort, air flow, and blood oxygen levels. These tests are used both to diagnose sleep apnea and to determine its severity. The specific therapy for sleep apnea is tailored to the individual patient based on medical history, physical examination, and the results of polysomnography. Traditionally, a therapy for sleep apnea is tailored to the individual patient based on medical history, physical examination, and the results of polysomnography.

Medications are generally not effective in the treatment of sleep apnea. While oxygen is sometimes used in patients with central apnea caused by heart failure, it is not used to treat obstructive sleep apnea. Some of the therapies include the use of Provent®, Breatherite® strip, Oral appliances that advance the mandible, continuous positive airway pressure (CPAP), or maxillomandibular advancement surgery, etc. However, some therapies may be partially or completely ineffective in addressing both snoring and/or OSA.

Recently Inspire Medical, Imthera Medical, Apnex Medical and others have been exploring ways of stimulating tongue, tongue muscle or nerves that control the tongue by implanting electrodes in the tongue to deliver electrical signals for stimulation. However, titrating safe levels of stimulation that does not disturb sleep for each patient is a challenge. Others have explored ways of stimulating the tongue base by making the patients wear oral devices. The challenge has been the same.

Given the limitations of current therapies, there is an enormous unmet need for effective, well-tolerated, safe, and minimally invasive OSA treatments. There also remains a need for reducing the incidence of snoring and/or sleep apena that does not require significant physical and/or surgical intervention on the patient. In the article, "Impaired swallowing reflex in patients with obstructive sleep apnea syndrome" (CHEST 1999; 116:17-21), Teramoto et al. published their findings that twenty (20) patients with obstructive sleep apnea also had a compromised swallowing function due to reduced upper airway muscle functions. From this study, one can conclude that increasing the swallowing frequency during sleep could result in increased upper airway muscle functions, and thus potentially reduce or eliminate snoring and obstructive sleep apnea.

In view of the above, there remains a need for an effective, safe, and noninvasive device, for use by itself or during administration of CPAP. The devices, methods and procedures described herein induce a biological response within a mouth, such as promoting tongue neuromuscular activation and anterior tongue displacement to reduce airway obstruction. Additional variations of methods, devices, and systems described herein can also increase salivation and reduce or eliminate snoring and obstructive sleep apnea by one or more of the following: stimulating swallowing, improving muscle tone and increasing frequency of swallowing.

BRIEF SUMMARY OF THE INVENTION

Stimulation of swallowing can be achieved in several ways: stimulation by taste, stimulation by smell and stimulation by mechanical effect that helps trigger the swallowing reflex. To achieve stimulation, an interface to the user is provided that allows for delivery of the stimulus in a beneficial way. Variations of the methods and devices can include the use of a stimulation appliance delivers one or more stimuli to the nose, tongue, and/or mouth to induce the effects described above. For example, variations of the stimulation appliance can include a mouthpiece, mask and/or one or more tubes placed within or in proximity to the mouth or nose.

In the cases of taste and smell stimuli, the stimulation appliance incorporates a reservoir that allows for delivery of the stimulus over the sleep period. It is important that delivery of the stimulus be controlled to achieve efficient stimulation of swallowing, without causing habituation or arousing involuntary reflexes, such as gagging. The stimulation appliance comprises means to deliver and regulate the stimulus, such as an infusion pump. Delivery of the stimulus can be continuous or intermittent. For intermittent delivery the periods between delivery of the stimulus can either be regular or variable. Delivery of stimuli can be regulated by time or by responding to physiological measurements that are related to the condition being treated, such as air flow measured at the nostrils, chest cavity movement, pulse or brain waves. One or more stimuli can be delivered simultaneously or sequentially during a treatment or regimen. The stimulation appliance can incorporate elements that further enhance interaction of the user with the stimulus. The stimulation appliance elements are aimed to encourage interaction of the user with the stimulation appliance, such as, tongue movement, mouth movement and stimulating swallowing. These stimulation appliance elements can be chewable, lickable, or suckable and configured to fit comfortably in the user's mouth, in proximity to the tongue, such as roller balls, sponges and suckers. The stimulation elements can be smooth or incorporate a texture and have a rigid or soft consistency.

In one variation, the methods and devices described herein are intended to prevent or reduce habituation as a result of applying the stimulant or stimulus. Habituation could eventually lessen the effect of the methods and devices as the individual's response to the stimulus could decrease as a result of repeated application of the stimulus/stimulant.

Accordingly, intermittent delivery of the stimulus/stimulant could produce a greater stimulating effect. In some variations, random or apparently/seemingly random, on/off application of the stimulant/stimulus could improve effectiveness of the methods and/or devices.

The stimulation can be used as a stand-alone therapy or as an adjunct to other sleep disturbance therapies, such as CPAP. For example, a CPAP mask can incorporate a taste or smell stimulation appliance to deliver a regimen that enhances the response to CPAP in users that typically are poor or moderate responders of the CPAP therapy. Using an aerosol of liquid may be introduced with humidification or through separate tubing. This can be continuous or intermittent. Additional modification to the mask can be made to allow for mouth retainer or oral appliance, connected or separate from the CPAP or BiPAP mask that allows for aerosol or fluid to be released into the mouth either continuously or intermittently. To avoid continuous release and potential for habituation to the stimulus, release can be timed to respiration, apnea events or apnea cycles, timed with respirations, respiratory effort, respiratory flow, hypoxia, hypopnea, and or oxygen saturations. Further it can be used as a screening device for assessing tongue obstruction. Since several anatomical components can contribute to a person's degree of obstructive sleep apnea, identifying the causes is paramount in developing a treatment. Using taste stimulation as a non invasive evaluation of the tongue has the potential to better stratify and identify patients that have tongue obstruction as a significant component of their sleep apnea. This is a functional evaluation giving more information than just relative tongue size or position. This could safely and cost effectively screen for more invasive procedures like surgery or implants that reposition or stimulate the tongue.

The stimulation can be delivered through a typical mouthpiece or mask made out of rigid or flexible plastics such acrylic, silicone, EVA, PET, polyethylene, SEBS, polyurethane, polypropylene, PVC material. The device can be manufactured using typical plastics processing methods, such as thermoforming, injection molding, transfer molding, liquid injection molding, overmolding, and the like. The device can be preformed using standard plastic processes and custom fit to the user in a secondary processing step. The stimulant is released in a controlled fashion to increase salivation. In one embodiment, a solution of a taste compound made from Xylitol or saline is placed in the stimulation appliance that comprises a delivery pump. The delivery pump can be programmed to deliver solution in a continuous or intermittent fashion during the sleep cycle. The solution is delivered from the pump to the mouthpiece or mask via connecting tubing while the user is asleep as discussed below. Alternatively, a miniature pump and reservoir can be incorporated within the mouthpiece or mask. The solution is delivered during the sleep period to stimulate swallowing, without causing arousals that awaken the user or elicit an involuntary reflex, such as gagging. For example, the solution can be delivered at rates of (0.01 to 0.2 ml/min). The solution is made up of Xylitol with concentration in the range of 2 to 10 Molar. As a result of the taste compound delivery regimen, the frequency of apneas in a user diagnosed with sleep apnea is reduced 20-40%. The stimulant could also be combined with a texture, for example, a dissolvable flavored sponge that draws the tongue because of taste and tactile sensation. The stimulant could also be a roller, like the roller discussed below, track ball, or other similar structure. In any case, a physical stimulant could be used, alone or in combination with other stimulants, to draw the tongue into a desired position.

Another variation of the methods and devices includes constant or near constant delivery of the stimulant but diluting or adjusting the stimulant so that the response is insufficient to wake the individual. For example, in cases where the stimulant is a taste stimulant, the stimulant can be diluted in a solution where the concentration is held high enough to cause the desired response but low enough to avoid waking the patient and is continuously delivered over a period of time.

The methods described herein are intended for treating sleep disorder breathing in a sleeping individual. In one example the method includes providing a stimulant that induces at least one natural response within a mouth of the sleeping individual when the stimulant enters the mouth; delivering the stimulant at a location behind one or more teeth in the mouth to induce at least one natural response to reduce sleep disorder breathing and improve the ability of the sleeping individual to maintain a sleep state; and intermittently pausing delivery of the stimulant to temporarily cease inducing the at least one natural response, where intermittently pausing delivery prevents the stimulant from waking the individual.

The method can include automatically delivering the stimulant from a supply source while the individual is in a sleep state. The natural response can comprise an activity selected from the group consisting of salivation, forward movement of the tongue, repositioning of the tongue, swallowing and a combination thereof. At least one of the activities described herein can optionally reduce vibrations of a soft palate or uvula without waking the individual.

The oral appliance can be a mandibular advancement device, a custom molded mouthpiece, a continuous positive airway pressure device, a mouthguard, and a retainer.

In some variations, the oral appliance comprises an internal reservoir fluidly coupled to the delivery port, the internal reservoir containing at least a portion of the stimulant, and where the delivery port comprises a valve, where providing the stimulant comprises opening of the valve to dispense the stimulant. Alternatively, or in combination, the device can include an external reservoir containing the stimulant.

The stimulant can also trigger an olfactory response in the individual. Alternatively, or in combination, the devices and methods can include a second stimulant to trigger an olfactory response in the sleeping individual.

In some variations, intermittently pausing delivery of the stimulant comprises pausing the stimulant until a triggering signal restarts delivery of the stimulant. Additionally, the devices and methods can include a dispensing unit in electrical communication with a sensor, where the triggering signal is generated in response to the sensor.

Sensors can include a pressure sensor, an optical sensor, a sound sensor, a movement sensor, an electro-magnetic sensor. In one variation, the sensor is positioned in the mouth and generates a signal based on a movement/position of the tongue, or a position/movement of a jaw. Furthermore, the amount of stimulant delivered can be determined by the triggering signal. For instance the method and/or device can measure a degree of tongue movement with the sensor and use the triggering signal to determine the amount of stimulant based on the degree of movement.

In another variation, delivering the stimulant and intermittently pausing delivery of the stimulant are timed with an event selected from a group consisting of respiration, respiratory effect, respiratory flow, hypoxia, hypopnea, oxygen saturation, pausing the stimulant until a triggering signal restarts delivery of the stimulant.

Another variation of the method includes a method for minimizing sleep disturbances in an individual during a state of sleep. In one example, such a method includes positioning a dispensing unit within a mouth of the individual, where the dispensing unit comprises at least one port adjacent to a tongue; providing a supply of a stimulant through the port that induces a biological response in the mouth of the individual when the stimulant contacts an anterior surface of the tongue; controlling delivery of the stimulant between a delivery phase, in which the stimulant is delivered to the mouth to induce the biological response and a dwell phase, during which delivery of the stimulant to the mouth is stopped, where controlling delivery of the stimulant permits periodically inducing the biological response without waking the individual.

In another variation, the present disclosure includes an oral device for dispensing a stimulant that produces a biological response within the mouth to reduce incidents sleep disorder breathing in an individual. Such a device can include a device body having a dental cavity for removably nesting with one or more structures within the mouth; a dispensing port adjacent to an anterior portion of the dental cavity, such that when the device body is positioned within a mouth the dental cavity is adjacent to the teeth and the dispensing port is adjacent to a posterior surface of teeth such that the stimulant leaving the dispensing port draws the tongue adjacent or next to the posterior surface of the teeth; a fluid reservoir fluidly coupled to the dispensing port being configured to maintain a supply of the stimulant; a valve located in a fluid path between the fluid reservoir and the dispensing port where the valve allows for intermittent dispensing of the stimulant through the dispensing port. Regardless of location of placement, the valve allows for metering or preferential dispensing of the stimulant.

A variation of the oral device can further include a palatial nesting section adjacent to the dental cavity and configured to nest within an arch of a palate to improve retention of the device body within the mouth.

In alternative embodiments, stimulants can be made in the form of capsules or films that dissolve over time. The capsule or film may be configured such that it gives enough time for the patient to fall asleep before the stimulant starts to come out of the capsule. The capsule can be incorporated into a stimulus appliance that the patient wears, such as mouthpiece, at night. As the patient falls asleep, the capsule starts to dissolve in the mouth and the taste compound starts to leach out of the capsule causing the patient to salivate more.

The capsule may incorporate multiple alternating layers of the taste compound and tasteless transition layers so that intermittent delivery of the taste is accomplished as the alternating layers dissolve.

Another variation of an oral device according to the principles disclosed herein includes a device for producing a biological response within the mouth to reduce sleep disorder breathing having a device body having a dental cavity for removably nesting with one or more structures within the mouth; and a dispensing surface adjacent to an anterior portion of the dental cavity, such that when the device body is positioned within a mouth the dental cavity is adjacent to the teeth and the dispensing surface is adjacent to a posterior surface of the teeth, where the dispensing surface comprises a supply of a stimulant, where the stimulant is releasable from the dispensing surface over a period of time and draws a tongue adjacent to or next to the posterior surface of the teeth. Such a device can include the stimulants described herein that are deposited as coatings on or into the dispensing surface via a process such as UV-linking, solvent-based deposition, or any such commercially available procedure.

Some benefits of the present devices, systems and methods include safety and comfort, increases muscle tone of the upper airway, the ability to distribute in an over-the-counter fashion; reduced cost as compared to many of the existing remedies and over-the-counter sleep therapy modalities; ease of use; reversible nature of the produce; non-invasive. Additional benefits include the ability for the tongue to move freely and to allow for swallowing. Other possible uses for the devices and methods described herein include treatments for oral hygiene, xerostomia, nocturnal bruxism, and/or nocturnal gastroesophogeal reflux.

BRIEF DESCRIPTION OF THE SEVERAL VIEWS OF THE DRAWING(S)

FIG. 8B shows a chart for an apnea-hypopnea index (AHI) results for individuals with mild to moderate OSA, while FIG. 8B presents the apnea-hypopnea index (AHI) results for individuals with severe OSA.

Figure 11:
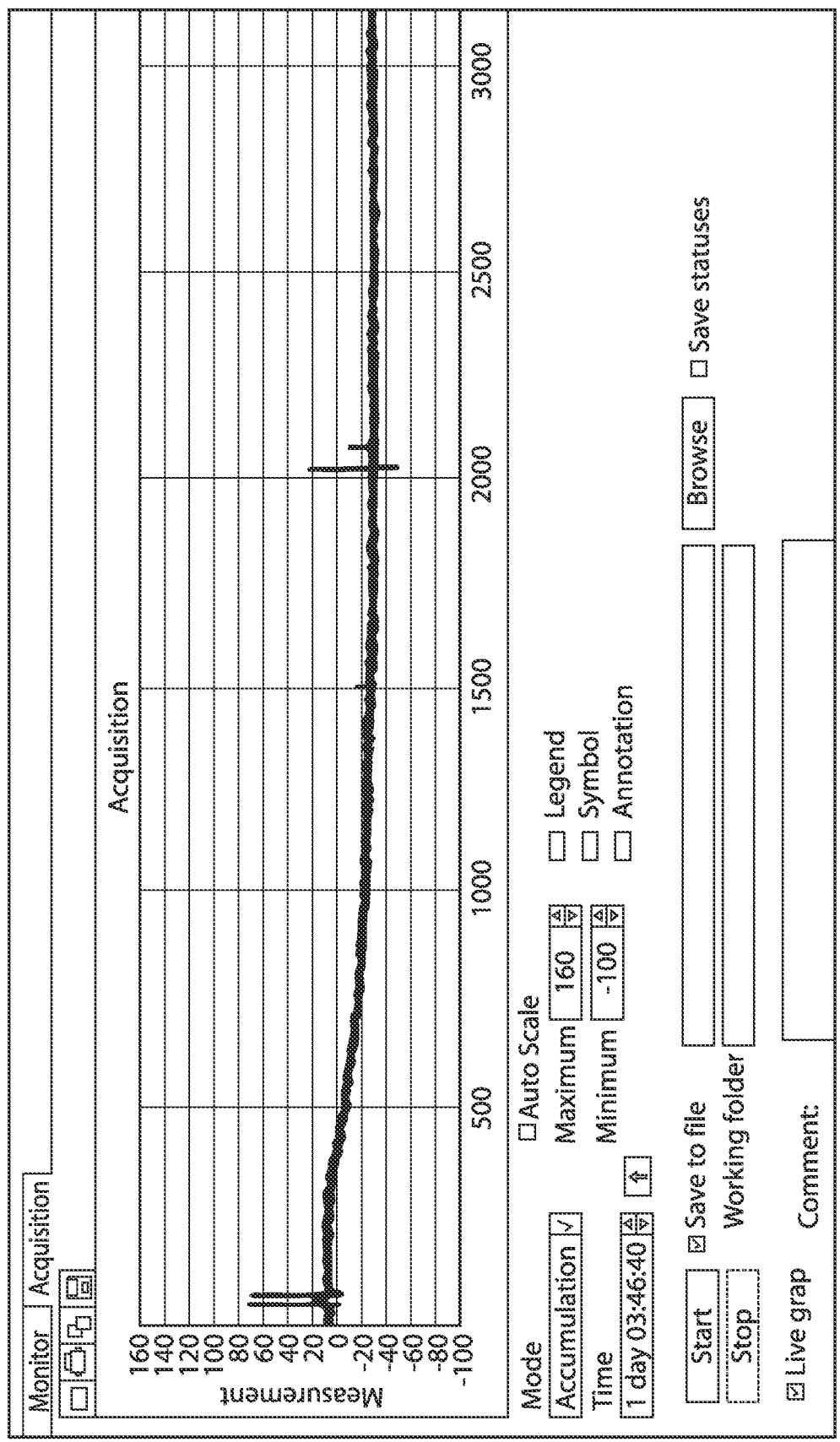

FIG. 11 also shows another graph of other sensed anterior tongue pressure that was recorded vs. time, also under the experimental study of Example 2, but according to another example showing a period of OFF delivery condition only.

Figure 12:
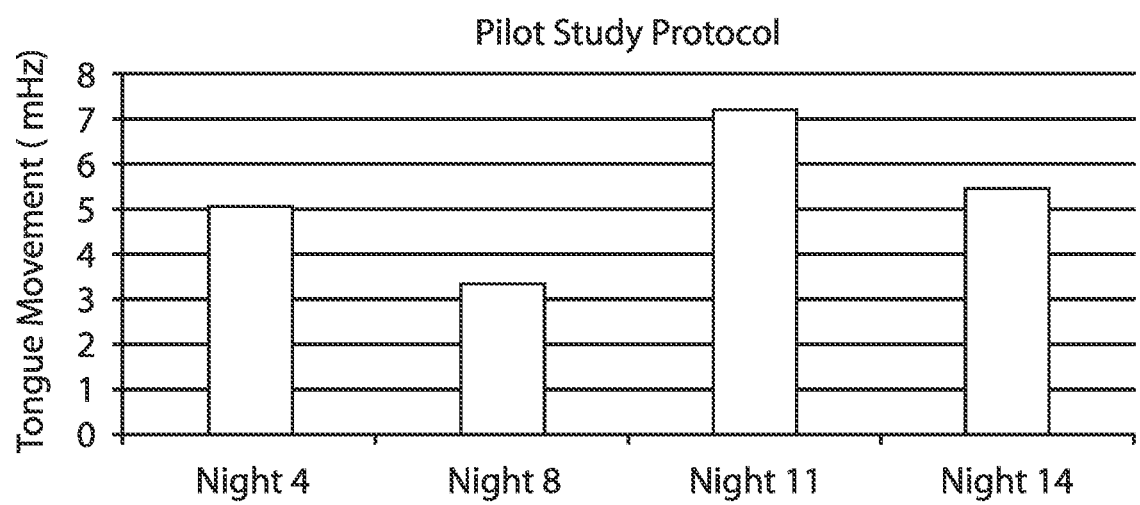

FIG. 12 shows another bar graph of frequency of sensed anterior protective tongue positioning events (per second) vs. time (consecutive nights over 14 day period), also according to the Example 2 experimental protocol, but according to another aspect of the study observing results of using the same stimulus delivery rates and intervals on four separate nights throughout the 14 day trial.

Figure 13:
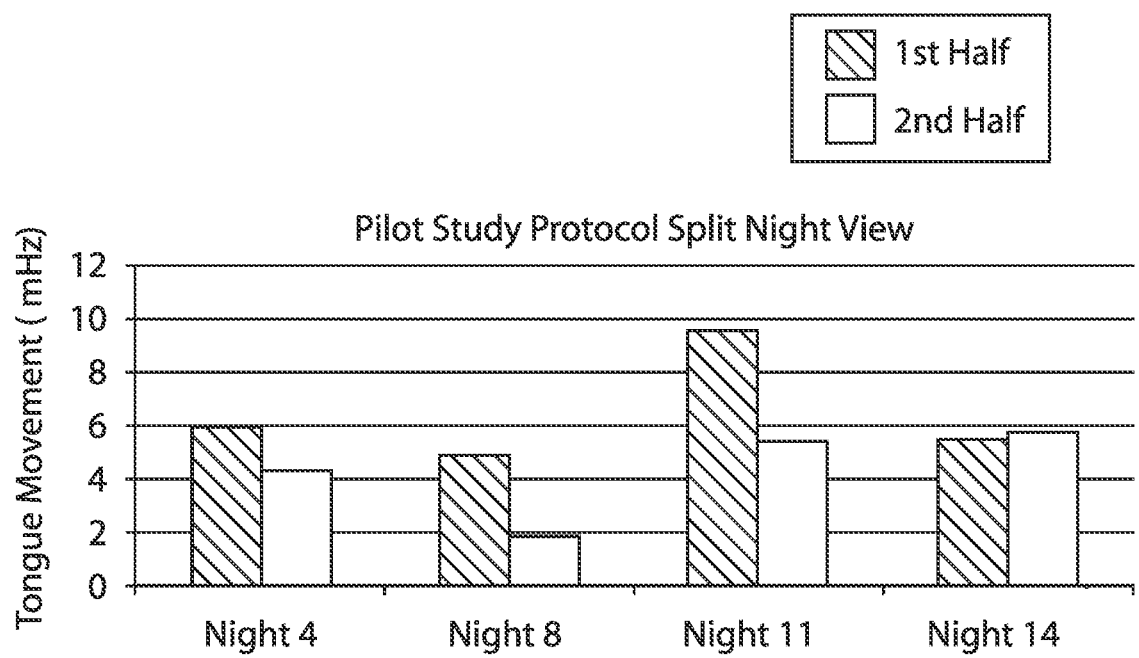

FIG. 13 shows a bar graph of the same results featured in FIG. 12, per frequency of sensed anterior tongue positioning events (per second) vs. time (consecutive nights over the 14 day period, in split-night view), but showing comparison results between the first half and the second half of the nights featured in the graph (i.e. "split night" view or analysis).

Figure 14:
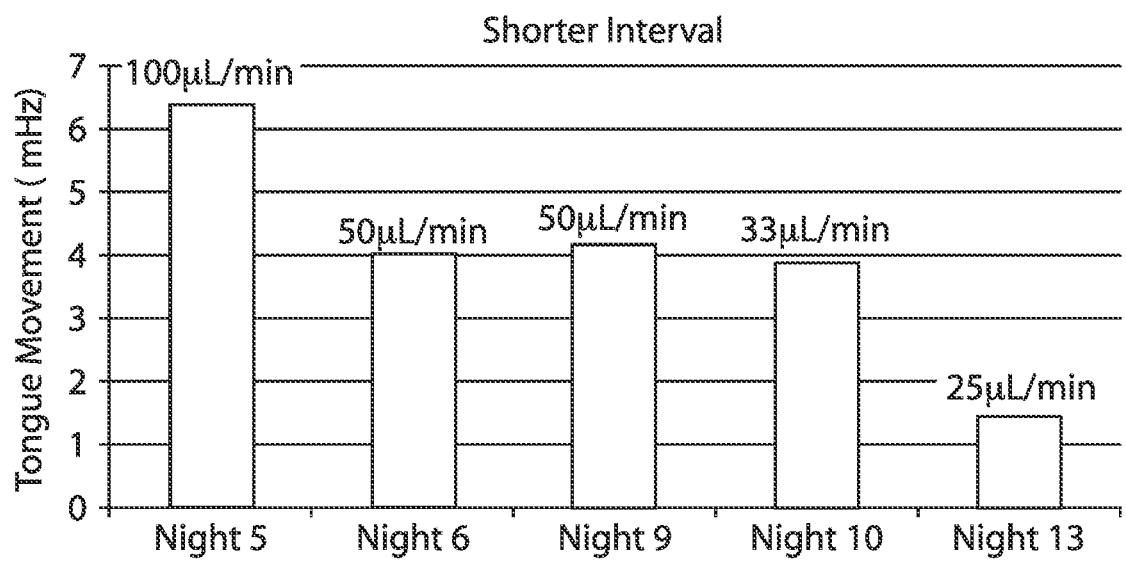

FIG. 14 shows another bar graph of experimental results of Example 2 according to frequency of sensed anterior protective tongue repositioning events (per second) vs. time (consecutive nights over 14 day period), but showing results of using a shorter interval than the pilot trial protocol with various rates.

Figure 15:
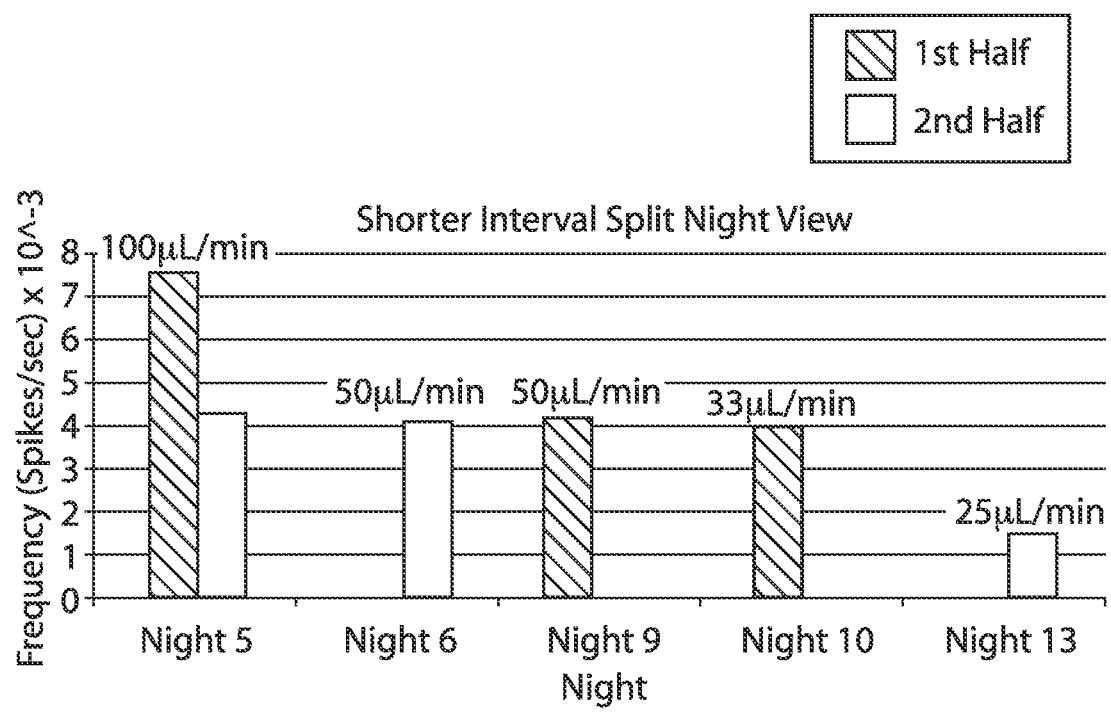

FIG. 15 also shows a bar graph of the same results per frequency of sensed anterior protective tongue repositioning activity events (per second) vs. time (consecutive nights over 14 day period) shown in FIG. 14, but shows comparison results between the first half and the second half (when available) of the nights in split night analysis.

Figure 16:
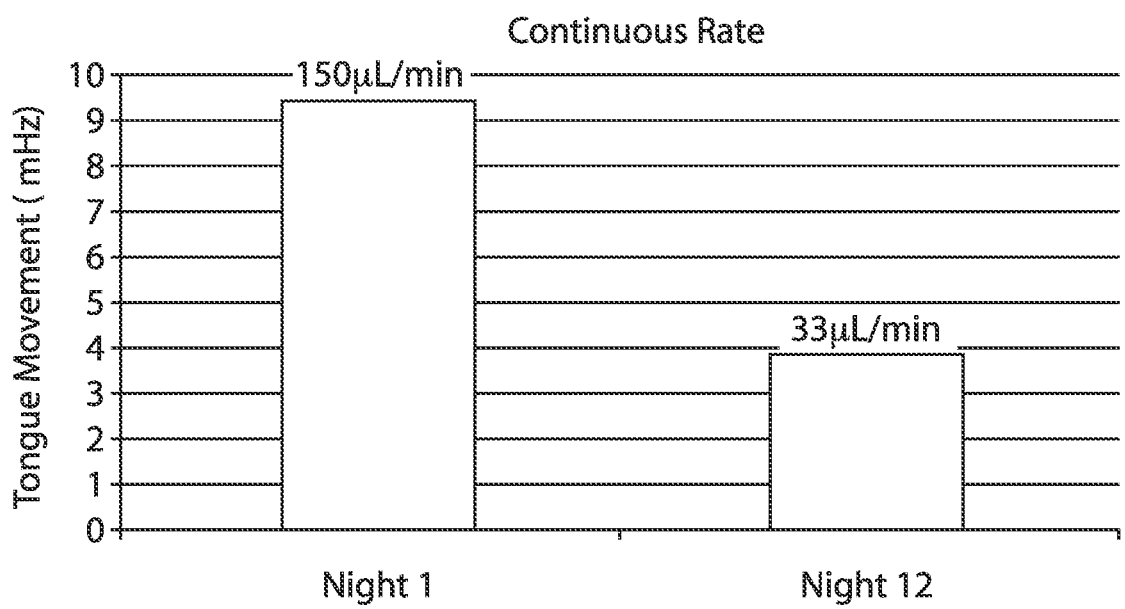

FIG. 16 also shows a bar graph of frequency of sensed anterior protective tongue repositioning activity events (per second) vs. time (consecutive nights over 14 day period) but shows results of another sub-protocol during continuous flow, with no pauses in delivery of xylitol, but comparing two different stimulant delivery rates.

Figure 17:
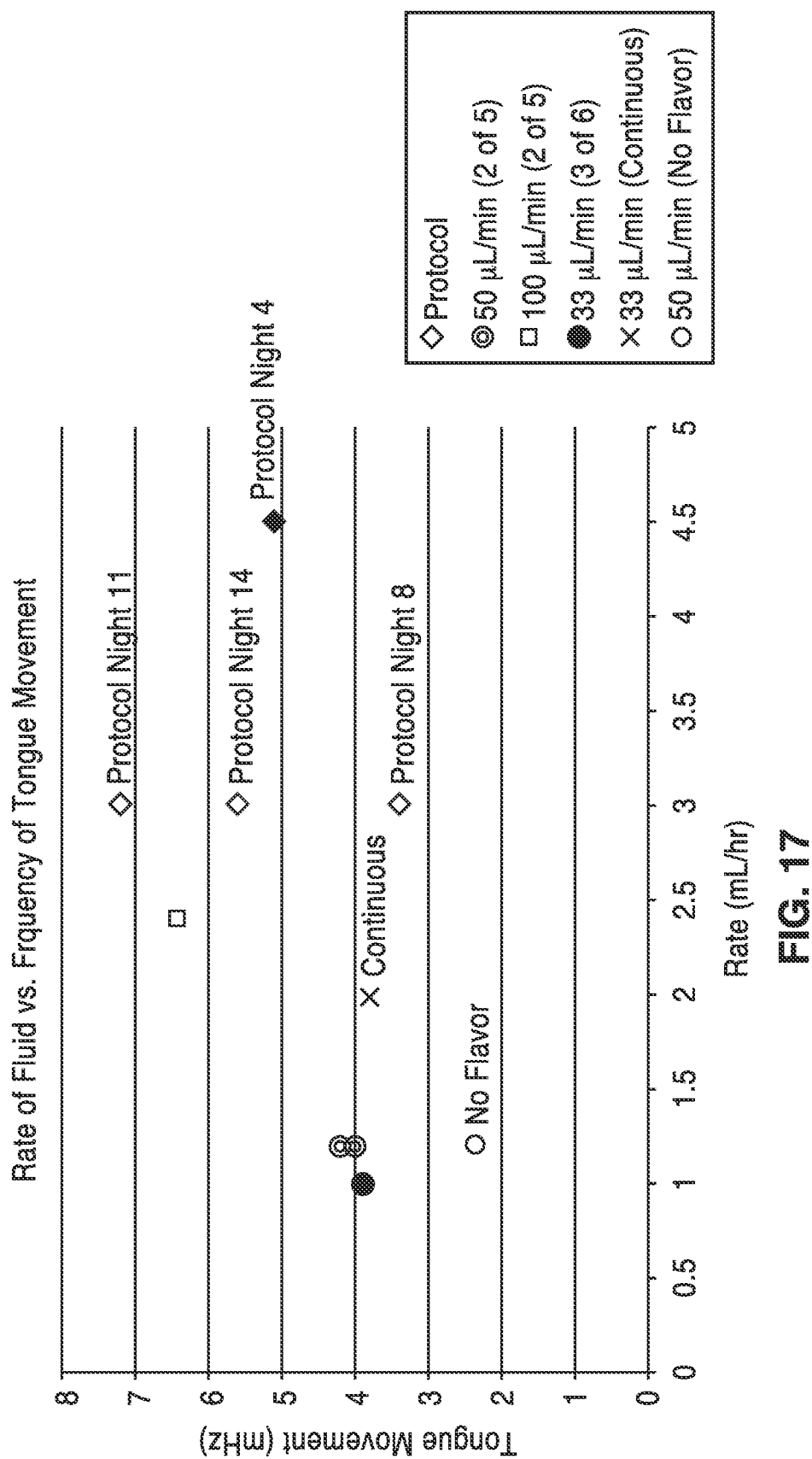

FIG. 17 shows an x-y plot of sensed tongue movement to the protective anterior position as a function of varying stimulant delivery rates over the experimental design of Example 2.

Figure 18:
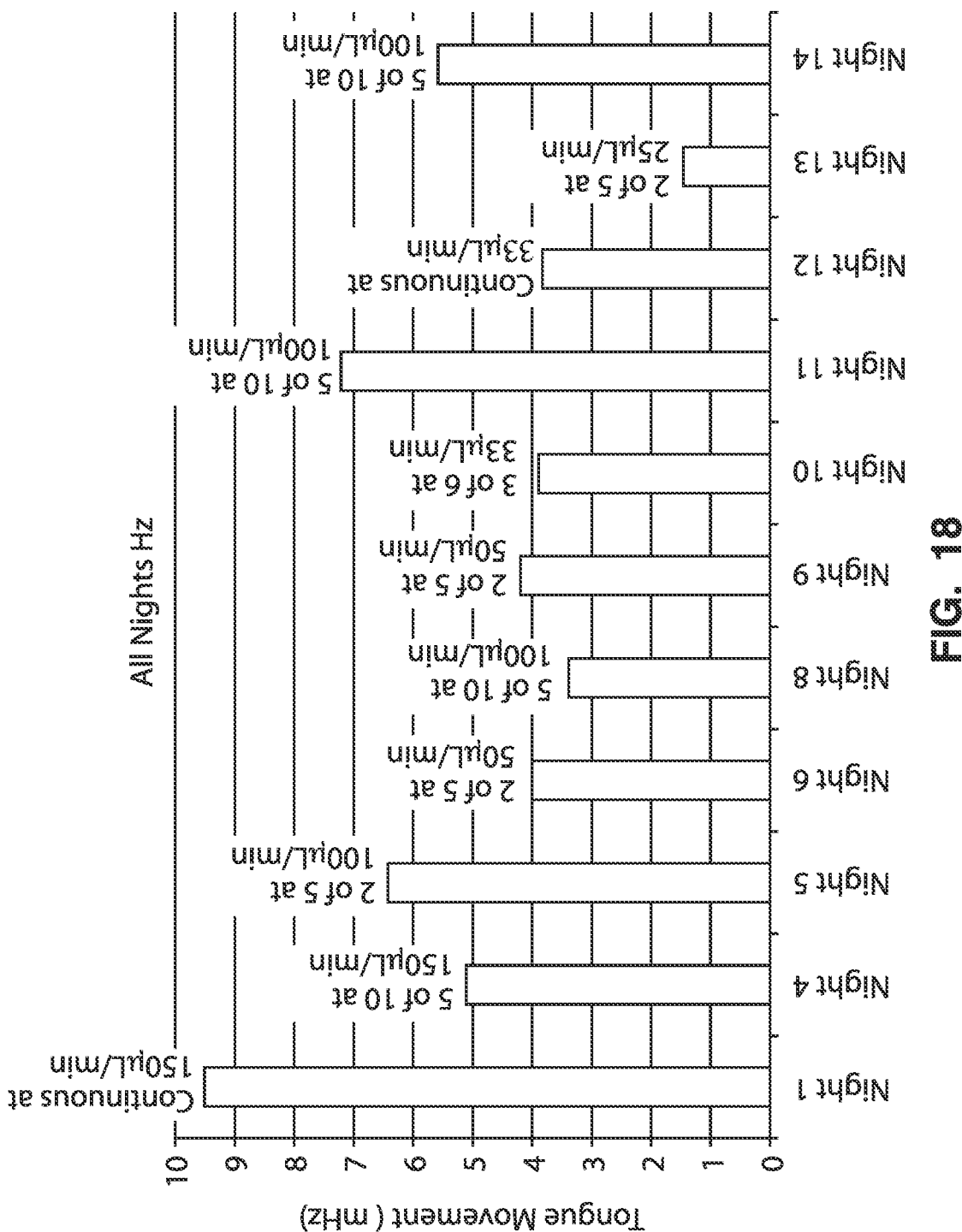

FIG. 18 also shows another bar graph reflecting sensed anterior tongue repositioning events over the 14 days of consecutive treatment at various rates and protocols of the Example 2 experiment.

DETAILED DESCRIPTION OF THE INVENTION

The methods, devices and systems described herein reduce or eliminate snoring and/or episodes of sleep apnea and optionally allow for minimal physical intervention.

Figure 1:
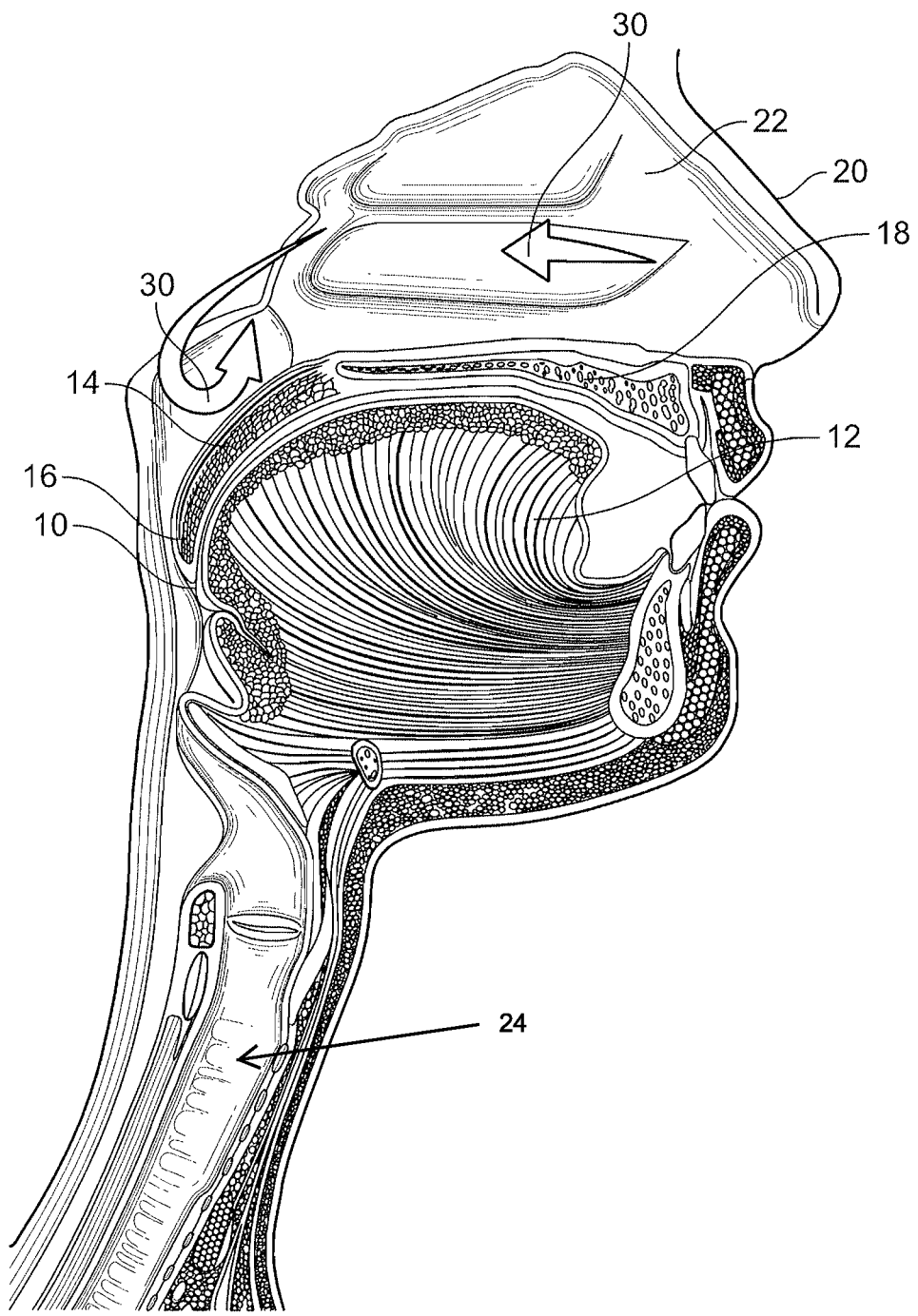
FIG. 1 depicts a cross sectional view of the upper respiratory tract in a patient having a blocked airway.

FIG. 1 depicts a cross sectional view of the upper respiratory tract in a patient having a blocked airway 10. As discussed above, snoring occurs as a result of vibration of the soft palate 14 and uvula 16 that are located at the end of the hard palate 18. As illustrated, the tongue 12 is moved from its rest position in a rearward direction causing impingement of the airway 10 by the rear portion of the tongue 12 against the uvula 16. As a result, the blockage prevents air, whether breathed through the mouth or nose 20, from passing through the airway 10 and ultimately into the throat 24. As shown by arrows 30, the abnormal position of the tongue 12 prevents passage of air in the nasal cavity 22. As noted above, this situation leaves a space for the passage of air between the hard palate and the top of the tongue and over the soft palate. The passage of air over the soft palate can cause vibrations which are the source behind the snoring sound as well as contribute to sleep apnea.

The devices, methods, and systems described herein can ameliorate or prevent snoring and/or blockage of the airway 10 leading to improved sleep quality in an individual. Such devices, methods and system deliver one or more stimuli to the sleeping individual to induce a natural or biological response within the body that lessens snoring and/or opens the airway to minimize the incidence of apnea. In most variations of the devices, methods and systems, the stimuli (or the delivery rate of the stimuli) should induce the natural response at an effective level that does not wake the individual. However, alternate variations may include delivering the stimuli with the intent to wake the individual.

Figure 2A:
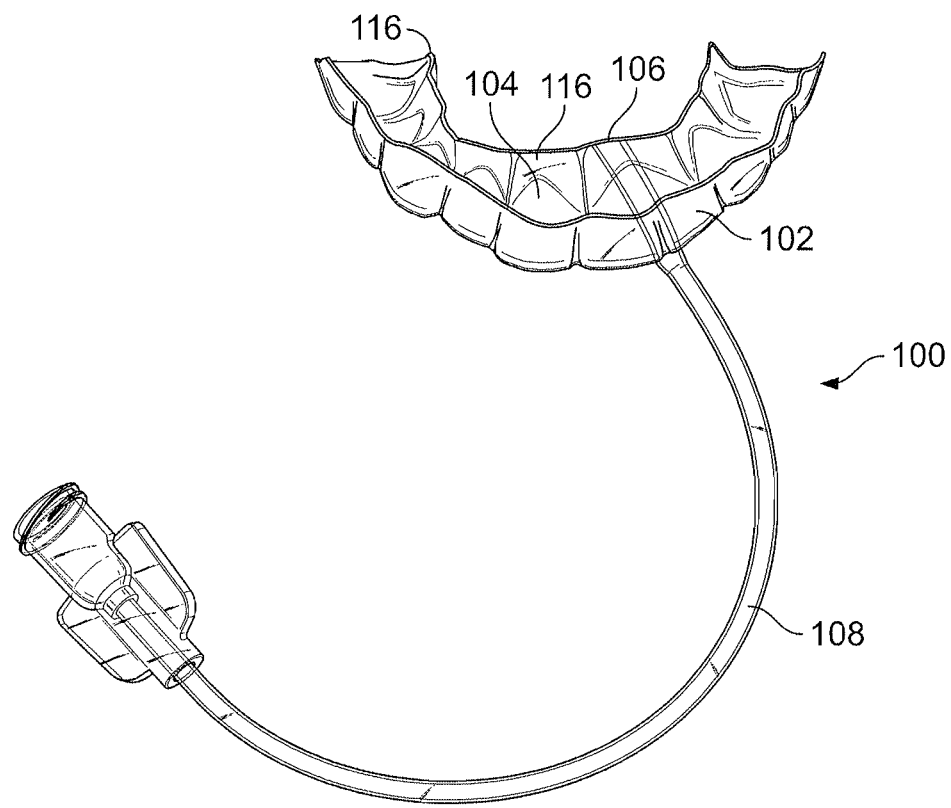
FIGS. 2A and 2B illustrate variations of an oral device that can be used to induce a biological response within a mouth of an individual to reduce the frequency or prevent snoring and/or sleep apnea.

FIG. 2A illustrates one variation of an oral device 100 that can be used to induce a biological response within a mouth of an individual to reduce the frequency or prevent snoring and/or sleep apnea. In this variation, the oral device 100 includes a device body 102 having a dental cavity 104 for nesting the device on one or more teeth of the individual. While the illustrated variation shows the device body 102 having a dental cavity 104 that accommodates a number of teeth, variations of the device 100 include a dental cavity 104 that is suited for nesting the device 100 on one or more teeth. Alternate variations can include oral devices 100 that nest directly on the palate, gums, or beneath the tongue. Accordingly, such variations need not include a dental cavity.

The illustrated oral device 100 also includes a dispensing port 106 that can be used to deliver a stimulant to the oral cavity, mouth and/or tongue. In this variation, the port 106 is coupled to a supply of the stimulus via a tube 108 that forms a part of a fluid path between the supply or reservoir of the stimulus and the port 106. The tube 108 includes a fitting to allow for coupling to an external reservoir. As described in further detail below, a valve (shown in FIG. 2B) is located between the port 106 and the reservoir. The valve allows for intermittent dispensing of the stimulant through the dispensing port 106. In some cases a valve is not required. Instead, the device uses a pressure differential to drive the stimulant through the port.

Figure 2B:
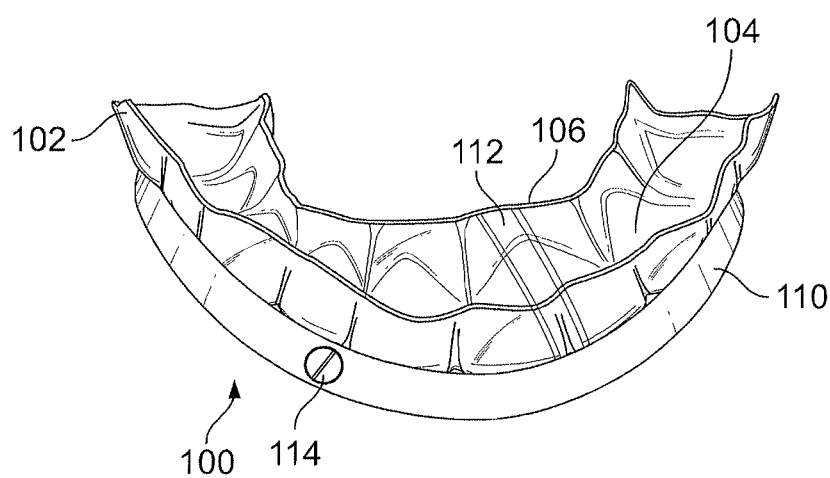

FIG. 2B illustrates another variation of an oral device 100 for use as described herein. In this variation the device 100 also includes a dispensing port 106 used to deliver a stimulant to the oral cavity, mouth and/or tongue. However, in this variation, the port 106 is coupled to a supply or reservoir 110 that is directly coupled to a body 102 of oral device 100. The reservoir 110 is in fluid communication with the port 106 such that a fluid path is formed therebetween. FIG. 2B also shows a valve 112 located adjacent to the port 106 where the valve allows for intermittent dispensing of the stimulant through the dispensing port 106. In alternative variations, the valve can be placed anywhere in or around the lumen or fluid path. This variation of the device 100 is a wholly self contained oral device that can rely on internal circuitry to dispense the stimulant and/or rely on an external unit (not shown) that can wirelessly transmit a triggering signal to the valve 112 to dispense the stimulant. The dispensing conditions and frequency are described below. The variation of the oral device 100 shown in FIG. 2B can be disposable after depletion of the stimulus or can have a second refill valve 114 to permit the user to replenish the stimulant as required.

Figure 3A:
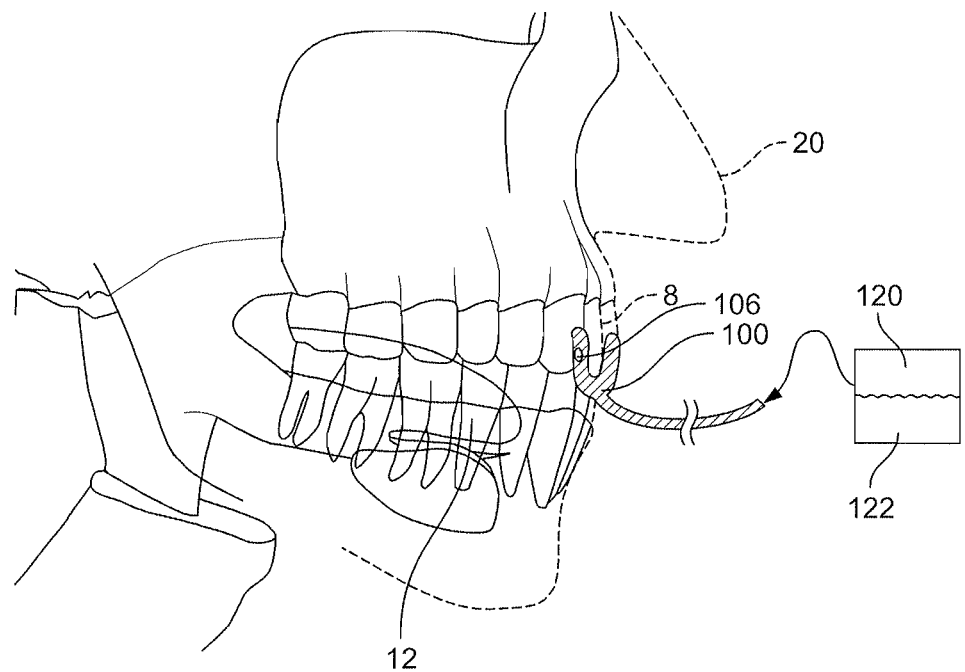
FIGS. 3A and 3B show phantom views of the oral cavity to illustrate examples of positioning an oral device within a mouth.
Figure 3B:
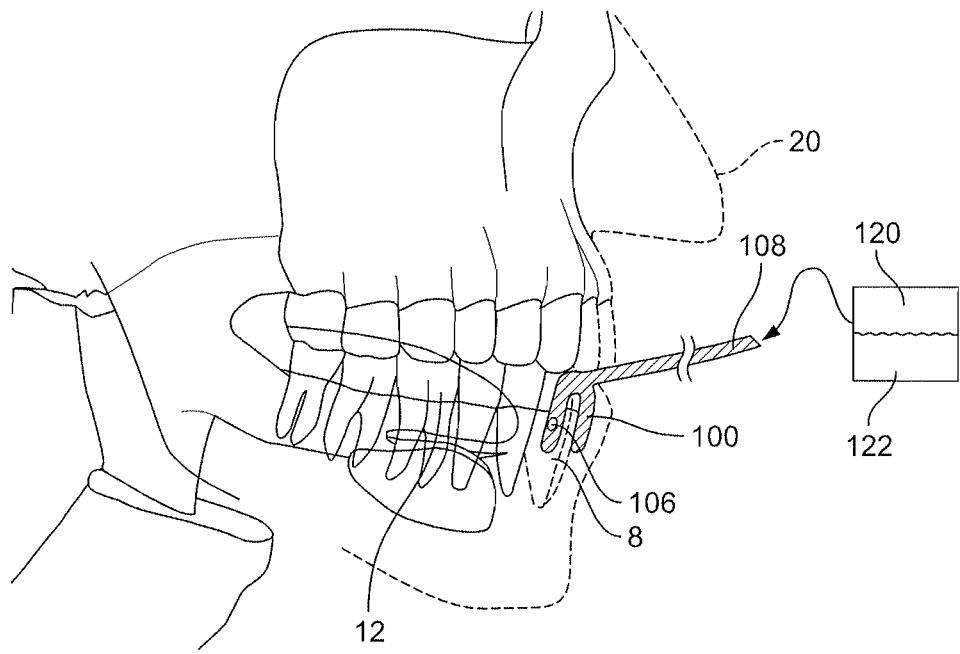

FIGS. 3A and 3B show phantom views of the oral cavity to illustrate some examples of positioning one or more oral devices 100 can be placed to produce the natural response that reduces snoring and/or sleep apnea. As illustrated, the oral device 100 can be positioned or nested to one or more teeth 8. In alternate variations, the device 100 can be nested or temporarily affixed to gums, a palate, or other structure within the mouth. FIG. 3A shows nesting of the device 100 on the top front teeth 8 while FIG. 3B illustrates nesting of the device 100 on the bottom front teeth 8. However, alternate devices 100 permits removable nesting of the device with one or more structures within the mouth, including the side teeth, or other structures within the mouth. Additionally, the dispensing port 106 can be positioned anywhere on the device. However, the illustrated variation shows a dispensing port 106 adjacent to an anterior portion of the dental cavity or device body. With this positioning the dental cavity is adjacent to the teeth. Such positioning allows the dispensing port 106 to deliver the stimulant 122 and draw the tongue 12 to a desired position in the mouth. FIGS. 3A and 3B illustrate oral devices 100 that are coupled to external reservoirs 120 that can optionally include one or more controllers or other dispensing unit to control the delivery of the stimulant 122 to the device 100. As noted above, variations of the system include reservoirs that are fabricated directly onto a body of the device 100. In such cases, the dispensing unit/controller can be positioned on the device 100 body or can be external to the device 100 such that a triggering signal is provided via wired or wireless communication.

Figure 3C:
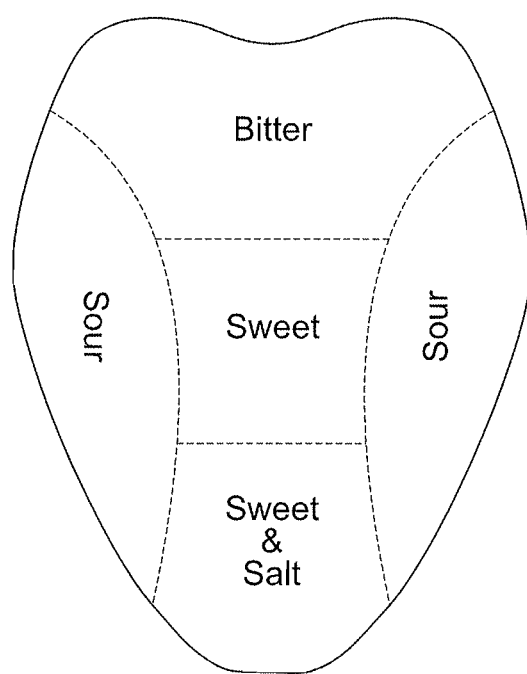
FIG. 3C shows a schematic of taste regions on a tongue.

In addition to the above, variations of the devices described herein or used in procedures described herein can position one or more ports adjacent to specific taste receptors on the tongue. For example, FIG. 3C illustrates a schematic view of a tongue to demonstrate the various regions of taste. Typically, the port 106 is positioned adjacent to the "sweet & salt" taste receptors that are positioned on an apex of the tongue. However, ports can be additionally, or alternatively, positioned to target "sour", "sweet", or even bitter taste receptors.

Figure 4A:
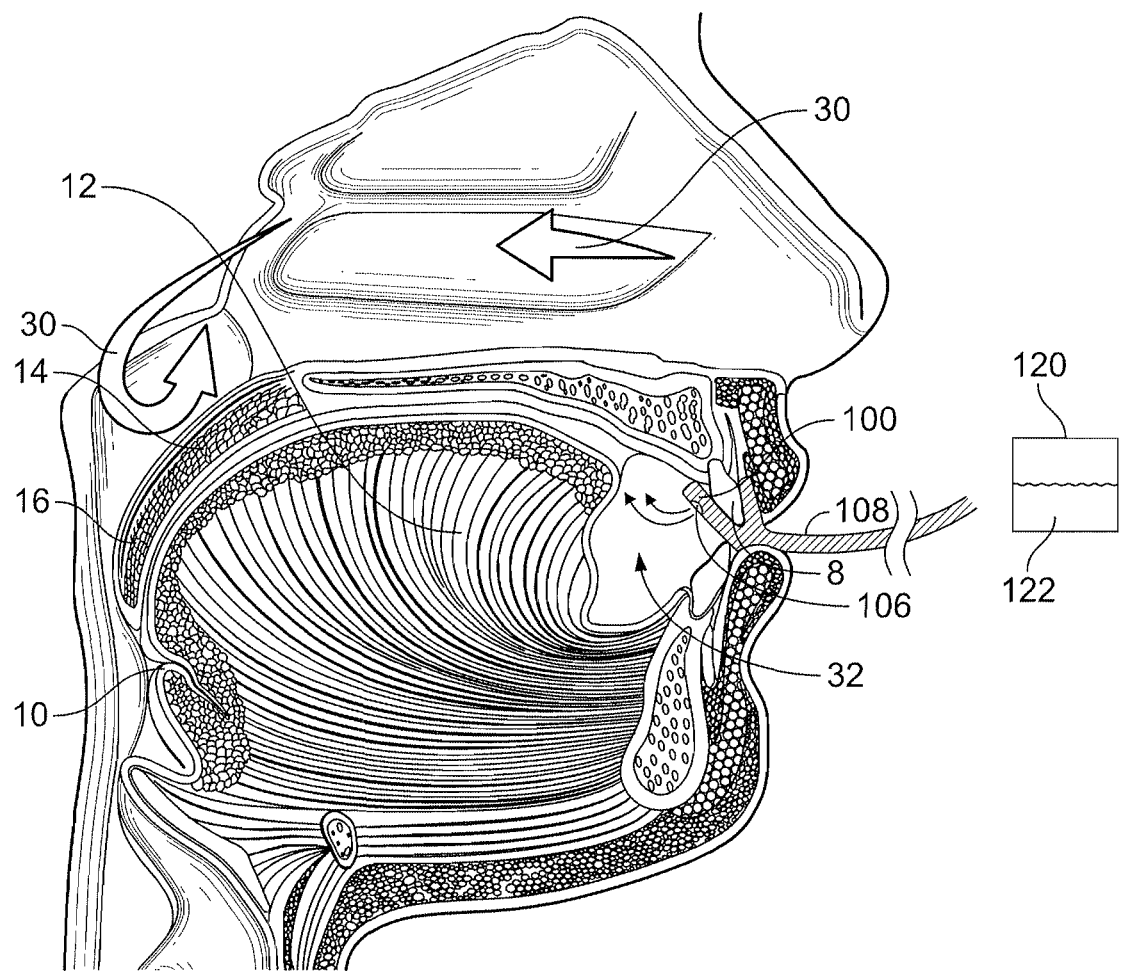
FIGS. 4A and 4B illustrate a condition immediately prior to contemporaneous to dispensing a stimulant where an individual is sleeping and the tongue is in a retracted position causing restriction of the airway and inability of air to pass through the upper respiratory tract.
Figure 4B:
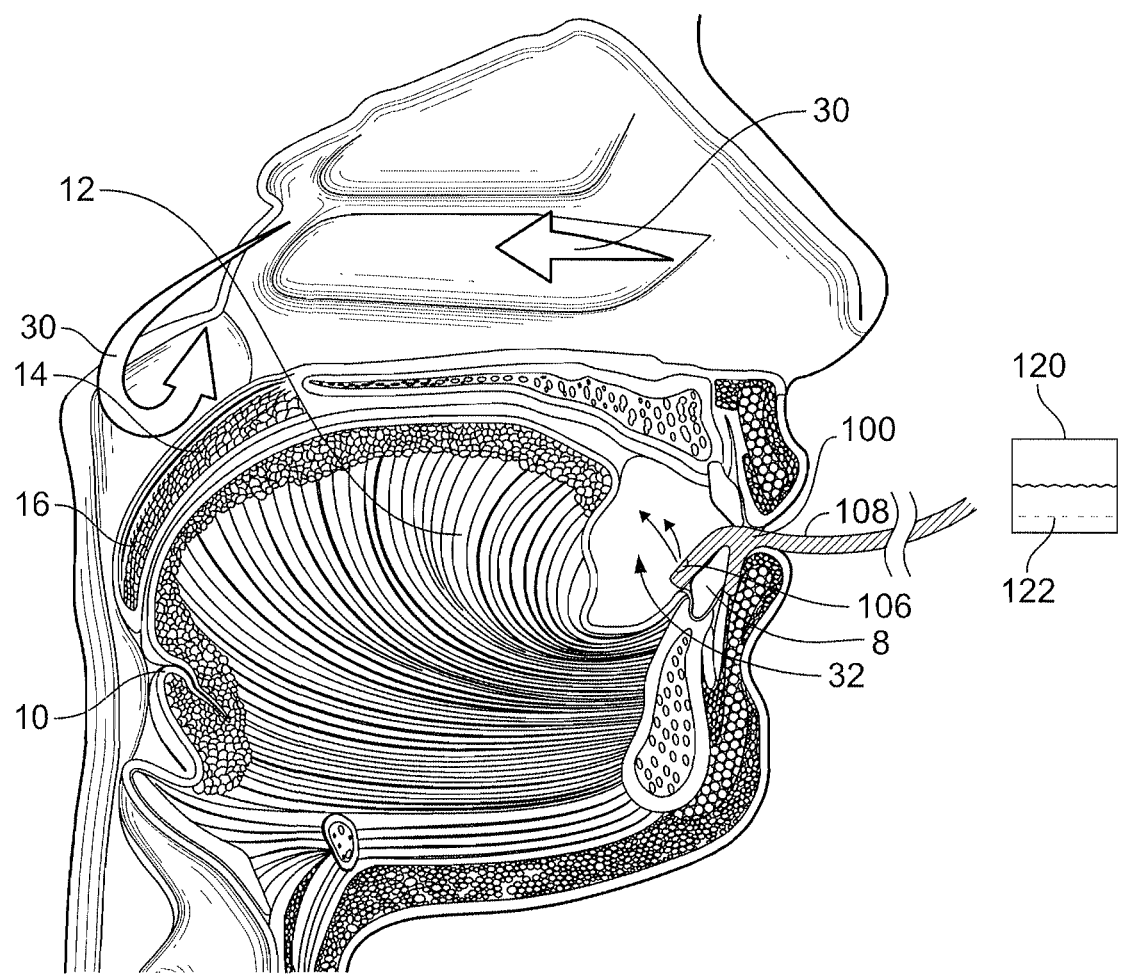

FIGS. 4A and 4B illustrate a condition as described above where an individual is sleeping and the tongue 12 is in a retracted position causing restriction of the airway 10 and inability of air as denoted by arrow 30 to pass through the upper respiratory tract. In this variation, the individual previously inserted a variation of an oral implant 100 within the mouth. Again, this variation of the oral implant 100 is nested on one or more teeth 8 of the individual. FIG. 4A shows nesting of the implant 100 on the top teeth while FIG. 4B shows nesting of the implant 100 on the bottom teeth. Again, additional variations allow for temporary positioning anywhere that allows for the stimulant to induce a natural or biological response.

The device 100 is coupled to a reservoir 120 containing a supply of the stimulant 122. In one variation, the stimulant is delivered intermittently. Alternatively, or in combination delivery of the stimulant produces the biological response only when necessary. This intermittent delivery reduces the probability of waking the individual. The intermittent delivery also serves to minimize the chances of the individual becoming desensitized to the stimulant. Delivery of the stimulant can be intermittently paused based on any number of conditions. For example, delivery or pausing delivery of the stimulant can be time based, or can be based on sensor feedback as described below. Once delivery of the stimulant occurs, as shown by arrows 32, the port 106 delivers the stimulant to a desired area within the mouth (e.g., a surface of the tongue, underneath the tongue, etc.).

Delivery of the stimulant produces a natural response such as salivation, forward movement of the tongue, repositioning of the tongue, swallowing or a combination thereof.

Figure 4C:
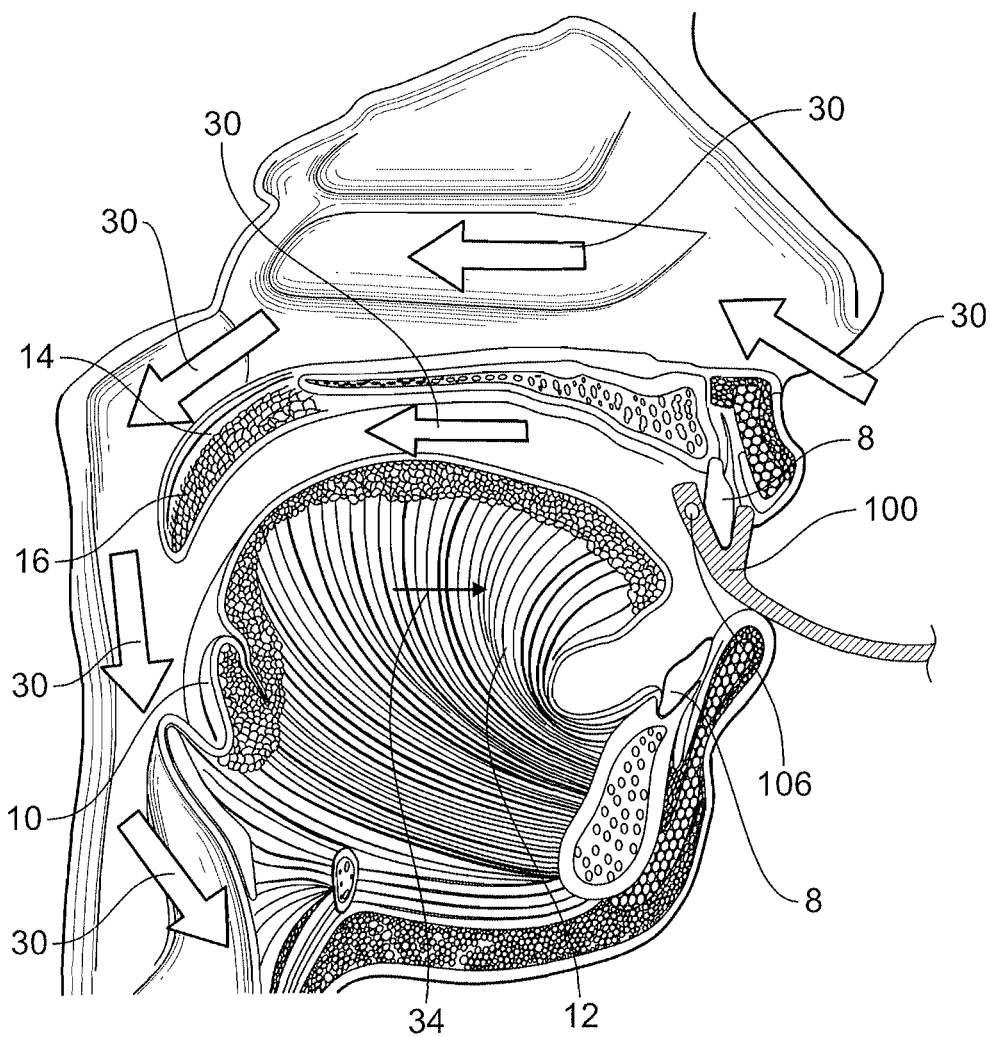
FIG. 4C shows one effect of the disbursed stimulant of FIG. 4A.

FIG. 4C illustrates the effect of these natural response induced by the stimulant. As shown, the tongue tends to reposition (as shown by arrow 34). Any one of the natural responses or a combination thereof causes opening of the previously constricted airway 10. This natural response re-establishes airflow as shown by arrows 30 in FIG. 4C. As a result, air can pass through the airway 10 to the lungs.

The biological response, in particular inducing saliva generation in the mouth allows for pooling of saliva in the mouth, leading the patient to swallow. The increased frequency of swallowing action increases the muscle tone of the airway muscles. As the patient swallow, the patient stops snoring and the upper airway obstruction clears.

The concepts and features described herein can be employed in any number of devices. In certain variations, the devices include those devices that fit within a mouth of the individual. For example, such oral appliance can include mandibular advancement devices, a continuous positive airway pressure device, a mouthguard, or a retainer.

Figure 5A:
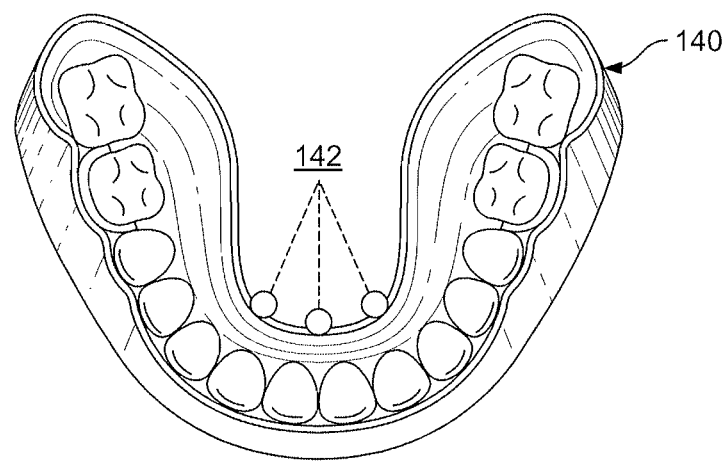
FIGS. 5A and 5B illustrate one example of a mandibular advancement device (MAD) coupled to one or more sensors.
Figure 5B:
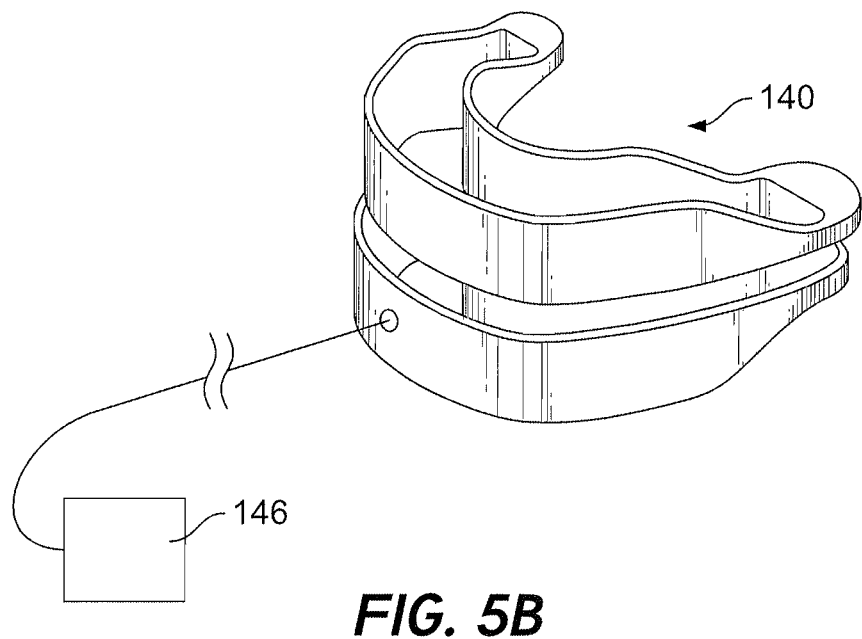

FIGS. 5A and 5B illustrate one example of a mandibular advancement device (MAD) 140 coupled to one or more sensors. Such sensors can include a pressure sensor, an optical sensor, a sound sensor, a movement sensor, an electro-magnetic sensor, or any sensor that can detect a condition requiring delivery of the stimulant. For example, FIG. 5A shows a number of sensors 142 positioned on an interior of the device 140. The sensors can be coupled to a controller 146 (either via a wireless or a wired connection) so that the sensor detects a pre-determined condition. When the condition is triggered, the controller 146 and/or sensor can produce a triggering signal to either start or stop delivery of the stimulant. The sensor can be independent of the device 140 or can be positioned outside of the body. Sensors for use with the devices and methods described herein can be used to generate a signal based on a movement or position of the tongue, measuring a degree of tongue movement with the sensor and using the triggering signal to determine the amount of stimulant based on the degree of movement. Alternatively, or in combination, a triggering signal can be timed with an event such as respiration, rate of respiration, a respiratory effect (e.g., wheezing or coughing), respiratory flow, hypoxia, hypopnea, oxygen saturation, etc.

The position or force applied to a MAD can be used as a means to trigger delivery of the chemoattractant stimulant. Mandibular advancement devices are used to effectively treat snoring and OSA symptoms. The MAD functions by maintaining the lower jaw in a prescribed position by creating forward movement of the lower jaw with respect to the upper jaw. This forward movement also creates space in the airway to relieve symptoms. Conversely, in the absence of the lower jaw constraint relative to the upper jaw, the potential airway space narrows with concomitant return of symptoms. This lower jaw motion can correlate to the sleep state of the patient and therefore can be used as a trigger to deliver the stimulant during periods of sleep when snoring and OSA symptoms are occurring. Accordingly, a mandibular advancement device can be configured to sense the relative position or force of the lower component of the MAD with respect to the upper component and the resultant change in position or force used to trigger delivery of the stimulant. Alternatively or in combination, the delivery of stimulant can be simply activated when a threshold relative motion or force is reached. In another variation, the amount of relative motion or force can be used to proportionately adjust the dosing of the stimulant in the period that the motion or force is measured.

The device can optionally include design features that have limited intrusion into the mouth yet able to maximize the surface area of the tongue in contact with the device. For example, a person resting in a supine position will often have increase tongue obstruction due to gravity. This is demonstrated by the example of a sleeping person who improves or eliminates their snoring by rolling onto their side. An ideal contact with the tongue in the supine position is along the bottom teeth. In this position the tongue is resting on the floor of the mouth and bottom teeth. Delivery of the stimulant onto the lower teeth can increase the muscle tone of the tongue. This increased tone of the tongue is intended to match to that of a person that does not suffer from snoring or obstructive sleep apnea.

The device can have the form similar to that of a retainer that is worn at night on the lower teeth. The retainer can be fitted with a port or ports along the lingual side of the lower teeth. The port(s) can be connected to a reservoir of stimulant discussed herein. Alternatively the flavored compound can line the retainer along the aspect of the retainer that is along the tongue. By placing the retainer and flavors along the lower teeth, towards the back of the lower jaw, mandibular dental arch, there is the additional advantage of stimulating the posterior portion of the tongue. The glossopharyngeal nerve innervates that posterior (back) one-third part of the tongue. Along with the Vagus nerve that senses taste from the tongue, position and movement can be measured by using a fiber optic sensor. For example, sensors commercially available from FISO Technologies, Inc. Quebec, Canada suffice. The sensors have dimensions and mechanical properties that enable the sensors to be positioned in the mouth to obtain tongue position and tongue movement information without disrupting the user in an awake or sleep state. The sensor can be positioned in the mouth to obtain information relative to the location of the sensor. More than one sensor can be positioned in the mouth to obtain measurements either simultaneously or sequentially. For example a pressure sensor can be incorporated into the mouthpiece as described in the referenced provisional application. The amount of pressure exerted by the tongue as it moves forward can be monitored on a subject during sleep to obtain a baseline behavior. The tongue movement can be correlated to a sleep state, thereby, obtaining tongue movement information that relates to the status of the user. During treatment of snoring and OSA, tongue pressure can be monitored as the regimen of stimulant is delivered. A correlation between delivery of stimulant and tongue pressure can be drawn to establish the effect of stimulant on tongue movement. In turn, tongue movement can be correlated to a sleep state of the user, as described above, to establish a correlation between tongue movement and the effect of stimulant on the sleep state of the user. In another example, a pressure sensor can be positioned in the space underneath the tongue. The pressure measurement can be correlated to the position and tone of the tongue and to the sleep state of the user. In another example, two or more position sensors can be placed in the mouth and tongue movement can be monitored with respect to the sensors.

Figure 6A:
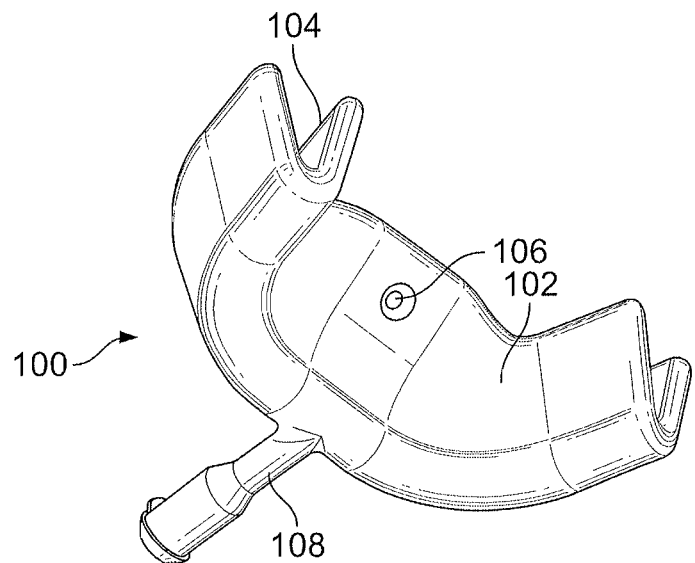
FIGS. 6A to 6E illustrate additional variations of oral devices for use as described herein.
Figure 6B:
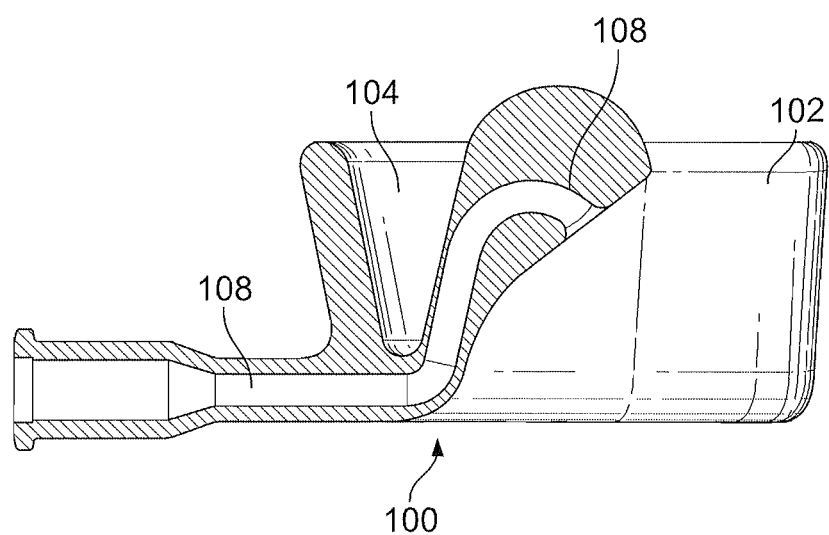

FIGS. 6A to 6E illustrate additional variations of oral devices 100 for use as described herein. FIGS. 6A and 6B illustrate an oral device 100 similar to that shown above having a dispensing port 106 that can be used to deliver a stimulant to the oral cavity, mouth and/or tongue. The port 106 is coupled to a supply of the stimulus via a tube 108 that forms a part of a fluid path between the supply or reservoir of the stimulus and the port 106. In this variation, the tube 108 includes a fitting to allow for coupling to an external reservoir. As described in further detail below, a valve (not shown in FIG. 6A) can be located between the port 106 and the reservoir. Alternatively, the valve can be positioned at the port 106. As noted above, some variations of the device do not include a valve. Instead, the device uses a pressure differential to drive the stimulant through the port.

Figure 6C:
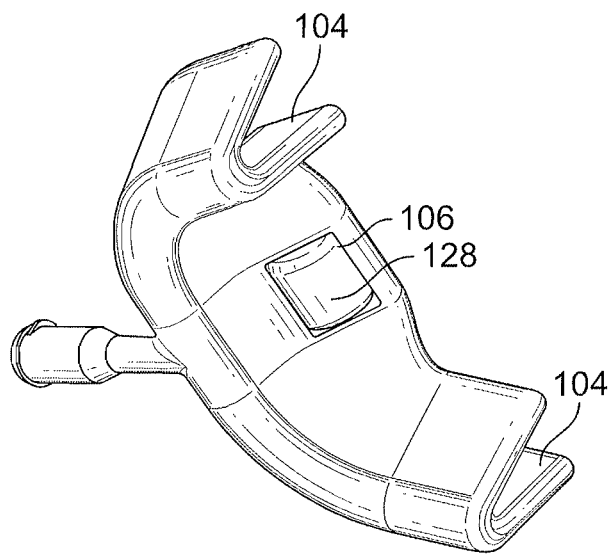
Figure 6D:
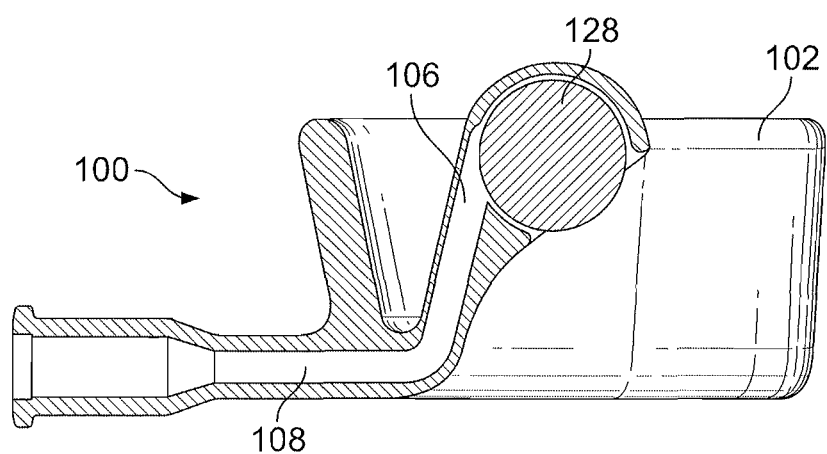

FIGS. 6C and 6D illustrate another variation of an oral device 100 where the dispensing port 106 includes a roller 128. The roller ball can be replaced with a sponge or other similar type structure. The stimulation elements (roller, sponge, etc.) can be smooth or incorporate a texture and have a rigid or soft consistency that can be used to deliver a stimulant to the oral cavity, mouth and/or tongue. The use of the stimulation elements can optionally eliminate the need for a valve for metering the stimulant.

Figure 6E:
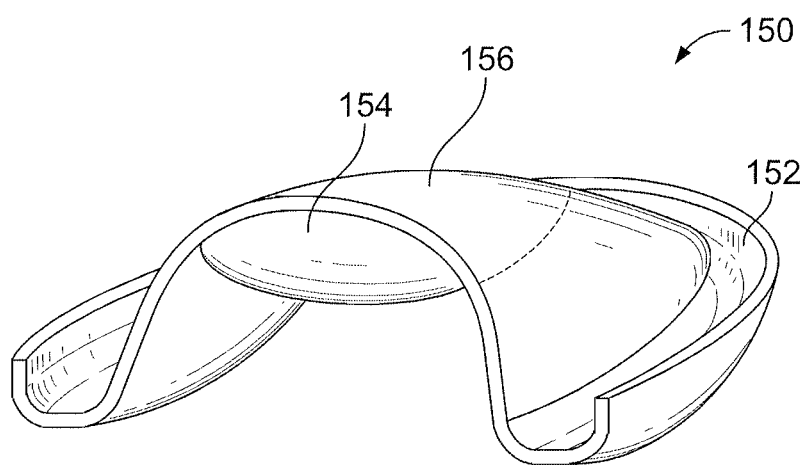

FIG. 6E illustrates another variation of an oral device 150 for use as described herein. In this example, the oral device 150 is configured to function as an upper jaw retainer, with a receptacle 152 for the teeth, and with a reservoir 154 that contains a capsule in the upper hard palate region 156. The stimulant can include a typical gelatin capsule that dissolves in water or saliva in about 15 to 30 minutes. This time range is typical for people to fall asleep. Once the capsule dissolves the taste compound inside the capsule starts to leach out of the capsule into the patient mouth triggering access salivation. In order to prevent the citrus compound from releasing all at once, the citrus compound can be in the form of a "hard candy" like form. Alternatively, the reservoir 154 can be replaced with a supply line that couples the device 150 to an external supply of the stimulant.

In another embodiment of this invention the taste compound could be in a compartment in the mouthpiece or retainer and having a valve. The valve can be controlled by an electronic switch. The sequence of the release of the taste compound can be programmed to be once every few seconds to few minutes. In another embodiment of this invention the taste compound is in a compartment in the mouthpiece or a retainer and has an electronically controlled valve. In addition the electronic circuit for the valve control is designed to receive a trigger signal for the release of taste compound in pre-determined dosage. The signal could be triggered by monitoring a user's vital signal to assure that user is asleep prior to start releasing taste compound.

Figure 7A:
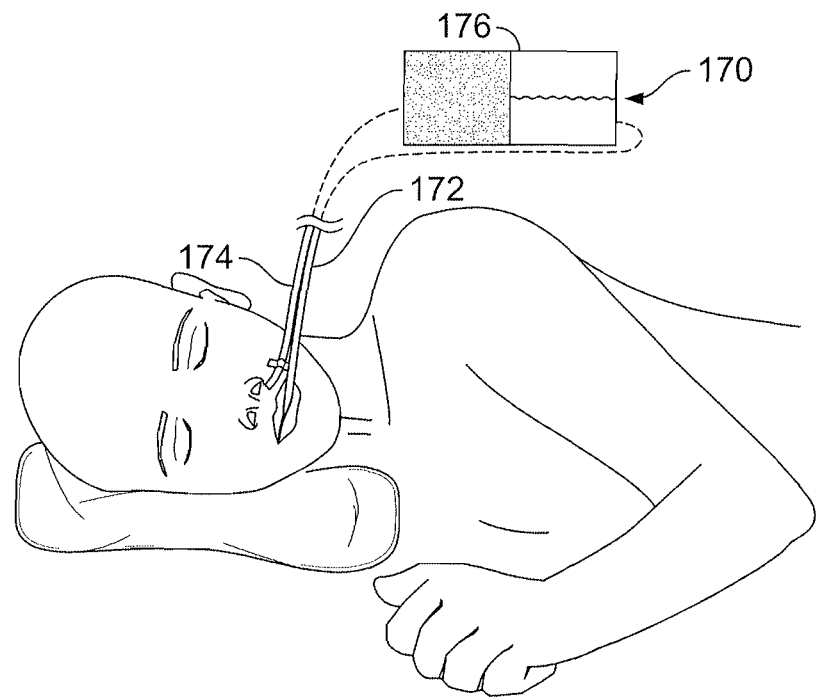
FIG. 7A illustrates another variation of a dispensing device in which the device simply comprises a stimulant tube and a scent tube.

FIG. 7A illustrates another variation of a dispensing device 170 in which the device 170 simply comprises a stimulant tube 172 and a scent tube 174 each coupled to a reservoir or controller 176 that houses the respective stimulant and/or scent. Alternate variations contemplate the use of an aromatic stimulant such that scent is triggered by the mere deployment of the stimulant. As shown in FIG. 7A, the tubes 172 and 174 are merely affixed to the patient to intermittently deploy the stimulant. In an alternative variation, the tubes can be combined into a single tube. Furthermore, the tubes can optionally be fitted with the sensors discussed herein.

Figure 7B:
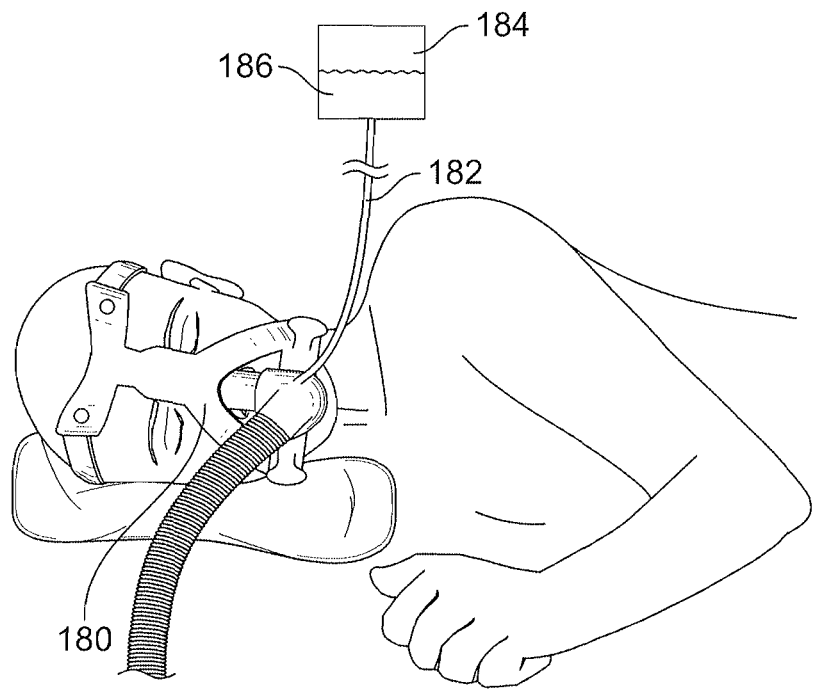
FIG. 7B shows a Constant Positive Airway Pressure (CPAP) device combined with the teachings disclosed herein.

FIG. 7B shows a Constant Positive Airway Pressure (CPAP) device 180 combined with the teachings disclosed herein. As shown, the CPAP device 180 can include a separate supply 182 to couple the CPAP device 180 to a source 184 of a stimulant 186. Alternatively, the CPAP device can be used with a self contained device as disclosed above.

The stimulant described above can take the form of a liquid of low or high viscosity, a solid, a semisolid or paste, a gas or a combination thereof. The properties of the stimulus are such that delivery within the mouth causes a biological or natural reaction. This reaction can include generation of saliva to cause swallowing but in an amount that does not awaken the user from a sleep state. Alternatively or in combination, the stimulant can cause movement of the tongue or repositioning of the tongue in a forward position against the teeth.

Figure 7C:
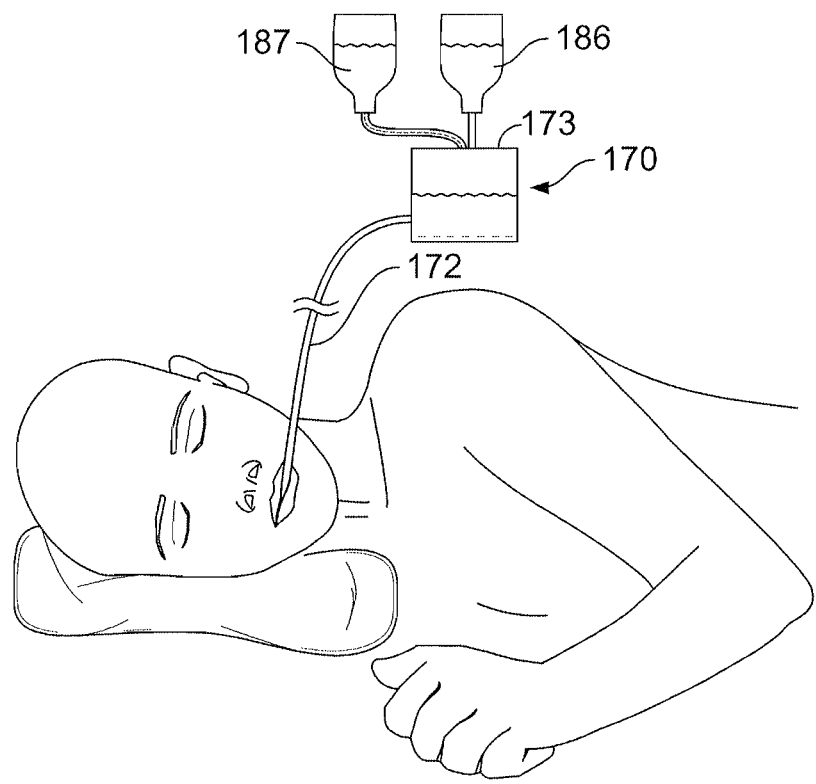
FIG. 7C shows yet another variation of a dispensing device in which the device comprises a stimulant coupled to a solution so that the stimulant can be diluted.

FIG. 7C illustrates yet another variation of a dispensing device 170 in which the device 170 comprises a stimulant tube 172 coupled to a solution supply 173. A stimulant supply 186 can feed into the solution supply 173 along with a second substance 187. One variation contemplates the second substance 187 to dilute the effects of the stimulant to allow for continuous dispensing of the solution over a period of time during the night or periodically.

The stimulant can comprise any number of tastes including, but not limited to sweet, sour, bitter or salty.

Examples of liquid stimuli are solutions of Xylitol, saline and citrus. Smell stimuli include odors and fragrances that stimulate salivation and swallowing during sleep, such as banana, strawberry, orange, other fruits, vanilla, or mint. Preferably the stimuli can be delivered to the user over normal periods of sleep and as a long term therapy for snoring or sleep apnea, without causing untoward effects to the anatomy and physiology, such as degradation of the teeth or gastric disturbances. In the cases of taste and smell stimuli, the stimulation appliance incorporates a reservoir that allows for delivery of the stimulus over the sleep period.

Alternatively, in another embodiment, the compound that increases salivation could be other fruit flavors or other food flavors of the particular user's choice. The mouthpiece or retainer is either designed for repeated use or disposable. Once the user wakes up in the morning, he/she will remove the device out of the mouth, rinse it and allow it to dry. Next night prior to sleeping, the patient would insert a capsule containing taste compound in the device or reload the taste compound reservoir, place it in the mouth and fall asleep. In the case of a disposable mouthpiece, optionally the capsule or reservoir could be packaged preloaded with the taste compound or allow for placement of a capsule or filling of a reservoir, similarly to a reusable device. In another embodiment the reservoir comprises a primary reservoir, a secondary reservoir and a passive valve on the secondary reservoir that opens at a prescribed pressure. The primary reservoir which contains the taste compound fills the secondary reservoir at a uniform flow rate through an orifice between the reservoirs. The driving force for flow between the primary and secondary reservoir is enabled by gravity or, optionally, by a plunger driven by a spring. The secondary reservoir fills until it reaches a volume that exerts the cracking pressure of the passive valve, allowing delivery of an aliquot of the taste compound.

Example 1

Figure 8A:
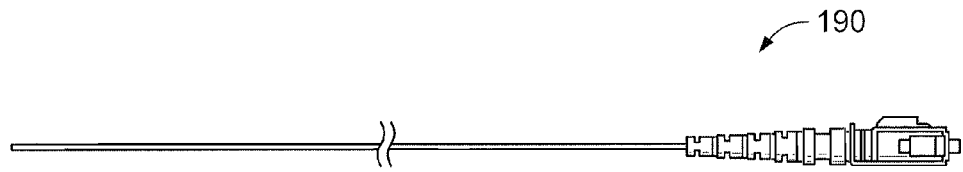
FIG. 8A illustrates one example of a fiberoptic pressure sensor for use in a variation of an oral appliance as described herein.

As discussed above, abnormal head and neck anatomy and decreased pharyngeal dilator muscle tone are two primary contributors to OSA. Both conditions affect the tongue and result in the tongue's having a central role in OSA. One variation of a device using a stimulant (e.g., a flavored substances) to engage the tongue and alleviate tongue-related obstruction can include the use of one or more pressure sensors within the existing intraoral device. For example, FIG. 2A illustrates sensors 116 that will detect the presence or absence of the tongue in a desirable position within the mouth. FIG. 8A illustrates one example of a fiberoptic pressure sensor (supplied by FISO Technologies Inc., Quebec, QC, Canada).

In this example, the outer diameter of the sensor was 260±20 μm, and the outer diameter of the fiberoptic cable connecting to it (extending from the subject's mouth when deployed) was 1 mm. In some variations it is important that the sensors not interfere with tongue movement. Also, the pressure sensor (in this case the fiberoptic cable) should be well-tolerated due to its small size. In the variation used, two sensors 190 (FOP-M260 sensors) are placed within the intraoral device (as shown in FIG. 2A) on the lingual aspect of the dentition 116 to enable direct tongue contact. The locations chosen are anteriorly in the midline and more-laterally, between the canine adjacent to the first premolar. However, alternate placement of the sensor is well within the scope of this disclosure. In the present example, the sensors could be secured in position with the use of medical-grade adhesive against the intraoral device, identically as for the stimulant supply tubing 108.

In cases where an optical sensor is used, the sensor relies on Fabry-Pérot whitelight interferometry to use a light source (bright incoherent light) that is split 50/50 within a 2×2 coupler. The light passes through the optical connector and optical fiber to reach the sensor, which is a Fabry-Pérot interferometer (see FIG. 5). Within the sensor, the light is reflected, but a large number of parallel beams escape the optical fiber core. These are redirected back into the optical fiber core, creating a light interference pattern that is associated with the distance between the semi-reflective mirrors in the sensor. Changes in pressure at the sensor tip alter the length of the Fabry-Pérot cavity in the sensor and thereby change the interference pattern. The light from the sensor is reflected back through the optical fiber to the coupler. The coupler then splits the light, with half of this light directed back to an optical box, where it is spread over a Fizeau wedge that reconstructs the interference pattern and records it with a charge-coupled device.

Use of the FISO Technologies FPI-HR system in combination with the oral implant device described above allows for acquisition of pressures using the FOPM260 sensor at up to 15 kHz over a range of −300 to +300 mm Hg and accuracy within 2 mm Hg. Although two sensors were used and enable a more-thorough assessment of tongue neuromuscular activation than is possible with one sensor. Any number of sensors is contemplated within the scope of this disclosure.

Figure 8B:
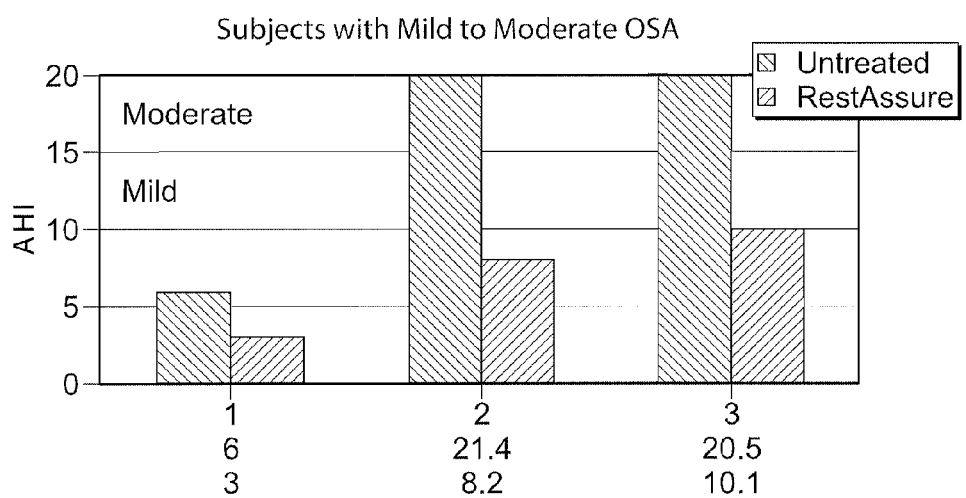
FIGS. 8B and 8C show data from a trial using a variation of a device.
Figure 8C:
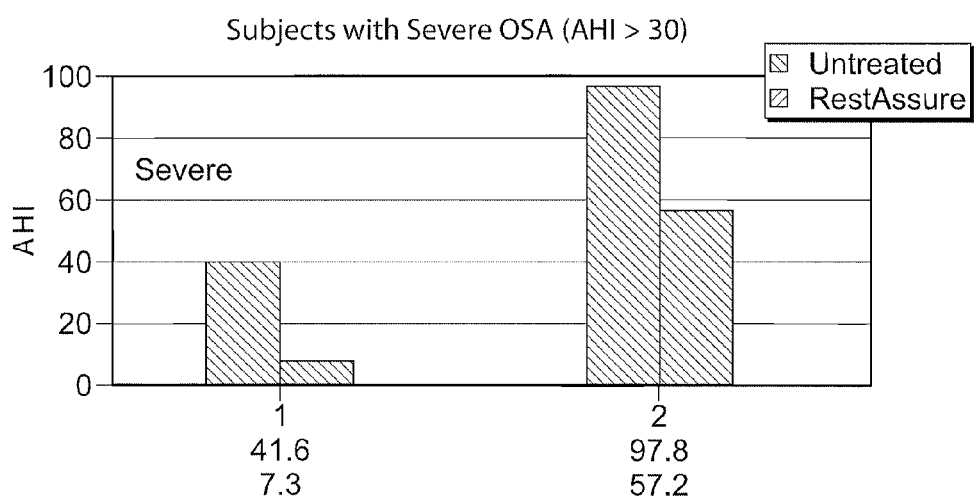

FIGS. 8B and 8C demonstrate the results of a custom fitted oral appliance (similar to that shown in FIG. 2A). In the experiment a patient received a 40% xylitol solution infused into the anterior oral cavity for 5 minutes at a constant rate of 0.1 ml/min. The infusion was initiated every 10 minutes, producing an alternating pattern of 5 minutes on, 5 minutes off throughout the night. FIG. 8B presents the apnea-hypopnea index (AHI) results for individuals with mild to moderate OSA, while FIG. 8B presents the apnea-hypopnea index (AHI) results for individuals with severe OSA. Overall, there was a decrease in the apnea-hypopnea index (AHI) from 37.5 to 17.1 events/hour, with the decrease from 16.0 to 7.1 in mild to moderate OSA and 69.7 to 32.3 in the severe OSA group. The changes in the mild to moderate OSA subgroup, including the decreases in AHI of >50% in all subjects and the low levels of residual AHI, have led to the eligibility criterion of mild to moderate OSA in the proposed clinical trial. In addition to the reduction in AHI, there was a corresponding decrease in the arousal index and no change in sleep architecture (normal percentage of time in REM sleep).

Example 2

1. Introduction:

The tongue plays an important role in snoring and obstructive sleep apnea, contributing to turbulent airflow and upper airway obstruction during sleep. An intraoral device is used in this experimental example to deliver flavored substances in the anterior oral cavity, with the goal of induced tongue chemoactivation and anterior tongue movement towards the flavored substances. The effect of this chemoactivation is to open the airway by overcoming the natural decrease in muscle tone during sleep that leads to posterior tongue prolapse. In this study, tongue sensors were incorporated into the intraoral device, placed immediately posterior to the maxillary (upper) central dentition. The objective of this study was to examine tongue chemoactivation and anterior tongue movement associated with the administration of flavored substances in the anterior oral cavity.

According to one aspect illustrated by this experimental study example, a tongue position sensor ("TSE") assembly and method is configured to detect tongue repositioning activity to the sensor position. Moving the tongue anteriorly into such a position, in particular toward the front teeth, repositions the tongue out of the posterior pharynx.

This TSE approach monitors the presence, and absence, of this protective tongue repositioning activity against pharynx obstruction. The specific TSE embodiment constructed under this experimental example is not necessarily configured for the additional directed purpose to also measure all tongue positioning activities—and some of which are present in the normal individual to prevent obstructive events. Pathology will generally occur via the tongue receding to the posterior pharynx and causing obstruction. It is also considered highly beneficial to detect the presence any one of multiple protective tongue activities, as indicating a likelihood that the tongue is non-obstructively positioned relative to the posterior pharynx. In the setting of a therapy intended to achieve this result, such detection also confirms the functional success of the therapy.

Devices and related methods that are configured to reposition the tongue out of the posterior pharynx have been proposed, and constructed, tested, and demonstrated that such tongue repositioning may resolve or at least improve these obstructive events and other related disorders. Certain such approaches are configured to stimulate tongue movement for such repositioning, i.e. as tongue repositioning stimulators ("TST"). Such a TST may be configured and operated by a number of mechanisms and methodologies. Certain exemplary embodiments include, without limitation: (1) the TST may be configured and operated to apply a force to the tongue to directly move it into the desired anterior position; or (2) the TST may be configured and operated to apply a stimulation which invokes a biological response in the subject which moves the tongue into the desired position; or (3) a combination of (1) and (2). Certain further embodiments of (2) above include, without limitation, a stimulation media which is delivered via an appropriately configured TST assembly and method in a manner to stimulate a response to cause the tongue positioning. This stimulation media may comprise, according to further embodiments, and without limitation: (a) a fluid, and which may typically be a liquid, though may also be a gas; (b) a semisolid, paste, or gel; (c) a solid; (d) a flavor, taste, or smell invoking the responsive tongue movement; or (e) a combination of any of the preceding, i.e. a fluid flavor stimulus, such as for example a liquid flavor or taste stimulus—as is used in the present experimental study example.

Another aspect of the present disclosure provides a TST may be configured for passive delivery of the stimulus, such as for example simple passive dissolving of a stimulus material or diffusion of a fluid into the mouth.

However, according to another aspect of this disclosure exemplified by the present experimental study, a TST may comprise controlled delivery of the stimulus, i.e. as a controlled TST or "cTST." According to one beneficial mode of this aspect, the cTST comprises a controller which controls the stimulus delivery. In certain beneficial embodiments, this comprises controlled delivery of a stimulus media, which may be in further embodiments, for example but without limitation, at least one of a fluid and a flavor stimulus. A cTST comprising a controller to control delivery of a fluid flavor stimulus is provided and used under the current experimental study.

The controller of a cTST may control stimulus delivery according to various different desired delivery profiles, e.g. amounts, rates, or "dosage" regimen of the stimulus therapy over time. According to one embodiment, this comprises a relatively fixed profile for constant delivery or dosing regimen of the stimulus therapy over time (such as for example during sleep). However, according to another embodiment, this comprises controlling the delivery profile and dosing regimen to change over time, e.g. between different conditions (i.e. amount and/or rate of stimulus delivery). Such changing profile may comprise, for example, a continuous rate of change, or discontinuous rate of change, or a combination thereof in different time intervals, over a therapy dosage period (e.g. during sleep). This change can be between on and off conditions—either in absolute terms, or in functional context with respect to being above or below, respectively, a threshold for achieving the intended results of stimulation. It is thus appreciated that this controlled delivery may be modulated to change between levels of applied stimulus (which may be according to a pattern, such as a cycle; or may be another form of changing profile).

The controller of a cTST system and method may comprise a relatively simple control mechanism, or may be more complex. According to one example, it may comprise a pump for delivering a fluid stimulus according to either fixed or adjustable delivery rates, change(s) in rate, and/or other settings which may be either manual or automated, or a combination thereof. The controller may also comprise a computer software program embedded in a non-transitory computer readable medium and configured to be run by a processor, and/or a processor configured to run and process an embedded computer software program in a non-transitory computer readable medium.

The current experimental example involves a particularly beneficial cTST embodiment which comprises a controller, liquid stimulus source, and oral delivery assembly—all assembled in an overall system for controlled pump delivery of the liquid flavor stimulus at an anterior location within the mouth, in particular behind the front teeth. The flavor stimulus applied in the proper position, in particular posteriorly adjacent to the front teeth, stimulates movement of the tongue forward into the proper anatomical position and out of the posterior pharynx (i.e. protective tongue repositioning activity). In addition to this type of protective repositioning, there may also be additional protective responsive mechanisms, such as that muscle tone is improved sufficient to remove the tongue out of the posterior pharynx such that it is no longer obstructing breathing.

According to another aspect exemplified by the embodiment of this experimental example, a TST is provided in combination with a tongue position sensor (or "TST-TSE") system. According to one mode of this aspect, the TSE is used to assess the performance of the TST to stimulate the tongue into the anterior protective repositioning activity. According to another mode, a cTST is combined with the TSE to form a "cTST-TSE" combination system. Further to this mode, the sensed tongue position information provided by the TSE is used as a real-time diagnostic basis and input into the cTST, and at least in part by which the configuration and operation of the controller of the cTST is based. In one embodiment, in response to the TSE sensing an absence of (or reduction or movement away from) the anterior protective position, the cTST is configured and operated to control the stimulus delivery to apply the stimulus in a manner that causes the tongue to move into the anterior protective position. In another embodiment, in response to the TSE sensing the tongue is in the anterior protective position, the cTST is configured and operated to control the stimulus delivery to stop or reduce the application of the stimulus. This may provide a benefit, for example, to prevent overstimulation and potential wakening of the subject, or prevent habituation or desensitization of the tongue movement response to the applied stimulus.

2. Purpose:

The current study was designed and conducted as a 14 day trial of a single control subject without a history of obstructive sleep apnea. The test subject was subjected to consecutive nightly exposure to a liquid stimulus, xylitol, administered in the anterior chamber of the mouth (or anterior oral cavity). This was conducted via a new and useful cTST delivery assembly and method constructed for stimulant delivery via an oral appliance according to a particularly beneficial embodiment of this disclosure. A TSE was also included, also incorporating the oral appliance, in an overall cTST-TSE system. The hypothesis entering the experiment was that the TSE will be able to demonstrate the anterior protective tongue repositioning activity in response to this applied xylitol exposure via the cTST, thus showing that in response to the novel cTST therapy:

(a) the subject's tongue moves forward into the anterior protective position, and will trigger the sensor of the TSE; and (b) the anterior protective tongue repositioning activity is repeatable night after night and does not habituate or disappear over the two week period.

During the 14 night trial, certain parameters were varied to compare effects, via changes in pressure at the sensor of the TSE, of various rates and intervals of xylitol exposure via the cTST, including examining for differences in acute responses for multiple infusion rates and dosing intervals as well as for habituation over the 14 day period.

3. Materials:

A custom cTST-TSE mouthpiece or dental retainer, stimulus delivery controller, liquid flavor stimulus, and pressure sensor (including recording means) were all prepared and assembled in an overall cTST-TSE system, illustrated in partial schematic view in FIG. 9, as follows:

a. Custom TST-TSE Dental Retainer

A custom mouthpiece was configured as a dental tray made by thermoforming a plastic retainer to a mold of the patient's teeth. The custom configuration constructed and used is palatal arch-less, and secured by form fitting to the teeth. This shares certain similarities to such dental retainer trays made and sold under the name "Invisalign™" or otherwise for braces or certain teeth whitening trays. However, the current dental tray retainer also comprises certain distinct differences which are both structurally and functionally unique—and exemplify various inventive aspects of the present disclosure concordant with the unique functional purposes intended.

The dental retainer is vacuum formed with an Essix™ Vacuum Thermoforming Machine, model #85000 sold by "Dentslpy™." While various materials may be suitable and used for this purpose, the material chosen for this particular experiment is plastic, and more specifically a Dentsply™ plastic: "PET Essix A+." The plastic tray was constructed for this particular experiment with a wall thickness of about 0.02 inches.

As two particularly unique features of the present embodiments of this example, two tubes were also secured to the tray, in particular by UV bonding each of two IV tubes to the tray for purpose of this specific experiment (though other bonding, securement, or integration of the features may be sufficient). These tubes were secured in a configuration to create two ports, respectively, on the posterior lingual side of the anterior two front teeth—and which were generally adjacent or "side by side" (though exact side by side adjacency is not considered absolutely necessary, and other relative locations may be suitable). The tubes were also configured to extend anteriorly away from the tray, teeth, and mouth and externally of the patient. This construction provides the unique custom result of a delivery tube and respective delivery port for stimulus delivery to the posterior lingual side of the anterior teeth, and sensor tube and respective sensor port at a similar, generally adjacent, location. In the physical embodiment constructed for this experiment, these tubes terminated in luer lock ports. One port was connected to an infusion pump, with a 30 BD syringe filled with the 40% xylitol solution.

b. Liquid Flavor Stimulus

Xylitol sugar (sweetener frequently used, such as for example in Trident™ gum) was mixed with tap water in 40% concentration to provide the liquid flavor stimulus. This was retained and dispensed during the experiment using a standard, commercially available 30 ml "BD" Syringe. Delivery was accomplished via the standard small bore IV tubing noted above as secured to the TST-TSE dental retainer.

c. Stimulus Delivery Controller

An infusion pump (Baxter™ AS40™ Auto Syringe Infusion Pump™) was also provided to control the delivery via the syringe, via delivery profile parameters that were configured to a variety of settings for purpose of the test agenda and hypotheses.

d. Pressure Sensor

Pressures were collected using a commercially available FOP-F125™ pressure sensor. This sensor was located adjacent to the inlet port for infusion of the xylitol solution, directly behind the maxillary (upper) central dentition. The sensor tip was positioned within an auto-inflating, cotton fiber-filled polyurethane bubble that was designed as part of a closed system with the sensor. The pressure sensor was also coupled to the pressure tubing secured to the TST-TSE dental retainer. The sensor was also connected to a signal processor and the signal processor was connected to a PC with analytic software. More specifically, it was connected to a FPI-HR Module™ signal conditioner (manufactured by FISO™ Inc.). Data collected was then recorded to a standard PC, using Evolution™ software also provided by FISO™ Inc.

4. Methods

The test subject was fitted with the custom TST-TSE retainer. One proximal port was connected to the infusion pump, per the 30 BD Syringe filled with 40% Xylitol solution. Xylitol infusion rate was set at various parameters, as described in further detail below.

A second proximal port was connected to IV pressure tubing, leading to a sealed chamber containing the sensor. The sensor was connected to a signal processor and the signal processor was connected to a PC with analytic software, as described above.

Figure 9:
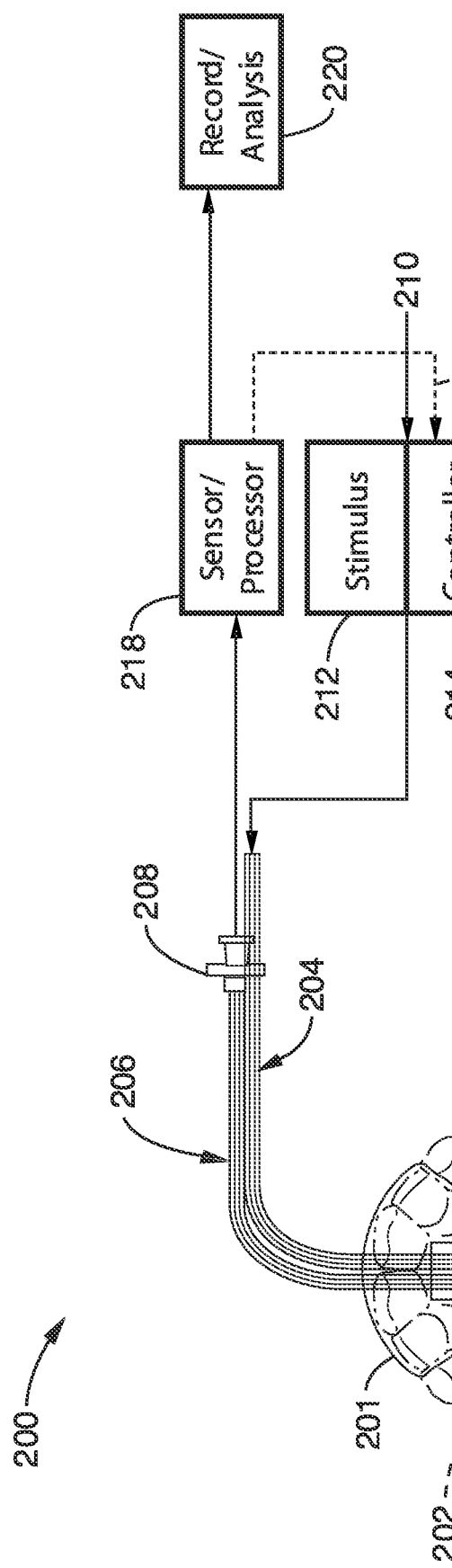
FIG. 9 shows the cTST-TSE system according to one aspect of the disclosure, with certain components shown schematically for simplicity of illustration.

FIG. 9 shows an embodiment of the cTST-TSE system 200 described above, with certain components shown schematically for simplicity. More specifically, FIG. 9 shows (though not readily visible as it is clear) a cTST-TSE retainer 202 on a white model of teeth 201, with tubes 204, 206 extending from the cTST-TSE retainer 202 and terminating in couplers such as shown at luer lock 208 for tube 206. These tubes are fluidly coupled via passageways formed in the retainer 202 to a dispensing port and sensor, respectively, at adjacent delivery and sensor locations, respectively, on the central anterior aspect of the oral cavity posteriorly adjacent to the middle two front incisor teeth (not revealed in the detail shown). Tube 204 comprises a delivery tube and is also fluidly coupled to a controlled stimulus delivery assembly 210 located externally of the mouth and comprising a source of stimulant 212 and a controller 214. Tube 206 comprises a sensor tube and is also fluidly coupled to a pressure sensor processing assembly 216 via luer lock coupler 208.

Stimulant from the source 212 is delivered via delivery tube 204 to the dispensing port at the delivery location. In response, the tongue is stimulated to be repositioned to an anterior protective position against the front teeth and thus with applied pressure against the sensor at the sensor location. This is conveyed via sensor tube 206 to the sensor processor 218. In a cTST system, the sensed pressure is converted to a signal with a value that is communicated to the controller 214 in a feedback coupling 216, e.g., electrical communication between the two appliances. While it is considered a beneficial embodiment (though not necessary) of the present disclosure to control the stimulus delivery via the sensed tongue position, this coupled feedback loop between was not incorporated into the current experimental study design. In the current experimental design, the sensed pressure is processed into data which is recorded for analysis, as shown at block 220 schematically in FIG. 9. Screen shots and data files were collected for comparative analysis. Controlled stimulant delivery was instead managed by predetermined parameter inputs to the controller under a controlled experimental design with controlled ranges of delivery variables.

5. Results

Results follow in 4 basic categories: (i) Examples of "on" and "off" states of TST xylitol delivery; (ii) changing delivery rates, per pilot study protocol, 5 min on (about 100 μL/min), 5 min off (about 0 μL/min); (iii) changing delivery, at shorter Intervals of (a) 2 min on, 3 min off, with "on" at various rates of 100, 50, and 25 μL/min, and (b) 3 min on (about 33 μL/min), 3 min off; and (iv) continuous "on" state (about 150 and 33 μL/min).

(i) Examples of Device ON/OFF States

Figure 10:
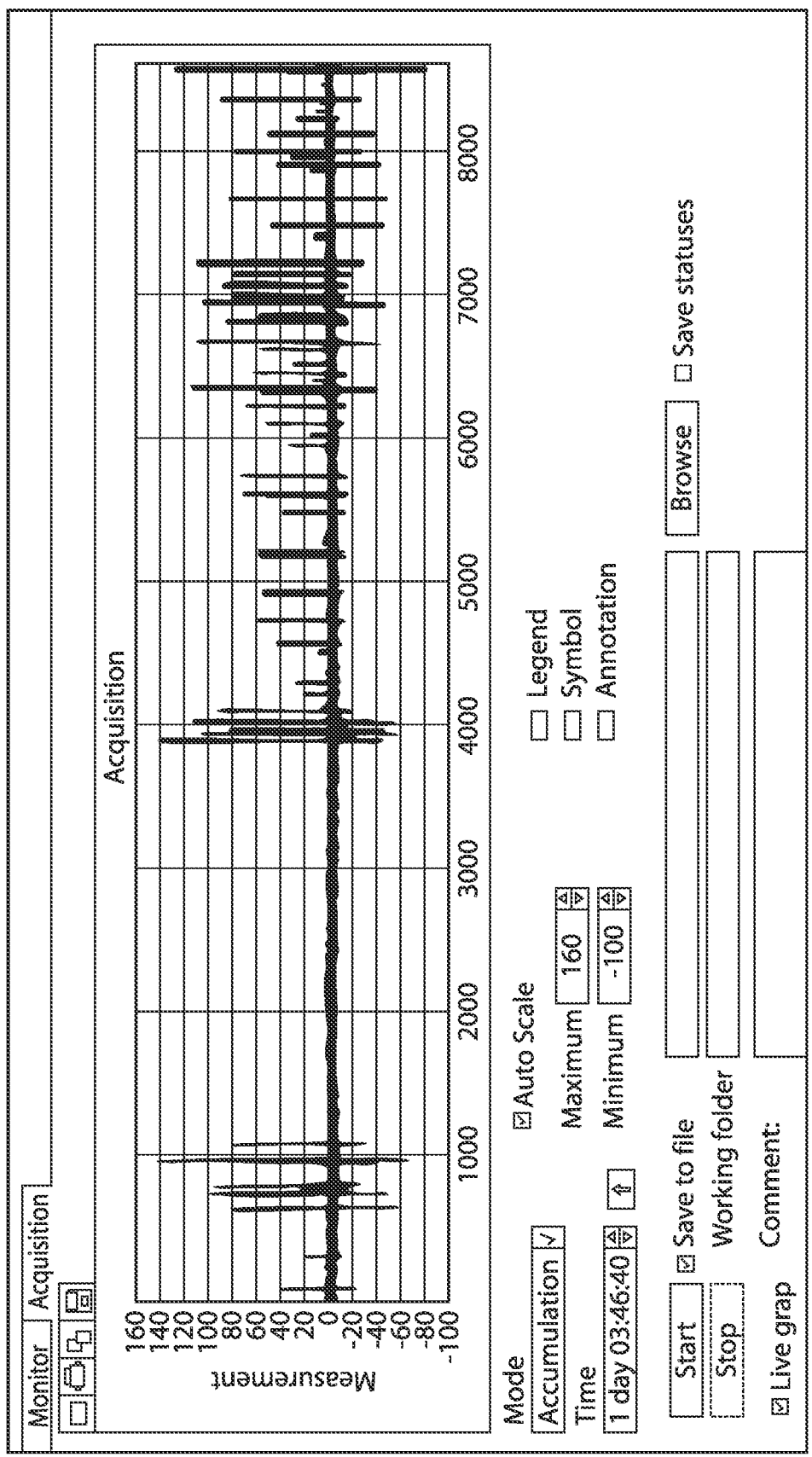
FIG. 10 shows a graph of certain sensed anterior tongue pressure data recorded versus time under the experiment of Example 2, and reflects an example comparing time periods of varied ON/OFF states of therapy delivery.

FIG. 10 shows a graph of results according to sensed anterior tongue pressure vs. time (example, ON/OFF states). Certain relevant observations include, without limitation, the following:

(a) from 0-1,000 seconds, subject is awake with several events of anterior protective tongue repositioning activity apparent via sensed pressure data recorded;
(b) from 1,000 to 3,650 seconds, the device is in place but OFF. The recorded pressures during this period reveal no apparent anterior protective tongue repositioning against the sensor during the OFF mode; and
(c) starting at 3,750 seconds, the controlled pump device assembly is set to continuous on. Recorded pressure results show an appreciable amount of anterior protective tongue repositioning activity during this period.

FIG. 11 also shows a graph of results according to sensed anterior tongue pressure vs. time (example, OFF only). The device is in place and worn by the subject, but set to OFF. The results demonstrate there is almost no anterior protective tongue repositioning activity when the controlled stimulus delivery device is turned off:

(a) limited activity at 100 seconds, reflecting awake state, then again at around 2,000 seconds (a possible swallowing event); and
(b) the recorded pressure data over the rest of the recording period reveals virtually no anterior protective tongue repositioning activity, though the tongue is not believed to have been obstructive to the pharynx (perhaps due to good tone or other protective position), as evidenced by lack of suspected obstructive events or related sleep disorder.

(ii) Per Pilot Study Protocol, 10 min ON/OFF Cycles (5 min ON, 5 min OFF, Rate=100 μL/min)

FIG. 12 shows a graph of frequency of sensed anterior protective tongue positioning events (per second) vs. time (consecutive nights over 14 day period), according to this test protocol. More specifically, FIG. 12 shows graphical results using the same rates and intervals on four separate nights throughout the 14 day trial demonstrating that the tongue activity is generally repeatable (obviously within a certain range of variability) night after night and does not reveal a trend that there is habituation to the stimulus or disappearance of the biologic repositioning response over the two week test period.

FIG. 13 shows a graph of same results featured in FIG. 12, per frequency of sensed anterior tongue positioning events (per second) vs. time (consecutive nights over the 14 day period, in split-night view). However, FIG. 13 shows a closer look at the same nights in same test subject, comparing the first half of the night to the second half (i.e. "split night" view or analysis). While again certain range of variability is shown, out to night 14 similar activity is observed as was observed at night 4, and without significantly apparent difference between first and second halves of the night on that 14$^{th}$ night following continual treatment over the 2 week period.

(iii) Shorter Interval, 5 or 6 min ON/OFF Cycles (2 or 3 min ON, 3 min OFF, at Various Rates)

FIG. 14 shows a bar graph of results according to frequency of sensed anterior protective tongue repositioning events (per second) vs. time (consecutive nights over 14 day period). More specifically, the FIG. 14 bar graph shows results of using a shorter interval than the pilot trial protocol with various rates. As shown over this test period, the sensed frequency of anterior protective tongue repositioning activity appears to reduce in direct relationship with reducing stimulant delivery rate across the matrix from 100 uL/min on night 5 to 25 uL/min by night 13. This again suggests confirmation that the stimulant delivery appears to be playing an active role in the desired tongue repositioning activity.

FIG. 15 also shows a bar graph of results per frequency of sensed anterior protective tongue repositioning activity events (per second) vs. time (consecutive nights over 14 day period). However, while FIG. 15 provides a closer look at the same nights in same subject as FIG. 14, this graph of FIG. 15 compares the first half of the night to the second half (when available) in split night analysis.

(iv) Continuous Rate (Continuously ON, at Two Different Stimulant Delivery Rates)

FIG. 16 also shows a bar graph of frequency of sensed anterior protective tongue repositioning activity events (per second) vs. time (consecutive nights over 14 day period). However, this is a graph of results during continuous flow, with no pauses in delivery of xylitol, but comparing two different stimulant delivery rates. An obvious reduction is apparent in sensed events in direct relationship to the reduction from the 150 uL/min rate on night 1 (about 9.5 events), and the 33 uL/min rate on night 12 (<4 events)—in fact the >50% reduction in delivery rate resulted in >50% reduction in the desired tongue repositioning events.

6. Additional Analysis/Discussion

FIG. 17 shows a graph of sensed tongue movement to the protective anterior position as a function of varying stimulant delivery rates. The results show that tongue movement is maintained at even lower rates. It is noted that with no flavor there appears to be a considerable drop-off in response. It is also noted in this data that certain points reflect continuous on, whereas others represent cycled on/off conditions (as reflected in the legend).

FIG. 18 also shows 14 days of consecutive treatment at various rates and protocols.

The current Example 2 reflects data from a 14 day trial of a single control subject, without a history of obstructive sleep apnea. A consecutive nightly exposure to xylitol was administered in the anterior oral cavity via the novel cTST-TSE system described.

The experimental data demonstrates that the tongue moves forward and is drawn to the anterior oral cavity against the front teeth with the novel anterior protective tongue repositioning stimulation treatment used. The affect is not appreciably present with the device in place and turned off. The presence of the oral appliance alone, not turned on, is not sufficient to cause the movement of the tongue. Additionally, the study also reveals that this cannot be optimally achieved just by using plain water without a flavor, since the presence of flavor appears to greatly enhance the tongue movement—as reflected in this data. This clearly demonstrates the mechanism of action, where the tongue is stimulated to come forward in the presence of flavor stimulus when administered according to the unique systems and methods used in this experiment. This is expected to provide protective benefit during sleep, since it is known that bringing the tongue forward from a posterior position to the anterior oral cavity as in this experiment clears the posterior pharynx and reduces symptoms of obstructive sleep apnea.

In addition, there was no appreciable habituation observed after two weeks of this unique therapy. There were different rates used over the 14 day study, but comparing the four nights of standard rates "protocol" of treatment (i.e. on for 5 min then off for 5 min) no relevant decrease in tongue activity is observed. In fact, the second two nights of this treatment resulted in a greater frequency of tongue movement than the first two protocol nights. This suggests support for a hypothesis that there is actually a conditioning response that takes place, and that successive treatments grow stronger in their stimulation impact and results.

The observations in this study also reveal that the variability of response using different rates and hourly volumes appears to be within the night to night variability of identical treatments. This suggests that the frequency of tongue movement is not likely to be solely dependent on the volume of delivery. Volumes can be reduced such that the frequency of stimulation, the anterior movement of the tongue is consistent.

As would be readily appreciated by one of ordinary skill, while certain specific values and other numbers are recited herein this disclosure, and are considered to provide particularly beneficial examples, unless otherwise stated such values are not intended to necessary limit the broader aspects of the disclosure which they exemplify. Unless stated otherwise, such exemplary values are not necessarily considered exact or absolute—and the exemplary values should be considered in "about" terms. Slight variances may be made to specifically stated values or ranges without departing from the broad aspects exemplified. For example, most dimensions or performance measures, whether stated in the singular, ratio, or range for example, will typically be subject to certain tolerances of the materials, structural designs, operating environment, and methods embodied in the featured numbers. Moreover, variations may also be deliberately made from such specific values disclosed, but while still accomplishing similar or equivalent objectives and results, and still falling within the broader aspects of the disclosure. For example, while remaining subject to and without limiting the preceding aspects of this paragraph above, a tolerance of plus or minus about 10 to about 20 percent of such specified values will typically still be considered equivalent and falling within the intended scope of the specific values herein described.

As would also be apparent to one of ordinary skill, such "values" noted immediately above relate to quantitative or "numeric" values, and also qualitative values. For example, certain exemplary embodiments described hereunder recite an "intermittent" stimulus delivery, and which in certain further embodiments is described to be between "on" and "off" conditions or states of stimulus delivery. It is readily appreciated by one of ordinary skill that such conditions or states should be considered contextual to the related purpose and intended functional results of the respective states. For example, an "on" condition or state of stimulus delivery may be achieved when the stimulus is delivered at or above a certain threshold intended to achieve a functional stimulated result; whereas conversely and "off" condition or state of stimulus delivery may be achieved by a stimulus delivery profile or dosage regimen below that threshold—i.e. functionally equivalent, contextual to the intended result of stimulation, to a complete cessation of any stimulus delivery. Moreover, while an "intermittent" change may be accomplished in discrete intervals that may not be continuous, a continuous change in stimulus delivery amount or rate may be equivalent to an interval change when the change is between such "on" and "off" conditions relative to being above or below a stimulus threshold, respectively.

The present detailed embodiments have been variously described by reference to delivering stimulants or stimulus, and in more particular applications specifically for delivering stimulants to the mouth for stimulating a tongue, and in further detail for stimulating tongue repositioning, and still more specifically to Type 1 or anterior position within the mouth. However, other therapies may also be delivered according to these systems and methods and still fall within the broad intended scope of the various aspects contemplated hereunder.

For example, various different therapeutic agents may be delivered according to the systems and methods herein described. Such agents may be for example materials or molecular agents, which may be in various different preparations for delivery, such as fluid (e.g. liquid or gas), solid, semi-solid, gel, paste, suspension, powder, etc. Or, the therapeutic agent may be in another form such as an electrical current (e.g. RF current for example), thermo-energy (e.g. either heating or cryo/cooling), optical energy (which may provoke an optical response in tissue or provide another form of thermal heating), etc. For one more detailed example for purpose of further illustration and understanding, a low current/voltage RF signal may be delivered similarly in context of the oral delivery systems and methods as described herein with respect to delivering a fluid flavor stimulant (e.g. according to the "Examples"). This may be either in the alternative or addition to such fluid stimulant delivery. For example, delivering such electrical current to a similarly positioned anterior location in the mouth, such as described above for delivery port of the xylitol delivery of Example 2 (e.g. lingual side of front incisor teeth), may also stimulate a tongue repositioning response into the anterior position of the mouth as desired. In another more detailed illustrative example, such current may be delivered via a current source either coupled directly to the oral device or from outside the mouth via a delivery assembly (e.g. electrically via electrical leads similar to fluid coupling via delivery tubes described above). In a further example, this current may also be exposed at an electrode which is located at similar position as the fluid delivery port of the Example 2. In such example, the electrode may be bi-polar with the two electrodes on the oral device itself, or may be monopolar and work via a ground patch placed elsewhere on the patient (as in other RF current medical device assemblies previously disclosed).

Also in the alternative or combination with one or more of the above examples, a thermal heating or cooling element may also be provided at such a location on the oral device in similar anterior position within the mouth—and which may also provide such tongue stimulus for repositioning.

Other variations or modifications to the detailed embodiments above can also be made, and remain within the broad aspects intended to be captured by this disclosure. For example, many different specific sensors and related structural arrangements, for sensing various different parameters, can be incorporated into the sensor embodiments herein shown and described, as well as other embodiments as would be apparent to one of ordinary skill based upon a review of this disclosure.

For further example, optical sensors may be employed, with various alternative assemblies coupling them to mouthpieces. According to one such example for illustration, a light source is coupled to an illumination port on the oral device and configured to transmit an illumination light signal from the illumination port into the mouth. The sensor according to this arrangement may comprise an optical sensor coupled to the oral device at the sensor location. Further to this arrangement, the sensor location is positioned relative to the illumination port such that the optical sensor is configured to sense a reflected light signal that is reflected in the mouth from the illumination light signal transmitted into the mouth from the illumination port.

According to an additional embodiment, an optical fiber is provided with a first end portion with a first end optically coupled to the oral device at the sensor location and also to the mouth in the implant configuration, and a second end portion coupled to the optical sensor located outside the mouth when the oral device is in the implant configuration. Further to this example, the reflected light signal is optically coupled from the sensor location in the mouth to the optical sensor outside of the mouth via the optical fiber.

In another particular example for further illustration, an optical fiber is provided with a first end portion with a first end optically coupled to the oral device at the illumination port and also to the mouth in the implant configuration, and a second end portion coupled to the light source located outside the mouth when the oral device is in the implant configuration. Further to this example, the illumination light signal is optically coupled from the light source outside of the mouth to the illumination port and into the mouth via the optical fiber.

According to another example, an optical fiber couples the illumination port on the oral device in the mouth, at a first end of a first end portion of the optical fiber, to the light source located outside the mouth, at a second end of a second end portion of the optical fiber; whereas an optical fiber also similarly couples the sensor location on the oral device in the mouth to an optical sensor outside of the mouth.

Still further variations are contemplated according to this example. In one such further variation, the illumination port and the sensor location are coupled to the oral device at first and second separate but adjacent locations; and the first and second end portions of each of the fiber optic delivery members are separate, distinct fiber optic delivery members. Further to this variation, the first end portions of each of the first and second fiber optic delivery members may also be, at least in part, bundled adjacently together. According to another variation, the first end portions of each of the first and second fiber optic delivery members comprise the same common fiber optic delivery member. According to another variation, the second end portions of each of the first and second fiber optic delivery members comprise the same common fiber optic delivery member; and the light source and optical sensor are each coupled to the common second end (typically with a splitter, separator, or other mechanism known in the art for measuring transmitted and reflected light via a common fiber optic. In still another further variation, where a common optical fiber is used at the first end coupling to the device for transmitting and receiving reflected light at the optical interface in the body, the second end portion is bifurcated to comprise first and second optical couplers. The first optical coupler is configured to be coupled to the light source, and the second optical coupler is configured to be coupled to the light sensor. Further to this variation, light transmitted from the light source via the first optical coupler and light received by the light sensor via the second optical coupler are transmitted via the common first end portion of the optical delivery member.

Furthermore, other therapies may be also be provided for delivery and use according to the structural system and method aspects, and the exemplary embodiments of this disclosure. This also may be either in addition to or in the alternative to the specific therapies also herein described. For example, this may include therapies other than tongue stimulation or repositioning, other stimulant delivery and stimulus therapies related thereto, or other therapies than stimulation or delivering, or other therapies than those which may be related to the tongue. For example, other therapeutic agents may be employed for other medical or dental purposes, such as for example pharmaceutical agents (e.g. drugs), as the present disclosure provides for a beneficial new approach for oral drug delivery. Accordingly, a wide range of applications may be satisfied for many different target objectives suitable for such oral agent delivery and consumption. This may include something as simple as delivering antiseptic, anti-bacterial, or other form of mouth cleansing, hygienic, or breathening agent, or as significant as delivering a drug (either over the counter, nutraceutical, or prescription) that has either oral, lingual, or other biologic activity for various medical purposes through absorption or consumption via the oral delivery. According to one such example, for illustration and not to limit the broad scope of the foregoing, fluid agents may be delivered orally via these systems and methods and which may treat certain nasal or sinus ailments or conditions.

The devices, systems and methods as described herein can thus be applied for the treatment of various diseases and conditions other than snoring and/or OSA. For example, the disclosed appliance and delivery methods can be used to deliver suitable agents for the treatment of oral hygiene and xerostomia, as well as any other treatment that can benefit from having a stimulant applied in the manner disclosed herein.

Certain embodiments disclosed relate to delivering therapeutic agents, such as stimulants, into the mouth via an oral device. Such embodiments contemplate a broad scope with respect to the particular preparation for such agents in terms of the specific type of material (e.g. fluids, solids, etc.), as described elsewhere herein. These alternatives include in certain regards gas preparations for therapy delivery. However, it is also appreciated that gasses are characterized with properties that rapidly fill a volume or space in which they are introduced. In more detailed embodiments where isolated local delivery to a particular part of the mouth is desired, e.g. only the anterior portion at or adjacent the front incisor teeth, gas may be a non-ideal preparation to optimally achieve the intended result. For example, where anterior tongue repositioning is desired toward the front teeth, delivery of gas at that anterior location may instead rapidly migrate toward the posterior mouth and/or throat, and thus mitigate the local target of the stimulus from its intended anterior location. Accordingly, it is appreciated in certain such embodiments that a "non-gas" category of material preparation of the agent (e.g. tongue repositioning stimulus) is considered particularly beneficial (vs. a gas alternative).

From the description herein, it will be appreciated that methods, devices, and systems are disclosed for controlled delivery of a therapy, such as a stimulant, to a mouth of a subject via an oral device positioned in a secured configuration in the mouth. At least one of a tongue position stimulator (TST) and tongue position sensor (TSE) is provided, according to certain aspects. According to another aspect, a stimulus is delivered to the mouth and/or tongue via a mouthpiece secured to the subject's teeth. In another regard, a stimulus is delivered that generates a natural response to eliminate or reduce sleep disorders, such as for example at least one of snoring and obstructive sleep apnea. In certain embodiments, the therapy delivery comprises at least one of: isolated delivery to only an anterior portion of the mouth at or adjacent to the front incisors, a non-gas preparation of therapeutic agent, and either via coupling an external reservoir to the oral device or coating the therapeutic agent or stimulant onto a dispensing surface of the oral device.

In addition to the disclosure herein, various aspects, modes, embodiments, features, and variations disclosed hereunder are summarized as follows.

1. One embodiment is a method for treating sleep disorder breathing in a sleeping individual, comprising: providing a stimulant that induces at least one natural response within a mouth of the sleeping individual when the stimulant enters the mouth; delivering the stimulant at a location behind one or more teeth in the mouth to induce at least one natural response to reduce sleep disorder breathing and improve the ability of the sleeping individual to maintain a sleep state; and changing delivery of the stimulant.

According to another embodiment, the changing of the delivery comprises reducing the delivery. In another embodiment, the changing comprises intermittent changing. In another embodiment, the delivery reduction comprises intermittently reducing delivery.

2. Another embodiment is the method of embodiment 1, wherein the intermittent reduction comprises intermittently pausing the delivery of the stimulant.

3. Another embodiment is the method of embodiment 1, wherein the intermittently reduced delivery temporarily ceases inducing the at least one natural response.

4. Another embodiment is the method of embodiment 1, wherein the intermittently reduced delivery prevents the stimulant from waking the individual.

5. Another embodiment is the method of embodiment 1, wherein providing the stimulant comprises automatically delivering the stimulant from a supply source while the individual is in a sleep state.

6. Another embodiment is the method of embodiment 1, wherein the natural response comprises an activity comprising at least one of salivation, forward movement of the tongue, repositioning of the tongue, swallowing and a combination thereof.

7. Another embodiment is the method of embodiment 6, wherein at least one of the activities reduces vibrations of a soft palate or uvula without waking the individual.

8. Another embodiment is the method of embodiment 1, wherein providing the stimulant includes positioning an oral appliance within the mouth having a delivery port that delivers the stimulant to the tongue.

9. Another embodiment is the method of embodiment 8, where positioning the oral appliance within the mouth comprises positioning the oral appliance on at least one of the lower front teeth such that the delivery port of the oral appliance is directly adjacent to the posterior side of the lower front teeth.

10. Another embodiment is the method of embodiment 8, where positioning the oral appliance within the mouth comprises positioning the oral appliance on at least one of the upper front teeth such that the delivery port of the oral appliance is directly adjacent to the posterior side of the upper front teeth.

11. Another embodiment is the method of embodiment 8, where the oral appliance comprises at least one of a mandibular advancement device, a continuous positive airway pressure device, a mouthguard, a custom molded mouthpiece, and a retainer.

12. Another embodiment is the method of embodiment 8, where the oral appliance comprises an internal reservoir fluidly coupled to the delivery port, the internal reservoir containing at least a portion of the stimulant, and where the delivery port comprises a valve, where providing the stimulant comprises opening of the valve to dispense the stimulant.

13. Another embodiment is the method of embodiment 1, where providing the stimulant comprises providing an external reservoir containing the stimulant.

14. Another embodiment is the method of embodiment 1, further comprising providing a second stimulant to trigger an olfactory response in the sleeping individual.

15. Another embodiment is the method of embodiment 1, where the stimulant comprises a substance comprising a taste selected from a group consisting of a sour taste, a citric taste, a sweet taste.

16. Another embodiment is the method of embodiment 1, where the stimulant comprises a taste selected from a group consisting of xylitol.

17. Another embodiment is the method of embodiment 1, where intermittently reducing delivery of the stimulant comprises reducing the stimulant delivery until a triggering signal returns an increased delivery of the stimulant.

18. Another embodiment is the method of embodiment 17, further comprising: a dispensing unit cooperating with a sensor; wherein the triggering signal is generated in response to the sensor; and wherein the dispensing unit is triggered to increase delivery of the stimulant in response to the triggering signal.

19. Another embodiment is the method of embodiment 17, wherein the dispensing unit is in electrical communication with the sensor.

20. Another embodiment is the method of embodiment 18, wherein the sensor comprises a sensor selected from the group consisting of a pressure sensor, an optical sensor, a sound sensor, a movement sensor, an electro-magnetic sensor.

21. Another embodiment is the method of embodiment 18, where the sensor is positioned in the mouth and generates a signal based on a movement or position of the tongue.

22. Another embodiment is the method of embodiment 18, where the amount of stimulant delivered is determined by the triggering signal.

23. Another embodiment is the method of embodiment 17, further comprising measuring a degree of tongue movement with the sensor and using the triggering signal to determine the amount of stimulant based on the degree of movement.

24. Another embodiment is the method of embodiment 1, where delivering the stimulant and intermittently reducing delivery of the stimulant are timed with an event comprising respiration, respiratory effect, respiratory flow, hypoxia, hypopnea, oxygen saturation, or pausing the stimulant until a triggering signal restarts delivery of the stimulant.

25. Another embodiment is a method for minimizing sleep disturbances in an individual, the method comprising: positioning a dispensing unit within a mouth of the individual, where the dispensing unit comprises at least one port adjacent to a tongue; providing a supply of a stimulant through the port that induces a biological response in the mouth of the individual; controlling delivery of the stimulant between a first delivery phase, in which the stimulant is delivered to the mouth to induce the biological response and a second delivery phase, during which delivery of the stimulant to the mouth is reduced form the first delivery phase.

26. Another embodiment is the method of embodiment 25, wherein the second delivery profile comprises substantially stopping delivery of the stimulant.

27. Another embodiment is the method of embodiment 25, wherein controlling delivery of the stimulant permits periodically inducing the biological response without waking the individual.

28. Another embodiment is the method of embodiment 25, wherein providing the supply of the stimulant comprises automatically dispensing the stimulant while the individual is in a sleep state.

29. Another embodiment is the method of embodiment 25, where providing the supply of the stimulant comprises metering the stimulant to induce the biological response without waking the patient.

30. Another embodiment is the method of embodiment 25, further comprising: containing at least a portion of the stimulant within an internal reservoir of the dispensing unit that is fluidly coupled with the port; and wherein providing the supply of the stimulant comprises dispensing the stimulant from the internal reservoir through the port.

31. Another embodiment is the method of embodiment 30, wherein providing the supply of the stimulant comprises opening a valve to dispense the stimulant from the internal reservoir through the port.

32. Another embodiment is the method of embodiment 30, wherein the supply of the stimulant is fully contained within the reservoir such that the dispensing unit is fully contained within the mouth.

33. Another embodiment is the method of embodiment 30, further comprising providing a remainder of the stimulant in an external reservoir that is fluidly coupled to the internal reservoir.

34. Another embodiment is the method of embodiment 25, further comprising: containing at least a portion of the stimulant within an external reservoir located outside of the dispensing device and mouth and that is fluidly coupled to the port; and delivering the stimulant comprises dispensing of the stimulant from the external reservoir through the port into the mouth.

35. Another embodiment is the method of embodiment 25, wherein the biological response comprises salivation, forward movement of the tongue, repositioning of the tongue, swallowing, or a combination thereof.

36. Another embodiment is the method of embodiment 25, wherein positioning the dispensing unit within the mouth comprises positioning the dispensing unit on at least one of the lower front teeth such that the delivery port of the dispensing unit is directly adjacent to the posterior side of the lower front teeth.

37. Another embodiment is the method of embodiment 25, wherein the dispensing unit comprises a mandibular advancement device, a continuous positive airway pressure device, a mouthguard, custom molded mouthpiece, or a retainer.

38. Another embodiment is the method of embodiment 25, further comprising providing a second stimulant to trigger an olfactory response in the sleeping individual.

39. Another embodiment is the method of embodiment 25, wherein the stimulant comprises a substance comprising a taste comprising at least one of a sour taste, a citric taste, and a sweet taste.

40. Another embodiment is the method of embodiment 25, wherein the stimulant comprises xylitol.

41. Another embodiment is the method of embodiment 25, further comprising providing a triggering signal to control delivery of the stimulant between the first delivery phase and the second delivery phase.

42. Another embodiment is the method of embodiment 41, further comprising: a sensor coupled to the dispensing unit; and wherein the triggering signal is generated in response to a parameter sensed by the sensor.

43. Another embodiment is the method of embodiment 42, wherein the dispensing unit comprises the sensor.

44. Another embodiment is the method of embodiment 42, where the sensor comprises a pressure sensor, an optical sensor, a sound sensor, a movement sensor, an EEG sensor, an EMG sensor, or an electro-magnetic sensor.

45. Another embodiment is the method of embodiment 42, further comprising positioning the sensor in the mouth and generating a signal based on a movement or position of the tongue or a movement or position of the jaw.

46. Another embodiment is the method of embodiment 42, where the amount of stimulant delivered is determined by the triggering signal.

47. Another embodiment is the method of embodiment 42, further comprising: measuring a degree of tongue movement with the sensor; and using the triggering signal to determine the amount of stimulant based on the degree of movement.

48. Another embodiment is the method of embodiment 42, further comprising: measuring a degree of jaw movement with the sensor; and using the triggering signal to determine the amount of stimulant based on the degree of movement.

49. Another embodiment is an oral device for dispensing a stimulant that produces a biological response within the mouth to reduce sleep disorder breathing in an individual, comprising: a device body having a dental cavity for removably nesting with one or more structures within the mouth; a dispensing port adjacent to an anterior portion of the dental cavity, such that when the device body is positioned within a mouth the dental cavity is adjacent to the teeth and the dispensing port is adjacent to a posterior surface of teeth such that the stimulant leaving the dispensing port draws the tongue adjacent or next to the posterior surface of the teeth; and a fluid reservoir fluidly coupled to the dispensing port and configured to contain and supply the stimulant to the dispensing port.

50. Another embodiment is the device of embodiment 49, wherein the device is further configured to allow for an intermittent change in the delivery of the stimulant from the reservoir to the mouth through the dispensing port.

51. Another embodiment is the device of embodiment 50, further comprising: a valve located in a fluid path between the fluid reservoir and the dispensing port; and wherein the valve is configured to allow intermittently changing the delivery profile of the stimulant through the dispensing port.

52. Another embodiment is the device of embodiment 49, further comprising a palatial nesting section adjacent to the dental cavity and configured to nest within an arch of a palate to improve retention of the device body within the mouth.

53. Another embodiment is the device of embodiment 49, further comprising: a control unit configured to control the intermittently changed delivery of the stimulant.

54. Another embodiment is the device of embodiment 53, wherein: the control unit is in coupled communication with the valve; and the control unit comprises a user interface to control operation of the valve.

55. Another embodiment is the device of embodiment 51, further comprising: at least one sensor electrically coupled to the valve; and wherein the sensor is configured to generate a triggering signal.

56. Another embodiment is the device of embodiment 55, wherein the sensor comprises a pressure sensor, an optical sensor, a sound sensor, a movement sensor, an EEG senor, an EMG sensor, or an electro-magnetic sensor.

57. Another embodiment is the device of embodiment 55, wherein the sensor is coupled to the device body in a manner such that it is located within the mouth when the device body is positioned in the mouth.

58. Another embodiment is the device of embodiment 57, wherein the sensor is attached to the device body.

59. Another embodiment is the device of embodiment 55, wherein the sensor is spaced from the device body such that the sensor can remain external to the mouth when the device body is positioned in the mouth.

60. Another embodiment is a method for improving sleep quality in a sleeping individual, comprising: providing a stimulant that induces a natural response within the mouth of the individual when in contact with a tongue of the individual; delivering the stimulant to the tongue in a manner configured to induce the natural response; temporarily reducing delivery of the stimulant in a manner configured to temporarily reduce inducing the natural response; and returning to increased delivery of the stimulant to again induce the natural response.

61. Another embodiment is the method of embodiment 60, wherein temporarily reducing delivery of the stimulant comprises ceasing delivery of the stimulant.

62. Another embodiment is the method of embodiment 61, wherein returning to increased delivery of the stimulant comprises restarting delivery of the stimulant.

63. Another embodiment is the method of embodiment 60, further comprising: limiting the amount of stimulant delivered to produce the biologic activity resulting in reducing vibrations of a soft palate or uvula without waking the individual.

64. Another embodiment is an oral device for producing a biological response within the mouth to reduce sleep disorder breathing in an individual, comprising: a device body having a dental cavity for removably nesting with one or more structures within the mouth; and a dispensing surface adjacent to an anterior portion of the dental cavity, such that when the device body is positioned within a mouth the dental cavity is adjacent to the teeth and the dispensing surface is adjacent to a posterior surface of the teeth, where the dispensing surface comprises a supply of a stimulant, where the stimulant is releasable from the dispensing surface over a period of time and draws a tongue adjacent to or next to the posterior surface of the teeth.

65. Another embodiment is a medical device system for delivering a therapy to a mouth or tongue of a subject, comprising: an oral device configured to be secured within the mouth in a secured configuration; a therapy coupled to the oral device; wherein the oral device in the secured configuration is configured to deliver the therapy into the mouth; and at least one of:
    the oral device in the secured configuration is configured to deliver the therapy at an anterior location within the mouth,
    the therapy comprises a source of therapeutic agent which is located at an external position outside of the mouth, and a delivery assembly is coupled to the source and also to the oral device and is configured to deliver the agent from the source in the external position to the oral device in the secured configuration, an active controller is configured to actively control a delivery profile of the therapy into the mouth via the oral device,
    a sensor is coupled to a sensor location on the oral device,
    the oral device comprises a palatal bridge-less mouthpiece with a dental cavity configured to nest on at least one tooth in the mouth; and
    a coating deposited on a dispensing surface of the oral device at a delivery location, the therapy comprises a therapeutic agent contained within the coating, and the coating is configured to release the therapeutic agent into the mouth at the delivery location.

66. Another embodiment is the system of embodiment 65, wherein the oral device in the secured configuration is configured to deliver the therapy at an anterior location within the mouth, 67. Another embodiment is the system of embodiment 66, wherein: the therapy comprises a source of therapeutic agent which is located at an external position outside of the mouth; and a delivery assembly is coupled to the source and also to the oral device and is configured to deliver the agent from the source in the external position to the oral device in the secured configuration.

68. Another embodiment is the system of embodiment 67, further comprising: an active controller that is configured to actively control a delivery profile of the therapy into the mouth via the oral device.

69. Another embodiment is the system of embodiment 68, further comprising: a sensor that is coupled to a sensor location on the oral device.

70. Another embodiment is the system of embodiment 69, wherein: the oral device comprises a palatal bridge-less mouthpiece with a dental cavity configured to nest on at least one tooth in the mouth.

71. Another embodiment is the system of embodiment 68, wherein: the oral device comprises a palatal bridge-less mouthpiece with a dental cavity configured to nest on at least one tooth in the mouth.

72. Another embodiment is the system of embodiment 67, further comprising: a sensor that is coupled to a sensor location on the oral device.

73. Another embodiment is the system of embodiment 72, wherein: the oral device comprises a palatal bridge-less mouthpiece with a dental cavity configured to nest on at least one tooth in the mouth.

74. Another embodiment is the system of embodiment 67, wherein: the oral device comprises a palatal bridge-less mouthpiece with a dental cavity configured to nest on at least one tooth in the mouth.

75. Another embodiment is the system of embodiment 66, further comprising: an active controller that is configured to actively control a delivery profile of the therapy into the mouth via the oral device at the anterior location.

76. Another embodiment is the system of embodiment 65, further comprising: a sensor that is coupled to a sensor location on the oral device.

77. Another embodiment is the system of embodiment 76, wherein: the oral device comprises a palatal bridge-less mouthpiece with a dental cavity configured to nest on at least one tooth in the mouth.

78. Another embodiment is the system of embodiment 75, wherein: the oral device comprises a palatal bridge-less mouthpiece with a dental cavity configured to nest on at least one tooth in the mouth.

79. Another embodiment is the system of embodiment 66, further comprising: a sensor that is coupled to a sensor location on the oral device.

80. Another embodiment is the system of embodiment 79, wherein: the oral device comprises a palatal bridge-less mouthpiece with a dental cavity configured to nest on at least one tooth in the mouth.

81. Another embodiment is the system of embodiment 66, wherein: the oral device comprises a palatal bridge-less mouthpiece with a dental cavity configured to nest on at least one tooth in the mouth.

82. Another embodiment is the system of embodiment 65, wherein: the therapy comprises a source of therapeutic agent that is located at an external position outside of the mouth; and a delivery assembly is coupled to the source and also to the oral device and is configured to deliver the agent from the source in the external position to the oral device in the secured configuration.

83. Another embodiment is the system of embodiment 82, further comprising: an active controller that is coupled to the delivery assembly and is configured to actively control a delivery profile of the delivered agent into the mouth via the delivery assembly and oral device.

84. Another embodiment is the system of embodiment 83, further comprising: a sensor that is coupled to a sensor location on the oral device.

85. Another embodiment is the system of embodiment 84, wherein: the oral device comprises a palatal bridge-less mouthpiece with a dental cavity configured to nest on at least one tooth in the mouth.

86. Another embodiment is the system of embodiment 83, wherein: the oral device comprises a palatal bridge-less mouthpiece with a dental cavity configured to nest on at least one tooth in the mouth.

87. Another embodiment is the system of embodiment 82, further comprising: a sensor that is coupled to a sensor location on the oral device.

88. Another embodiment is the system of embodiment 87, wherein: the oral device comprises a palatal bridge-less mouthpiece with a dental cavity configured to nest on at least one tooth in the mouth.

89. Another embodiment is the system of embodiment 82, wherein: the oral device comprises a palatal bridge-less mouthpiece with a dental cavity configured to nest on at least one tooth in the mouth.

90. Another embodiment is the system of embodiment 65, further comprising: an active controller that is configured to actively control a delivery profile of the therapy into the mouth via the oral device.

91. Another embodiment is the system of embodiment 90, further comprising: a sensor that is coupled to a sensor location on the oral device.

92. Another embodiment is the system of embodiment 91, wherein: the oral device comprises a palatal bridge-less mouthpiece with a dental cavity configured to nest on at least one tooth in the mouth.

93. Another embodiment is the system of embodiment 90, wherein: the oral device comprises a palatal bridge-less mouthpiece with a dental cavity configured to nest on at least one tooth in the mouth.

94. Another embodiment is the system of embodiment 65, further comprising: a sensor that is coupled to a sensor location on the oral device.

95. Another embodiment is the system of embodiment 94, wherein: the oral device comprises a palatal bridge-less mouthpiece with a dental cavity configured to nest on at least one tooth in the mouth.

96. Another embodiment is the system of embodiment 65, wherein: the oral device comprises a palatal bridge-less mouthpiece with a dental cavity configured to nest on at least one tooth in the mouth.

97. A medical device system for delivering a therapy to a mouth or tongue of a subject, comprising: a tongue position stimulator (TST) assembly configured to deliver a stimulus to the tongue so as to stimulate the tongue into a position; and a tongue position sensor (TSE) assembly configured to sense a location of the tongue at the position.

98. Another embodiment is the system of embodiment 97, further comprising: an oral device configured to be secured within the mouth in a secured configuration; wherein the TST comprises a stimulus coupled to the oral device at a delivery location, and is configured to deliver the stimulus to the mouth or tongue in the secured configuration so as to stimulate the tongue to the position; and wherein the TSE comprises a sensor coupled to the oral device at a sensor location and configured to sense a tongue position corresponding with the sensor location.

99. Another embodiment is the system of embodiment 98, further characterized by at least one of:
the TST assembly is configured to deliver the stimulus into the mouth at an anterior location within the mouth via the oral device in the secured configuration;
the TST assembly further comprises a source of therapeutic agent which comprises a stimulant, and a delivery assembly configured to couple to the source at an external location outside the mouth and also to the oral device in the secured configuration, and is configured to deliver the agent from the source at the external location to the oral device in the secured configuration in the mouth;
the TST assembly comprises an active controller that is configured to actively control a delivery profile of the delivered agent into the mouth via the oral device; and
the oral device comprises a palatal bridge-less mouthpiece with a dental cavity configured to nest on at least one tooth in the mouth.

100. Another embodiment is the system of embodiment 99, wherein: the TST assembly is configured to deliver the therapy into the mouth at an anterior location within the mouth via the oral device in the secured configuration.

101. Another embodiment is the system of embodiment 99, wherein the TST assembly further comprises: a source of therapeutic agent which comprises a stimulant; and a delivery assembly configured to couple to the source at an external location outside the mouth and also to the oral device in the secured configuration, and is configured to deliver the agent from the source at the external location to the oral device in the secured configuration in the mouth.

102. Another embodiment is the system of embodiment 99, wherein the TST assembly further comprises: an active controller that is configured to actively control a delivery profile of the delivered agent into the mouth via the oral device.

103. Another embodiment is the system of embodiment 99, wherein the oral device comprises: a palatal bridge-less mouthpiece with a dental cavity configured to nest on at least one tooth in the mouth.

104. Other embodiments comprise the systems of any one of embodiments 65-103, wherein the oral device is configured to be permanently or semi-permanently implanted in the secured configuration in the mouth.

105. Other embodiments comprise the systems of any one of embodiments 65-103, wherein the oral device is configured to be temporarily implanted in the secured configuration mouth and is removable from the secured configuration.

106. Other embodiments comprise the systems of any one of embodiments 65-103, wherein the oral device comprises a mouthpiece with at least one wall defining at least one dental cavity that is configured to nest on at least one tooth in the mouth.

107. Another embodiment is the system of embodiment 106, wherein the mouthpiece comprises at least two opposite walls with a space therebetween, said space defining at least in part the dental cavity.

108. Another embodiment is the system of embodiment 106, wherein the at least one dental cavity is configured to nest on multiple teeth in the mouth.

109. Another embodiment is the system of embodiment 108, wherein the mouthpiece is molded to form-fit onto the teeth of the subject.

110. Another embodiment is the system of embodiment 106, wherein the at least one tooth comprises an incisor.

111. Another embodiment is the system of any one of embodiments 65-103, wherein: the therapy comprises a source of therapeutic agent; a first delivery port is located at a first port location on the oral device coinciding at or adjacent to an incisor in the secured configuration; and the therapeutic agent is coupled for delivery into the mouth at the first delivery port.

112. Another embodiment is the system of embodiment 111, wherein the first port location coincides at or adjacent to at least one of the two middle incisors in the front of the mouth.

113. Another embodiment is the system of embodiment 111, wherein: the source comprises a reservoir; the therapeutic agent comprises a volume of a fluid material; and a delivery tube is fluidly coupled to the reservoir and also to the delivery port so as to provide for fluid delivery of the fluid material from the reservoir to the delivery port.

114. Other embodiments comprise the systems of any one of embodiments 65-103, wherein the therapy comprises a stimulant.

115. Another embodiment is the system of embodiment 114, wherein the stimulant comprises a delivered energy.

116. Another embodiment is the system of embodiment 115, wherein the delivered energy comprises electricity.

117. Another embodiment is the system of embodiment 116, wherein the delivered energy comprises an RF current.

118. Another embodiment is the system of embodiment 115, wherein the delivered energy comprises thermal energy.

119. Another embodiment is the system of embodiment 115, wherein the delivered energy comprises light energy.

120. Another embodiment is the system of embodiment 114, wherein the stimulant comprises a cryogenic cooling stimulant.

121. Another embodiment is the system of embodiment 114, wherein the stimulant comprises a material.

122. Another embodiment is the system of embodiment 121, wherein the material comprises a fluid.

123. Another embodiment is the system of embodiment 122, wherein the fluid comprises a liquid.

124. Another embodiment is the system of embodiment 122, wherein the fluid comprises a gas.

125. Another embodiment is the system of embodiment 121, wherein the material comprises a flavor.

126. Another embodiment is the system of embodiment 121, wherein the material comprises a taste.

127. Another embodiment is the system of embodiment 121, wherein the material comprises a smell.

128. Another embodiment is the system of embodiment 121, wherein the material comprises a liquid taste stimulant.

129. Another embodiment is the system of embodiment 121, wherein the material comprises a sweet taste.

130. Another embodiment is the system of embodiment 129, wherein the sweet taste comprises a sugar, or a pre-cursor, analog, or derivative thereof.

131. Another embodiment is the system of embodiment 130, wherein the sugar comprises xylitol, or a pre-cursor, analog, or derivative thereof.

132. Another embodiment is the system of embodiment 130, wherein the material comprises a liquid.

133. Another embodiment is the system of embodiment 114, wherein the stimulant comprises a mechanical stimulant.

134. Another embodiment is the system of embodiment 114, wherein the stimulant comprises a texture stimulant.

135. Another embodiment is the system of embodiment 114, wherein the stimulant comprises a tongue stimulant characterized as stimulating a tongue repositioning activity in response to exposure to the stimulant.

136. Other embodiments include the systems of any of embodiments 65-66, 75-81, 90-98, or 100-103, wherein: the therapy comprises a source of therapeutic agent; the source comprises a reservoir; and the therapeutic agent comprises a therapeutic material within the reservoir.

137. Another embodiment is the system of embodiment 136, wherein: the reservoir is located in the oral device.

138. Another embodiment is the system of embodiment 136, wherein: the reservoir is located separately from the oral device at an external location outside the mouth when the oral device is in the secured configuration; and a delivery assembly is coupled to the reservoir and also to the oral device and is configured to deliver the therapeutic material from the reservoir in the external location to the mouth via the oral device in the secured configuration.

139. Other embodiments include the systems of any of embodiments 65-103, wherein: the therapy comprises a source of therapeutic agent; and the active controller comprises a pump coupled to a reservoir containing the therapeutic agent and that is configured to pump the agent according to the controlled delivery profile into the mouth via the oral device.

140. Other embodiments include the systems of any of embodiments 65-103, wherein the controlled delivery profile comprises a constant delivery rate of the therapy over a time period.

141. Another embodiment is the system of embodiment 140, wherein the time period is configured to coincide with a sleep period for the subject.

142. Other embodiments include the systems of any one of embodiments 65-103, wherein the controlled delivery profile comprises a changing delivery rate of the therapy over time between at least a first rate and a second rate that is below the first rate.

143. Another embodiment is the system of embodiment 142, wherein the time period is configured to coincide with a sleep period for the subject.

144. Another embodiment is the system of embodiment 142, wherein the changing delivery rate comprises a cycle between the first and second rates over the time.

145. Another embodiment is the system of embodiment 144, wherein the first and second rates comprise on and off conditions.

146. Another embodiment is the system of embodiment 145, wherein the on and off conditions are relative to a threshold for achieving a therapeutic result in the subject, such that the first rate comprising the on condition is above the threshold, and the second rate comprising the off condition is below the threshold.

147. Another embodiment is the system of embodiment 146, wherein the second rate comprising the off condition comprises a substantially zero rate and non-delivery of the therapy.

148. Another embodiment is the system of embodiment 146, wherein the second rate comprising the off condition comprises a non-zero rate of delivering the therapy below the threshold.

149. Another embodiment is the system of embodiment 144, wherein the cycle comprises a substantial step cycle between the first and second rates.

150. Another embodiment is the system of embodiment 145, wherein the cycle comprises a ramping cycle between the first and second rates.

151. Other embodiments include the systems of any of embodiments 65-103, wherein the active controller further comprises: a driver for driving the delivery of the therapy to the oral device; an input set of instructions for controlling the delivery according to the controlled delivery profile, and a processor configured to receive the input set of instructions and coupled to the driver to actuate the driver to drive the delivery of the therapy according to the instructions.

152. Another embodiment is the system of embodiment 151, wherein the processor is configured to receive the set of instructions at least in part by a manual input by a user of the system.

153. Another embodiment is the system of embodiment 151, further comprising: a software program embedded in a non-transitory computer readable medium that contains the at least a portion of the set of instructions; wherein the processor is configured to run the software program to receive at least the portion of the set of instructions.

154. Another embodiment is the system of embodiment 153, wherein the active controller further comprises a sensor input configured to receive sensed information from a sensor coupled to the subject, and the set of instructions are variable in response to the sensed information received.

155. Another embodiment is the system of embodiment 154, wherein the sensed information relates to a tongue position in the mouth of the subject.

156. Other embodiments include the systems of any of embodiments 65-103, further comprising: a light source optically coupled to transmit an illumination light signal into the mouth at an illumination port on the oral device; and wherein the sensor comprises an optical sensor configured to sense a reflected light signal reflected in the mouth from the illumination light signal transmitted into the mouth.

157. Another embodiment is the system of embodiment 156, wherein the sensor is configured to sense a position of the tongue against the sensor location based at least in part upon a change in light from the light source that is reflected from the first end.

158. Other embodiments include the systems of any of embodiments 65-103, wherein the sensor comprises a pressure sensor.

159. Another embodiment is the system of embodiment 158, wherein the pressure sensor comprises an optical pressure sensor.

160. Another embodiment is the system of embodiment 158, wherein the pressure sensor comprises a pneumatic or hydraulic pressure sensor.

161. Another embodiment is the system of embodiment 158, wherein the pressure sensor comprises a strain gauge pressure sensor.

162. Other embodiments include the systems of any of embodiments 65-103, wherein the sensor is configured to sense a position of the tongue in the mouth.

163. Another embodiment is the system of embodiment 162, wherein the position comprises an anterior portion of the mouth.

164. Another embodiment is the system of embodiment 163, wherein the anterior position is at or adjacent to the front incisors in the mouth.

165. Another embodiment is the system of embodiment 164, wherein the anterior position is at or adjacent to the front top incisors in the mouth.

166. Other embodiments include the systems of any of embodiments 65-103, wherein the sensor is configured to sense an applied force at the sensor location.

167. Another embodiment is the system of embodiment 166, wherein the sensor location is on a lingual side of the teeth, and the applied force is from the tongue.

168. Other embodiments include the system of any of embodiments 65-103, wherein: the oral device comprises a mouthpiece with at least one dental cavity configured to nest on multiple teeth in the mouth comprising at least the two middle front incisors; the source of therapeutic agent comprises a reservoir containing a volume of fluid flavor, taste, or smell stimulant; the delivery assembly comprises a fluid delivery tube that is fluidly coupled to the reservoir at the external location outside of the mouth and also to a delivery port located at a delivery port location on the mouthpiece coinciding with at least one of the incisor teeth in the secured configuration; and the active controller comprises a pump configured to actively control a delivery profile of the stimulant from the reservoir via the delivery assembly to the mouthpiece and through the delivery port into the mouth.

169. Another embodiment is the system of embodiment 168, and further wherein; the therapy comprises a stimulated repositioning of the tongue to the anterior location in response to the controlled delivery of the stimulant into the mouth.

170. Another embodiment is a method for delivering a therapy to a mouth or tongue of a subject, comprising: securing an oral device within the mouth in a secured configuration; coupling a therapy to the oral device; delivering the therapy into the mouth via the oral device; and at least one of:
delivering the therapy at an anterior location within the mouth via the oral device in the secured configuration,
providing a source of a therapeutic agent at an external position outside of the mouth, coupling the source in the external position to the oral device in the secured configuration via a delivery assembly, and delivering the agent from the source in the external position to the oral device in the secured configuration via the delivery assembly,
actively controlling a delivery profile of the therapy into the mouth via the oral device in the secured configuration,
sensing a parameter within the mouth with a sensor at a sensor location on the oral device in the secured configuration;
securing the oral device in the secured configuration by nesting a dental cavity of a palatal bridge-less mouthpiece on at least one tooth in the mouth; and
coupling the therapy to the oral device by coating a therapeutic agent onto a dispensing surface of the oral device, and delivering the therapy into the mouth by releasing the therapeutic agent into the mouth via the coating.

171. Another embodiment is the method of embodiment 170, further comprising: delivering the therapy at an anterior location within the mouth via the oral device in the secured configuration.

172. Another embodiment is the method of embodiment 171, further comprising: positioning a source of therapeutic agent at an external position outside of the mouth; and coupling the source to the oral device in the secured configuration via a delivery assembly; and delivering the therapy by delivering the agent from the source in the external position to the oral device in the secured configuration via the delivery assembly.

173. Another embodiment is the method of embodiment 172, further comprising: actively controlling a delivery profile of the therapy into the mouth via the oral device in the secured configuration.

174. Another embodiment is the method of embodiment 173, further comprising: sensing a parameter within the mouth with a sensor at a sensor location on the oral device in the secured configuration.

175. Another embodiment is the method of embodiment 174, further comprising: securing the oral device in the secured configuration by nesting a dental cavity of a palatal bridge-less mouthpiece on at least one tooth in the mouth.

176. Another embodiment is the method of embodiment 173, further comprising: securing the oral device in the secured configuration by nesting a dental cavity of a palatal bridge-less mouthpiece on at least one tooth in the mouth.

177. Another embodiment is the method of embodiment 172, further comprising: sensing a parameter within the mouth with a sensor at a sensor location on the oral device in the secured configuration.

178. Another embodiment is the method of embodiment 177, further comprising: securing the oral device in the secured configuration by nesting a dental cavity of a palatal bridge-less mouthpiece on at least one tooth in the mouth.

179. Another embodiment is the method of embodiment 172, wherein: securing the oral device in the secured configuration by nesting a dental cavity of a palatal bridge-less mouthpiece on at least one tooth in the mouth.

180. Another embodiment is the method of embodiment 171, further comprising: actively controlling a delivery profile of the therapy into the mouth via the oral device in the secured configuration.

181. Another embodiment is the method of embodiment 170, further comprising: sensing a parameter within the mouth with a sensor at a sensor location on the oral device in the secured configuration.

182. Another embodiment is the method of embodiment 181, further comprising: securing the oral device in the secured configuration by nesting a dental cavity of a palatal bridge-less mouthpiece on at least one tooth in the mouth.

183. Another embodiment is the method of embodiment 180, further comprising: securing the oral device in the secured configuration by nesting a dental cavity of a palatal bridge-less mouthpiece on at least one tooth in the mouth.

184. Another embodiment is the method of embodiment 171, further comprising: sensing a parameter within the mouth with a sensor at a sensor location on the oral device in the secured configuration.

185. Another embodiment is the method of embodiment 184, wherein: securing the oral device in the secured configuration by nesting a dental cavity of a palatal bridge-less mouthpiece on at least one tooth in the mouth.

186. Another embodiment is the method of embodiment 171, wherein: securing the oral device in the secured configuration by nesting a dental cavity of a palatal bridge-less mouthpiece on at least one tooth in the mouth.

187. Another embodiment is the method of embodiment 170, wherein: positioning a source of therapeutic agent at an external position outside of the mouth; and coupling the source to the oral device in the secured configuration via a delivery assembly; and delivering the therapy by delivering the agent from the source in the external position to the oral device in the secured configuration via the delivery assembly.

188. Another embodiment is the method of embodiment 187, further comprising: actively controlling a delivery profile of the therapy into the mouth via the oral device in the secured configuration.

189. Another embodiment is the method of embodiment 188, further comprising: sensing a parameter within the mouth with a sensor at a sensor location on the oral device in the secured configuration.

190. Another embodiment is the method of embodiment 189, wherein: securing the oral device in the secured configuration by nesting a dental cavity of a palatal bridge-less mouthpiece on at least one tooth in the mouth.

191. Another embodiment is the method of embodiment 188, wherein: securing the oral device in the secured configuration by nesting a dental cavity of a palatal bridge-less mouthpiece on at least one tooth in the mouth.

192. Another embodiment is the method of embodiment 187, further comprising: sensing a parameter within the mouth with a sensor at a sensor location on the oral device in the secured configuration.

193. Another embodiment is the method of embodiment 192, wherein: securing the oral device in the secured configuration by nesting a dental cavity of a palatal bridge-less mouthpiece on at least one tooth in the mouth.

194. Another embodiment is the method of embodiment 187, wherein: securing the oral device in the secured configuration by nesting a dental cavity of a palatal bridge-less mouthpiece on at least one tooth in the mouth.

195. Another embodiment is the method of embodiment 170, further comprising: actively controlling a delivery profile of the therapy into the mouth via the oral device in the secured configuration.

196. Another embodiment is the method of embodiment 195, further comprising: sensing a parameter within the mouth with a sensor at a sensor location on the oral device in the secured configuration.

197. Another embodiment is the method of embodiment 196, wherein: securing the oral device in the secured configuration by nesting a dental cavity of a palatal bridge-less mouthpiece on at least one tooth in the mouth.

198. Another embodiment is the method of embodiment 195, wherein: securing the oral device in the secured configuration by nesting a dental cavity of a palatal bridge-less mouthpiece on at least one tooth in the mouth.

199. Another embodiment is the method of embodiment 170, further comprising: sensing a parameter within the mouth with a sensor at a sensor location on the oral device in the secured configuration.

200. Another embodiment is the method of embodiment 199, wherein: securing the oral device in the secured configuration by nesting a dental cavity of a palatal bridge-less mouthpiece on at least one tooth in the mouth.

201. Another embodiment is the method of embodiment 170, wherein: securing the oral device in the secured configuration by nesting a dental cavity of a palatal bridge-less mouthpiece on at least one tooth in the mouth.

202. A method for delivering a therapy to a mouth or tongue of a subject, comprising: delivering a stimulus to the tongue via a tongue position stimulator (TST) assembly; stimulating the tongue into a position by delivering the stimulus; and sensing a location of the tongue at the position via a tongue position sensor (TSE) assembly.

203. Another embodiment is the method of embodiment 202, further comprising: securing an oral device within the mouth in a secured configuration; wherein the TST assembly delivers the stimulus at a delivery location on the oral device in the secured configuration; and wherein the TSE assembly senses the tongue location at the position via a sensor coupled to the oral device at a sensor location corresponding with the position in the secured configuration.

204. Another embodiment is the method of embodiment 203, wherein delivering the stimulus via the TST is further characterized by at least one of:
delivering the stimulus at an anterior location within the mouth via the oral device in the secured configuration;
coupling a source of therapeutic agent comprising a stimulant at an external location outside the mouth to the oral device in the secured configuration via a delivery assembly, and delivering the agent with the delivery assembly from the source at the external location and to the oral device in the secured configuration and into the mouth;
actively controlling a delivery profile of the delivered agent into the mouth via the oral device in the secured configuration;
securing the oral device in the secured configuration by nesting dental cavity of a palatal bridge-less mouthpiece on at least one tooth in the mouth; and
coating the therapeutic agent onto a dispensing surface of the oral device, and releasing the therapeutic agent from the coating into the mouth.

205. Another embodiment is the method of embodiment 204, wherein delivering the stimulus via the TST is further characterized by: delivering the stimulus at an anterior location within the mouth via the oral device in the secured configuration.

206. Another embodiment is the method of embodiment 204, wherein delivering the stimulus via the TST is further characterized by: coupling a source of therapeutic agent comprising a stimulant at an external location outside the mouth to the oral device in the secured configuration via a delivery assembly; and delivering the agent with the delivery assembly from the source at the external location and to the oral device in the secured configuration and into the mouth.

207. Another embodiment is the method of embodiment 204, wherein delivering the stimulus via the TST is further characterized by: actively controlling a delivery profile of the delivered agent into the mouth via the oral device in the secured configuration.

208. Another embodiment is the method of embodiment 204, wherein delivering the stimulus via the TST is further characterized by: securing the oral device in the secured configuration by nesting dental cavity of a palatal bridge-less mouthpiece on at least one tooth in the mouth.

209. Other embodiments include the methods of any of embodiments 170-208, further comprising: permanently or semi-permanently implanting the oral device in the secured configuration in the mouth.

210. Other embodiments include the methods of any of embodiments 170-208, further comprising: removably securing the oral device in the secured configuration during a sleep period; and removing the removably secured oral device from the secured configuration following termination of the sleep period.

211. Other embodiments include the methods of any of embodiments 170-208, further comprising: securing the oral device in the secured configuration in the mouth by nesting at least one wall defining at least one dental cavity on at least one tooth in the mouth.

212. Another embodiment is the method of embodiment 211, further comprising: positioning the at least one tooth within at least one space between at least two opposite walls defining at least in part the dental cavity.

213. Another embodiment is the method of embodiment 211, further comprising nesting the at least one wall defining the at least one dental cavity on multiple teeth in the mouth.

214. Another embodiment is the method of embodiment 213, further comprising molding a mouthpiece to form-fit onto the multiple teeth.

215. Another embodiment is the method of embodiment 211, wherein the at least one tooth comprises an incisor.

216. Another embodiment is the method of any one of embodiments 170-208 above, wherein delivering the therapy via the TST assembly is further characterized by: providing a source of therapeutic agent; positioning a first delivery port that is located at a first port location on the oral device to coincide at or adjacent to an incisor in the secured configuration; and coupling the therapeutic agent to the first delivery port and delivering the agent through the first delivery port at the first port location in the secured configuration.

217. Another embodiment is the method of embodiment 216, further comprising: positioning the first port location to coincide at or adjacent to at least one of the two middle incisors in the front of the mouth in the secured configuration.

218. Another embodiment is the method of embodiment 216, wherein delivering the therapy via the TST is further characterized by: providing the source of therapeutic agent in a reservoir; providing the therapeutic agent as a volume of a fluid material; and fluidly coupling the reservoir to the delivery port via a delivery passageway therebetween; and causing the fluid material to flow from the reservoir, along the delivery passageway, and through the delivery port into the mouth.

219. Other embodiments include the methods of any of embodiments 170-208, wherein delivering the therapy comprises delivering a stimulant.

220. Another embodiment is the method of embodiment 219, wherein the delivering the stimulant comprises delivering energy.

221. Another embodiment is the method of embodiment 220, wherein delivering the energy comprises delivering an electrical current.

222. Another embodiment is the method of embodiment 221, wherein the delivered the electrical current comprises delivering a radiofrequency (RF) current.

223. Another embodiment is the method of embodiment 220, wherein delivering the energy comprises delivering thermal energy.

224. Another embodiment is the method of embodiment 220, wherein delivering the energy comprises delivering light energy.

225. Another embodiment is the method of embodiment 219, wherein delivering the stimulant comprises delivering a cryogenic cooling stimulant.

226. Another embodiment is the method of embodiment 219, wherein delivering the stimulant comprises delivering a material.

227. Another embodiment is the method of embodiment 226, wherein the delivering the material comprises delivering a fluid.

228. Another embodiment is the method of embodiment 227, wherein delivering the fluid comprises delivering a liquid.

229. Another embodiment is the method of embodiment 227, wherein delivering the fluid comprises delivering a gas.

230. Another embodiment is the method of embodiment 226, wherein delivering the material comprises delivering a flavor.

231. Another embodiment is the method of embodiment 226, wherein delivering the material comprises delivering a taste.

232. Another embodiment is the method of embodiment 226, wherein delivering the material comprises delivering a smell.

233. Another embodiment is the method of embodiment 226, wherein delivering the material comprises delivering a liquid taste stimulant.

234. Another embodiment is the method of embodiment 226, wherein delivering the material comprises delivering a sweet taste.

235. Another embodiment is the method of embodiment 234, wherein delivering the sweet taste comprises delivering a sugar, or a pre-cursor, analog, or derivative thereof.

236. Another embodiment is the method of embodiment 235, wherein delivering the sugar comprises delivering xylitol, or a pre-cursor, analog, or derivative thereof.

237. Another embodiment is the method of embodiment 235, wherein delivering the material comprises delivering a liquid.

238. Another embodiment is the method of embodiment 219, wherein the delivering the stimulant comprises providing a mechanical stimulant.

239. Another embodiment is the method of embodiment 219, wherein delivering the stimulant comprises delivering a texture stimulant.

240. Another embodiment is the method of embodiment 219, wherein delivering the stimulant comprises delivering a tongue stimulant characterized as stimulating a tongue repositioning activity in response to exposure to the stimulant.

241. Another embodiment is a method of any one of embodiments 170-171, 180-186, 195-203, or 205-208 above, further comprising: providing a source of therapeutic agent which comprises a therapeutic material in a reservoir; delivering the therapy is further characterized by delivering the therapeutic material from the reservoir into the mouth via the oral device in the secured configuration.

242. Another embodiment is the method of embodiment 241, further comprising: positioning the reservoir in the oral device and in the mouth in the secured configuration.

243. Another embodiment is the method of embodiment 241, further comprising: positioning the reservoir to be located separately from the oral device at an external location outside the mouth when the oral device is in the secured configuration; and using a delivery assembly to couple the externally positioned reservoir to the oral device, and to deliver the therapeutic material from the reservoir in the external location to the mouth via the oral device, while the oral device is in the secured configuration.

244. Other embodiments include the methods of any of embodiments 170-208, further comprising: providing the therapy to comprise a source of therapeutic agent in a reservoir; and coupling a pump to an active controller and also to the reservoir; actively controlling the pump via the active controller to deliver the agent with a controlled delivery profile from the reservoir and to the oral device in the secured configuration and into the mouth.

245. Other embodiments include the methods of any of embodiments 170-208, further comprising: delivering the therapy with a controlled delivery profile which comprises a constant delivery rate of the therapy over a time period.

246. Another embodiment is the method of embodiment 245, further comprising configuring the time period to coincide with a sleep period for the subject.

247. Other embodiments include the methods of any of embodiments 170-208, further comprising: delivering the therapy with a controlled delivery profile that comprises a changing delivery rate of the therapy over time between at least a first rate and a second rate that is below the first rate.

248. Another embodiment is the method of embodiment 247, further comprising configuring the time period to coincide with a sleep period for the subject.

249. Another embodiment is the method of embodiment 247, further comprising configuring the changing delivery rate to comprise a cycle between the first and second rates over the time.

250. Another embodiment is the method of embodiment 249, further comprising configuring the first and second rates to comprise on and off conditions, respectively.

251. Another embodiment is the method of embodiment 250, further comprising configuring the on and off conditions relative to a therapy delivery threshold for achieving a therapeutic result in the subject, such that the first rate comprising the on condition is configured to comprise delivering the therapy above the threshold, and the second rate comprising the off condition is configured to comprise delivering the therapy below the threshold.

252. Another embodiment is the method of embodiment 251, wherein the off condition of the second rate comprises a substantially zero rate and non-delivery of the therapy.

253. Another embodiment is the method of embodiment 251, wherein the off condition of the second rate comprises a non-zero rate of therapy delivery that is below the threshold.

254. Another embodiment is the method of embodiment 249, wherein the cycle comprises a substantial step cycle between the first and second rates.

255. Another embodiment is the method of embodiment 250, wherein the cycle comprises a ramping cycle between the first and second rates.

256. Other embodiments include the methods of any of embodiments 170-208, wherein actively controlling the therapy delivery is further characterized by: using a driver for driving the delivery of the therapy to the oral device; providing an input set of instructions for controlling the delivery according to the controlled delivery profile, configuring a processor to receive the input set of instructions; and coupling the processor to the driver to actuate the driver to drive the delivery of the therapy according to the instructions.

257. Another embodiment is the method of embodiment 256, further comprising manually inputting the instructions to the processor.

258. Another embodiment is the method of embodiment 256, further comprising: providing a software program embedded in a non-transitory computer readable medium and that comprises at least a portion of the set of instructions; and configuring the processor to run the software program to receive at least the portion of the set of instructions.

259. Another embodiment is the method of embodiment 258, further comprising providing or receiving sensed information from a sensor coupled to the subject, and varying the set of instructions in response to the sensed information received.

260. Another embodiment is the method of embodiment 259, wherein the sensed information relates to a tongue position in the mouth of the subject.

261. Other embodiments include the methods of any of embodiments 170-208, further comprising: transmitting a light signal into the mouth from a light source optically coupled to an illumination port on the oral device; and sensing a reflected light signal reflected in the mouth from the illumination light signal transmitted into the mouth via a light sensor at a sensor location on the oral device.

262. Another embodiment is the method of embodiment 261, wherein the sensing comprises sensing a position of the tongue against the sensor location based at least in part upon a change in light from the light source that is reflected at the sensor location.

263. Other embodiments include the methods of any of embodiments 170-208, wherein the sensing comprises a sensing a pressure with a pressure sensor.

264. Another embodiment is the method of embodiment 263, wherein the pressure sensor comprises an optical pressure sensor.

265. Another embodiment is the method of embodiment 263, wherein the pressure sensor comprises a pneumatic or hydraulic pressure sensor.

266. Another embodiment is the method of embodiment 263, wherein the pressure sensor comprises a strain gauge pressure sensor.

267. Other embodiments include the methods of any of embodiments 170-208, further comprising sensing a position of the tongue in the mouth.

268. Another embodiment is the method of embodiment 267, wherein the position comprises an anterior portion of the mouth.

269. Another embodiment is the method of embodiment 268, wherein the anterior position is at or adjacent to the front incisors in the mouth.

270. Another embodiment is the method of embodiment 269, wherein the anterior position is at or adjacent to the front top incisors in the mouth.

271. Other embodiments include the methods of any of embodiments 170-208, further comprising sensing an applied force at a sensor location in the mouth.

272. Another embodiment is the method of embodiment 271, wherein the sensor location is on a lingual side of the teeth, and the applied force is from the tongue.

273. Another embodiment is the method of any one of embodiments 170-208, further comprising: nesting at least one dental cavity of a mouthpiece of the oral device on multiple teeth comprising at least the two middle front incisors in the mouth; providing a source of therapeutic agent to comprise a volume of fluid flavor, taste, or smell stimulant material in a reservoir positioned at an external location outside of the mouth; using a fluid delivery tube to fluidly couple the reservoir at the external location outside of the mouth to a delivery port located at a delivery port location on the mouthpiece coinciding with at least one of the incisor teeth in the secured configuration; and actively controlling the therapy delivery via a controlled pump with a delivery profile of stimulant from the reservoir via the delivery assembly to the mouthpiece and through the delivery port into the mouth.

274. Another embodiment is the method of embodiment 273, wherein delivering the therapy further comprises; stimulating a repositioning of the tongue to the anterior location in response to the controlled delivery of the stimulant into the mouth.

275. Another embodiment is a method of any of embodiments 170-208, further comprising: treating a sleep disorder with the therapy delivery.

276. Another embodiment is the method of embodiment 275, wherein treating the sleep disorder comprises treating obstructive sleep apnea or snoring with the therapy delivery.

277. Other embodiments include the method, device, and system embodiments elsewhere herein described, but includes constant or near constant delivery of the fluid or material containing the stimulant, but diluting or adjusting the stimulant in the fluid or material so that the response is insufficient to wake the individual. For example, in cases where the stimulant is a taste, smell, or flavor stimulant, the stimulant can be diluted in a solution where the concentration is held high enough to cause the desired response but low enough to avoid waking the patient and is continuously delivered over a period of time. This stimulant concentration in the delivery vehicle (e.g. fluid or other material), or conversely its dilution, may be varied over time to change the stimulant component being delivered, and thus biologic stimulation, as considered consistent with and falling within the other aspects of the present disclosure exemplified by the detailed embodiments.

288. Another embodiment is a method for treating sleep disorder breathing in a sleeping individual, the method comprising: providing a stimulant that induces at least one natural response within a mouth of the sleeping individual when the stimulant enters the mouth; delivering the stimulant at a location posteriorly adjacent to one or more teeth in the mouth to induce at least one natural response to reduce sleep disorder breathing and improve the ability of the sleeping individual to maintain a sleep state; and controlling delivery of the stimulant, where controlling delivery prevents the stimulant from waking the individual.

289. Another embodiment is the method of embodiment 288, further comprising actively controlling the stimulant delivery with an active controller.

290. Another embodiment is a method for minimizing sleep disturbances in an individual, the method comprising: positioning a dispensing unit within a mouth of the individual, where the dispensing unit comprises at least one port adjacent to a tongue; providing a supply of a stimulant through the port that induces a biological response in the mouth of the individual; controlling delivery of the stimulant; and wherein the controlled delivery of the stimulant is configured to induce the biological response without waking the individual.

291. Another embodiment is an oral dispensing device for dispensing a stimulant that produces a biological response within a mouth or airway to reduce sleep disorder breathing in an individual, the oral dispensing device comprising: a supply of a stimulant solution comprising a stimulant at a concentration configured to cause a biological response when the stimulant solution is delivered in the mouth above a threshold delivery rate; a device body having a dental cavity for removably nesting with one or more structures within the mouth; a dispensing port adjacent to an anterior portion of the dental cavity, such that when the device body is positioned within a mouth the dental cavity is adjacent to the teeth and the dispensing port is adjacent to a posterior surface of teeth such that the stimulant solution leaving the dispensing port draws the tongue adjacent or next to the posterior surface of the teeth; a fluid reservoir fluidly coupled to the dispensing port and configured to maintain a supply of the stimulant solution; and wherein the stimulant in the stimulant solution is also diluted sufficiently to avoid waking the patient when continuously delivered over a period of time.

292. Another embodiment is a method for causing a natural response in an individual to maintain a sleep state, the method comprising: providing a stimulant that induces a physiological response within a mouth, throat, or airway of the individual where the physiological response causes a change in the individual to maintain or improve a state of sleep; delivering the stimulant in the mouth to induce the physiological response; and controlling an amount of the stimulant that is delivered to allow the individual to maintain the sleep state.

293. Another embodiment is the method of embodiment 292, wherein delivering the stimulant comprises delivering the stimulant at a location behind one or more teeth in the mouth.

294. Another embodiment is a method for improving sleep for an individual, the method comprising: providing a stimulant that induces a physiological response within a mouth, throat, or airway of the individual; delivering the stimulant at a location behind one or more teeth in the mouth to induce the physiological response; and controlling an amount of the stimulant that is delivered to allow the individual to maintain a sleep state.

295. Another embodiment is the method, device, or system of any of the other stimulant delivery embodiments elsewhere disclosed herein, such as for example the numbered embodiments above or below, wherein a physiological response is stimulated which comprises a degree of tongue movement and/or increased tongue muscle tone that is sufficient to open the airway to reduce an incidence of sleep disorder breathing.

296. Another embodiment is the method, device, or system of any of the other stimulant delivery embodiments elsewhere disclosed herein, such as for example the numbered embodiments above or below, wherein a physiological response is stimulated which comprises swallowing.

297. Another embodiment is the method, device, or system of embodiment 296 above, wherein at least one of a rate or volume of fluid delivery and a degree of stimulated salivation is sufficient to cause the individual or subject to swallow.

298. Another embodiment is the method, device, or system of any of the other stimulant delivery embodiments elsewhere disclosed herein, such as for example the numbered embodiments above or below, wherein providing the stimulant comprises automatically delivering the stimulant from a supply source while the individual is in the sleep state.

299. Another embodiment is the method, device, or system of any of the other embodiments elsewhere disclosed herein, such as for example the numbered embodiments above or below, wherein a physiological response is stimulated that reduces vibrations of a soft palate or uvula without waking the individual.

300. Another embodiment is the method, device, or system of any of the other stimulant delivery embodiments elsewhere disclosed herein, such as for example the numbered embodiments above or below, wherein providing the stimulant includes positioning an oral appliance within the mouth having a delivery port that delivers the stimulant to the tongue.

301. Another embodiment is the method, device, or system of any of the other oral appliance embodiments elsewhere disclosed herein, such as for example the numbered embodiments above or below, wherein positioning the oral appliance within the mouth comprises positioning the oral appliance on at least one of the lower front teeth such that the delivery port of the oral appliance is directly adjacent to the posterior side of the upper front teeth.

302. Another embodiment is the method, device, or system of any of the other oral appliance embodiments elsewhere disclosed herein, such as for example the numbered embodiments above or below, wherein positioning the oral appliance within the mouth comprises positioning the oral appliance on at least one of the upper front teeth such that the delivery port of the oral appliance is directly adjacent to the posterior side of the upper front teeth.

303. Another embodiment is the method, device, or system of any of the other oral appliance embodiments elsewhere disclosed herein, such as for example the numbered embodiments above or below, wherein the oral appliance comprises at least one of a mandibular advancement device, a continuous positive airway pressure device, a mouthguard, a custom molded mouthpiece, and a retainer.

304. Another embodiment is the method, device, or system of any of the other oral appliance stimulant delivery embodiments elsewhere disclosed herein, such as for example the numbered embodiments above or below, where the oral appliance comprises an internal reservoir coupled to a dispensing or delivery port, the internal reservoir containing at least a portion of the stimulant.

305. Another embodiment is the embodiment 304 above, further comprising a valve, wherein providing the stimulant comprises opening of the valve to dispense the stimulant.

306. Another embodiment is the embodiment of 305 above, wherein the delivery port comprises the valve.

307. Another embodiment is the embodiment of 305 above, wherein the reservoir is fluidly coupled to the dispensing or delivery port, and the stimulant comprises a fluid.

308. Another embodiment is the method, device, or system of any of the other stimulant delivery embodiments elsewhere disclosed herein, such as for example the numbered embodiments above or below, where providing the stimulant comprises providing an external reservoir containing the stimulant.

309. Another embodiment is the method, device, or system of any of the other tongue position stimulation embodiments elsewhere disclosed herein, such as for example the numbered embodiments above or below, further comprising providing a second stimulant to trigger an olfactory response in the sleeping individual.

310. Another embodiment is the method, device, or system of any of the other stimulant delivery embodiments elsewhere disclosed herein, such as for example the numbered embodiments above or below, where the stimulant comprises a substance comprising at least one of a sour taste, a citric taste, and a sweet taste.

311. Another embodiment is the method, device, or system of any of the other stimulant delivery embodiments elsewhere disclosed herein, such as for example the numbered embodiments above or below, wherein the stimulant comprises xylitol.

312. Another embodiment is the method, device, or system of any of the other controlled stimulant delivery embodiments elsewhere disclosed herein, such as for example the numbered embodiments above or below, wherein controlling the amount of stimulant comprises intermittently pausing delivery of the stimulant comprises pausing the stimulant until a triggering signal restarts delivery of the stimulant.

313. Another embodiment is the embodiment 312, further comprising using a dispensing unit in electrical communication with a sensor assembly, wherein the triggering signal is generated in response to a sensed parameter that is sensed by a sensor of the sensor assembly.

314. Another embodiment is the method, device, or system of any of the other sensor embodiments elsewhere disclosed herein, such as for example the numbered embodiments above or below, wherein the sensor comprises a pressure sensor, an optical sensor, a sound sensor, a movement sensor, or an electro-magnetic sensor.

315. Another embodiment is the method, device, or system of any of the other sensor embodiments elsewhere disclosed herein, such as for example the numbered embodiments above or below, wherein the sensor is positioned in the mouth and generates a signal based on a movement or position of the tongue.

316. Another embodiment is the method, device, or system of any of the other embodiments related to sensors, triggering signals, and controlled delivery of stimulant as elsewhere disclosed herein, such as for example the numbered embodiments above or below, wherein the amount of stimulant delivered is determined by the triggering signal.

317. Another embodiment is the method, device, or system of any of the other embodiments related to sensors, triggering signals, and controlled delivery of stimulant as elsewhere disclosed herein, such as for example the numbered embodiments above or below, further comprising measuring a degree of tongue movement with the sensor and using the triggering signal to determine the amount of stimulant delivery based on the degree of movement.

318. Another embodiment is the method, device, or system of any of the other embodiments related to sensors, triggering signals, and controlled delivery of stimulant as elsewhere disclosed herein, such as for example the numbered embodiments above or below, wherein controlling delivery of the stimulant, including but not limited to intermittently pausing delivery, are timed with an event or physiologic parameter related to or comprising at least one of respiration, respiratory effect, respiratory flow, hypoxia, hypopnea, oxygen saturation, pausing the stimulant until a triggering signal restarts delivery of the stimulant.

319. Another embodiment is the method, device, or system of any of the other embodiments related to therapeutic agent delivery via a fluid reservoir coupled to a dispensing port on an oral appliance, such as for example the numbered embodiments above or below, wherein a valve is provided which is located in a fluid path between the fluid reservoir and the dispensing port, and wherein the valve is adjustable to allow for a variable dispensing rate of the stimulant through the dispensing port.

320. Another embodiment is the embodiment 319 above, wherein the valve is adjustable to allow for intermittent change in the delivery, such as for example but not limited to intermittently pausing delivery, of the stimulant.

321. Another embodiment is any one of the preceding system embodiments above, to extent comprising a therapeutic agent provided on or within the oral device for delivery to the mouth in the secured configuration, and further comprising:
  a coating deposited on a surface of the oral device at a delivery location; wherein the therapy comprises a therapeutic agent contained within the coating; and
  wherein the coating is configured to release the therapeutic agent into the mouth at the delivery location.

322. Another embodiment is embodiment 321 above, and wherein the coating is deposited onto the dispensing surface via an ultraviolet (UV) light linking process.

323. Another embodiment is embodiment 321 above, and wherein the coating is deposited onto the dispensing surface via a solvent-based deposition.

324. Another embodiment comprises the embodiment 321 above, and further comprising a capsule or film over the coating and configured to dissolve over sufficient time for the patient to fall asleep before the therapeutic agent, such as a stimulant (such as a taste compound), starts to release into the mouth.

325. Another embodiment comprises the embodiment 324 above, comprising multiple alternating layers of the coating containing the therapeutic agent and the film, respectively.

326. Another embodiment comprises the embodiment 325 above, comprising multiple alternating layers of a coating comprising a taste compound and tasteless transition layers so that intermittent delivery of the taste is accomplished as the alternating layers dissolve.

327. Another embodiment comprises any one of the preceding system embodiments above, to extent comprising a therapeutic agent provided on or within the oral device for delivery to the mouth in the secured configuration, and further comprising a coating or capsule coupled to the oral device and comprising multiple alternating dissolvable layers configured for elevated and reduced delivery of therapeutic agent, respectively.

328. Another embodiment comprises the embodiment 327 above, comprising multiple alternating layers of therapeutic agent and agent-less transition layers configured for intermittent delivery of the therapeutic agent.

329. Another embodiment is any one of the preceding method embodiments above, comprising containing a therapeutic agent on or within the oral device for delivery to the mouth in the secured configuration, and further comprising:
coupling the therapy to the oral device by depositing a therapeutic agent in a surface coating on a dispensing surface of the oral device at a delivery location; and
delivering the therapy into the mouth via the oral device by releasing the therapeutic agent into the mouth via the surface coating at the delivery location.

330. Another embodiment is embodiment 329 above, and further comprising depositing the coating onto the dispensing surface via an ultraviolet (UV) light linking process.

331. Another embodiment is embodiment 329 above, and further comprising depositing the coating onto the dispensing surface via a solvent-based deposition.

332. Another embodiment comprises the embodiment 329 above, and further comprising a capsule or film deposited over the coating and configured to dissolve in the mouth over sufficient time for the patient to fall asleep before the therapeutic agent, such as a stimulant (such as a taste compound), starts to release from the coating into the mouth.

333. Another embodiment comprises the embodiment 332 above, comprising sequentially dissolving multiple alternating layers of the coating containing the therapeutic agent and the film, respectively, over time so as to control agent delivery to change over time.

334. Another embodiment comprises the embodiment 333 above, comprising dissolving multiple alternating layers of the coating comprising a taste compound and the film comprising tasteless transition layers, so that intermittent delivery of the taste is accomplished as the alternating layers dissolve.

335. Another embodiment comprises any one of the preceding method embodiments above and comprising providing a therapeutic agent on or within the oral device for delivery to the mouth in the secured configuration, and further comprising:
coupling a coating or capsule to the oral device and comprising multiple alternating dissolvable layers; and
allowing the alternating dissolvable layers to dissolve sequentially over time for elevated and reduced delivery of therapeutic agent, respectively, over time.

336. Another embodiment comprises the embodiment 335 above, wherein:
the multiple alternating layers comprise therapeutic agent and agent-less transition layers; and
dissolving the alternating layers sequentially over time allows intermittent delivery of the therapeutic agent over time.

337. Another embodiment is any one of the embodiments above and comprising delivery of a therapeutic agent into the mouth via the oral device, and wherein the therapeutic agent comprises a non-gas preparation for delivery.

338. Another embodiment is any one of the system embodiments above, to extent related to delivering a therapy to an anterior portion of the mouth, wherein the oral device in the secured configuration is configured to isolate local delivery of the therapy at only an anterior location within the mouth at or adjacent to the front incisors.

339. Another embodiment is the system embodiment 338 above, used in any one of the respective method embodiments above, wherein the method further comprises locally delivering the therapy to only the anterior portion of the mouth at or adjacent to the front incisors.

The above illustrations are examples of the invention described herein. Because of the scope of the invention, it is specifically contemplated that combinations of aspects of specific embodiments or combinations of the specific embodiments themselves are within the scope of this disclosure.

Although the description herein contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art. Furthermore, reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present disclosure and claims. Moreover, it is not necessary for a device or method to address each and every problem sought to be solved by the present invention, for it to be encompassed by the present disclosure and claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A tongue position stimulator (TST) system for delivering a stimulant to stimulate anterior repositioning of a tongue in a mouth of a subject in order to treat sleep disorder breathing, comprising:
an oral device configured to be secured within the mouth in a secured configuration;
a source of stimulant coupled to the oral device;
wherein the oral device in the secured configuration is configured to deliver the stimulant at an anterior location that is at or adjacent to, and corresponds laterally along the teeth with, the front incisors within the mouth;

wherein at least one of (i) the delivery is locally isolated to only the anterior location, and (ii) the stimulant comprises an electrical current and the source comprises an electrical current source; and wherein the delivery of the stimulant at the anterior location is configured to stimulate the anterior repositioning of the tongue during sleep.

2. The system of claim 1, wherein:
the stimulant delivery from the oral device and into the mouth is locally isolated to only the anterior location;
the stimulant comprises an electrical current; and
the source comprises an electrical current source.

3. The system of claim 1, wherein the stimulant delivery from the oral device and into the mouth is locally isolated to only the anterior location.

4. The system of claim 1, wherein:
the stimulant comprises an electrical current; and
the source comprises an electrical current source.

5. The system of claim 4, wherein:
the electrical current source comprises a radiofrequency (RF) current source; and
the stimulant comprises an RF current.

6. The system of claim 4, further comprising:
at least one electrode coupled to the oral device at an electrode position coinciding with the anterior location in the secured configuration;
wherein the electrical current source is electrically coupled to the at least one electrode; and
wherein the oral device in the secured configuration is configured to deliver the electrical current at the anterior location via the at least one electrode.

7. The system of claim 6, wherein the at least one electrode comprises at least one bipolar electrode assembly.

8. The system of claim 6, wherein the at least one electrode comprises at least one monopolar electrode.

9. The system of claim 4, further comprising:
a controller coupled to the electrical current source;
wherein the controller is configured to operate the electrical current source to control an electrical current delivery according to a variable delivery profile.

10. The system of claim 9, wherein:
the variable delivery profile is variable between a first condition and a second condition;
the first condition comprises a first level of electrical current; and
the second condition comprises a second level of electrical current that is lower than the first level.

11. The system of claim 10, wherein the second level of electrical current comprises zero electrical current.

12. The system of claim 11, further comprising:
a sensor configured to sense information related to at least one physiologic parameter of the subject associated with the sleep disorder breathing; and
wherein the controller is configured to actively control the variable delivery profile based upon the sensed information.

13. The system of claim 12, wherein:
the controller comprises a processor configured to run a software program embedded in a non-transitory computer readable medium to generate a set of control instructions from the software program in response to a set of input instructions received by the processor; and the set of input instructions is based upon the sensed information.

14. The system of claim 12, wherein:
the sensed information comprises a triggering event; and
the controller is configured to actively control the delivery profile to deliver the variable delivery profile of the stimulant at least in part in response to the triggering event.

15. The system of claim 12, wherein:
the sensor is positioned at a sensor location along the oral device that coincides with the anterior location in the secured configuration;
the sensor is configured to sense a change of a tongue position in the mouth; and
the controller is configured to adjust the variable delivery profile in response to the sensed tongue position change.

16. The system of claim 15, wherein:
the controller comprises a processor configured to run a software program embedded in a non-transitory computer readable medium to generate a set of control instructions from the software program in response to a set of input instructions received by the processor;
the set of input instructions is based upon the sensed information;
the sensor comprises at least one electrode at the sensor location;
the at least one electrode is electrically coupled to the electrical current source; and
the oral device, in the secured configuration, is configured to deliver the electrical current at the anterior location via the at least one electrode.

17. The system of claim 12, wherein the sensor is physically separate and apart from, and is configured to sense the sensed information at a different location from, the oral device in the secured configuration.

18. The system of claim 1, wherein the source of stimulant is contained within the oral device and located within the mouth in the secured configuration.

19. The system of claim 1, wherein:
the source of stimulant is located outside the mouth in the secured configuration;
the source of stimulant is coupled to the oral device via a delivery assembly.

20. A tongue position stimulation (TST) method for delivering a stimulant to stimulate anterior repositioning of a tongue in a mouth of a subject in order to treat sleep disorder breathing, comprising:
securing an oral device within the mouth in a secured configuration;
coupling a source of stimulant to the oral device;
delivering the stimulant from the oral device in the secured configuration at an anterior location that is at or adjacent to, and corresponds laterally along the teeth with, the front incisors within the mouth;
wherein at least one of (i) the stimulant delivery comprises locally isolating the delivery of the stimulant to only the anterior location, and (ii) the stimulant comprises an electrical current and the source comprises an electrical current source; and
stimulating the anterior repositioning of the tongue during sleep in response to the stimulant delivery.

* * * * *